United States Patent
Yoo et al.

(10) Patent No.: US 10,858,432 B2
(45) Date of Patent: Dec. 8, 2020

(54) ANTIBODIES SPECIFIC TO GLYCOSYLATED PD-1 AND METHODS OF USE THEREOF

(71) Applicants: STCUBE, INC., Seoul (KR); BOARD OF REGENTS, THE UNIVERSITY OF TEXAS SYSTEM, Austin, TX (US)

(72) Inventors: Stephen S. Yoo, Centreville, VA (US); Ezra M. Chung, North Potomac, MD (US); Yong-Soo Kim, Rockville, MD (US); Seung-Oe Lim, Houston, TX (US); Chia-Wei Li, Houston, TX (US); Mien-Chie Hung, Houston, TX (US)

(73) Assignees: STCUBE, INC., Seoul (KR); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/778,663

(22) PCT Filed: Dec. 1, 2016

(86) PCT No.: PCT/US2016/064394
§ 371 (c)(1),
(2) Date: May 24, 2018

(87) PCT Pub. No.: WO2017/096026
PCT Pub. Date: Jun. 8, 2017

(65) Prior Publication Data
US 2019/0077866 A1 Mar. 14, 2019

Related U.S. Application Data

(60) Provisional application No. 62/262,303, filed on Dec. 2, 2015.

(51) Int. Cl.
| | | |
|---|---|---|
| C07K 16/00 | (2006.01) | |
| C07K 16/46 | (2006.01) | |
| C07K 16/24 | (2006.01) | |
| A61K 39/395 | (2006.01) | |
| G01N 33/53 | (2006.01) | |
| C07K 16/28 | (2006.01) | |
| C07K 16/44 | (2006.01) | |
| A61K 47/68 | (2017.01) | |
| C07K 16/18 | (2006.01) | |
| A61P 35/00 | (2006.01) | |
| A61K 9/00 | (2006.01) | |

(52) U.S. Cl.
CPC ........ *C07K 16/2818* (2013.01); *A61K 9/0019* (2013.01); *A61K 39/395* (2013.01); *A61K 47/6849* (2017.08); *A61P 35/00* (2018.01); *C07K 16/18* (2013.01); *C07K 16/28* (2013.01); *C07K 16/44* (2013.01); *C07K 2317/34* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2003/0148406 A1 | 8/2003 | King et al. |
| 2008/0118978 A1 | 5/2008 | Sato et al. |
| 2008/0187954 A1 | 8/2008 | Kallmeier et al. |
| 2009/0041783 A1 | 2/2009 | Takayama et al. |
| 2009/0176317 A1 | 7/2009 | Kwon et al. |
| 2010/0285039 A1 | 11/2010 | Chen |
| 2011/0271358 A1 | 11/2011 | Freeman et al. |
| 2012/0034229 A1 | 2/2012 | Rousselle et al. |
| 2013/0017251 A1 | 1/2013 | Huang et al. |
| 2014/0170134 A1 | 6/2014 | Schneewind et al. |
| 2017/0114135 A1* | 4/2017 | Codarri-Deak .... C07K 16/2818 |
| 2017/0247454 A1* | 8/2017 | Benz ................. C07K 16/2818 |
| 2018/0118830 A1 | 5/2018 | Yoo |

FOREIGN PATENT DOCUMENTS

| | | |
|---|---|---|
| WO | WO 2006/004988 | 1/2006 |
| WO | WO 2006/121168 | 11/2006 |
| WO | WO 2008/156712 | 12/2008 |
| WO | WO 2011/066389 | 6/2011 |
| WO | WO 2013/079174 | 6/2013 |
| WO | WO 2014/055897 A2 | 4/2014 |
| WO | WO 2014/055897 A3 | 4/2014 |
| WO | WO 2015/035606 | 3/2015 |
| WO | WO 2015/061668 | 4/2015 |
| WO | WO 2015/095418 | 6/2015 |

(Continued)

OTHER PUBLICATIONS

Leighton JK. Center for Drug Evaluation and Research. Application No. 125554Orig1s000. OPDIVO nivolumab) https://www.accessdata.fda.gov/drugsatfda_docs/nda/2014/125554Orig1s000SumR.pdf, Dec. 4, 2014) (Year: 2014).*

Lin et al. The PD-1/PD-L1 complex resembles the antigen-binding Fv domains of antibodies and T cell receptors. PNAS 105 (2008) 3011-3016 (Year: 2008).*

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*

(Continued)

*Primary Examiner* — Maher M Haddad
(74) *Attorney, Agent, or Firm* — Ballard Spahr LLP

(57) ABSTRACT

Antibodies that selectively bind to glycosylated PD-1 relative to unglycosylated PD-1 are provided. In some aspects, PD-1 polypeptides comprising glycosylated amino acid positions are also provided. Methods for making and using such antibodies and polypeptides (e.g., for the treatment of cancer) are also provided.

23 Claims, 8 Drawing Sheets

Figure 2:
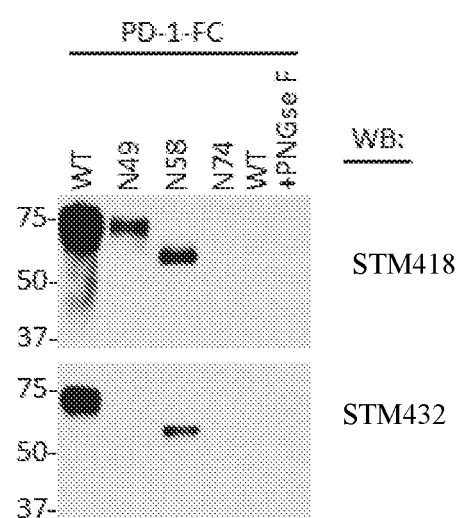

Specification includes a Sequence Listing.

(56) References Cited

FOREIGN PATENT DOCUMENTS

| WO | WO 2015/112800 | 7/2015 |
|---|---|---|
| WO | WO 2016/160792 | 10/2016 |
| WO | WO 2017/055443 | 4/2017 |

OTHER PUBLICATIONS

Vajdos et al. Comprehensive functional maps of the antigen-binding site of an anti-ErbB2 antibody obtained with shotgun scanning mutagenesis. J. Mol. Biol., Jul. 5, 2002, 320(2):415-28. (Year: 2002).*
Sun et al. Targeting Glycosylated PD-1 Induces Potent Antitumor Immunity. Cancer Res 2020;80:2298-310 (Year: 2020).*
U.S. Appl. No. 15/559,513, filed Sep. 19, 2017, Stephen S. Yoo.
U.S. Appl. No. 16/086,574, filed Sep. 19, 2018, Stephen S. Yoo.
U.S. Appl. No. 16/086,582, filed Sep. 19, 2018, Stephen S. Yoo.
U.S. Appl. No. 16/318,840, filed Jan. 18, 2019, Stephen S. Yoo.
Jacob Plieth et al.: 11 PD-I / PD-LI Combination Therapies 11, Sep. 8, 2015 (Sep. 8, 2015), XP055404205, Retrieved from the Internet: URL:nfo.evaluategroup.com/rs/607-YGS-364/i, mages/epv-pdct17.pdf [retrieved on Sep. 6, 2017].
M36239, GenBank Accession No. M36239, "Mouse Ig Kappa-chain mRNA V region, partial cds, from hybridoma H147-25H1VK," Apr. 27, 1993, retrieved on Jun. 9, 2016, http://www.ncbi.nlm.nih.gov/nuccore/M36239.
DQ372788, GenBank Accession No. DQ372788, "Mus Muculus clone AiDWTimmB-27 immunoglobulin kappa light chain mRNA, partial cds," Feb. 2, 2006, retrieved on Jun. 9, 2016, http://www.ncbi.nlm.nih.gov/nuccore/DQ372788.
Wang, C et al., In Vitro Characterization of the Anti-PD-1 Antibody Nivolumab, BMS-936558, and In Vivo Toxicology in Non-Human Primates. Cancer Immunology Research. May 28, 2014; vol. 2, No. 9; pp. 846-856; p. 848, col. 2, paragraph 4; DOI:10.1158/2326-6066.CIR-14-0040.
Jeffries, R, Glycosylation as a Strategy to Improve Antibody-Based Therapeutics. Nature Reviews Drug DIscovt1ry. M<trdr, 2009, Vul. 8, Nu. 3; pp. 220-234; p. 229, col. 1, paragraph 4 - p. 229, col. 2, paragraph 1; DOI: 10.1038/nrd2804.
Warrington, Arthur E et al: 1-39 11 Neuron-binding human monoclonal antibodies support central nervous system neurite extension 11, Journal of Neuropathology and Experimental Neurol, Lippincott Williams and Wilkins, New York, NY, vol. 63, No. 5, May 1, 2004 (May 1, 2004), pp. 461-473.
A J Hamilton et al: "A 34-to 38-Kilodalton Cryptococcus neoformans Glycoprotein Produced as an Exoantigen Bearing a Glycosylated Species-Specific Epitope 11",Infection and Immunity, vol . 60. No. 1 • Jan. 1, 1992 (Jan. 1, 1992). pp. 143-149.
Antje Danielczyk et al: 11 PankOMab: a potent new generation anti-tumour MUCI antibody 11 • Cancer Immunology, Immunotherapy, Springer, Berlin, DE, vol. 55, No. 11, Feb. 17, 2006 (Feb. 17, 2006). pp. 1337-1347.
Hertzog et al: 11 Oncofetal expression of the human intestinal mucin glycoprotein antigens in gastrointestinal epithelium defined by monoclonal antibodies. 11, International Journal of Cancer May 30, 1991. vol. 48, No. 3, May 30, 1991 (May 30, 1991), pp. 355-363.
US National Library of Medicine (NLM), Bethesda, MD, US; Nov. 2011 (Nov. 2011).Zhou Ying et al: 11 [Preparation and characterization of three novel monoclonal antibodies against human PD-LI]. 11 , XP002770553, Database accession No. NLM22078450, abstract & Zhou Ying et al: 11 [Preparation and characterization of three novel monoclonal antibodies against human PD-LI]. 11, Xi Bao Yu Fen Zi Mian Yi Xue Za Zhi =Chinese Journal of Cellular and Molecular Immunology Nov. 2011, vol. 27, No. 11, Nov. 2011 pp. 1208-1211.
Maria-Luisa Del Rio, et al: "Antibody-mediated signaling through PD-1 costimulates T cells and enhances CD28-dependent proliferation", European Journal of Immunology, vol. 35, No. 12, Dec. 1, 2005, pp. 3545-3560.
K. M. Mahoney et al: "PD-LI Antibodies to Its Cytoplasmic Domain Most Clearly Delineate Cell Membranes in Immunohistochemical Staining of Tumor Cells", Cancer Immunology Research, vol. 3 , No. 12, Dec. 1, 2015 (Dec. 1, 2015), pp. 1308-1315.
J W Kim et al: "Prospects for Targeting PD-1 and PD-LI in Various Tumor Types", Oncology (Norwalk), vol. 28, No. Suppl. 3, Nov. 10, 2014 (Nov. 10, 2014), pp. 15-28.
Chia-Wei Li et al: "Glycosylation and stabilization of programmed death ligand-1 suppresses T-cell activity", Nature Communications, vol. 7, Aug. 30, 2016 (Aug. 30, 2016) p. 12632.
Gang Hao et al., "Epitope characterization of an anti-PD-L 1 antibody using orthogonal approaches", J. Mal. Recagnit. 2015; 28: pp. 269-276.
Supplementary European Search Report issued for EP Patent Application No. EP 16871487 dated Apr. 18, 2019, 12 pages.
Yan G. Ni et al, "Development and Fit-for-Purpose Validation of a Soluble Human Programmed Death-1 Protein Assay", The AAPS Journal, vol. 17, No. 4, May 1, 2015 (May 1, 2015), pp. 976-987.
Eszter Lazar-Molnar "Crystal structure of the complex between programmed death-1 (PD-1) and its ligand PD-L2", Proceedings of the National Academy of Sciences of The United States of America, vol. 105, No. 30, Jul. 18, 2008 (Jul. 18, 2008), pp. 10483-10488.
Brown et al. Tolerance of single, but not multiple, amino acid replacements in antibody VH CDR 2: a means of minimizing B cell wastage from somatic hypermutation? J Immunol. May 1, 1996; 156(9):3285-91. (Year: 1996).
Morales-Betanzos et al. Quantitative Mass Spectrometry Analysis of PD-L 1 Protein Expression, N-glycosylation and Expression Stoichiometry with PD-1 and PD-L2 in Human Melanoma. Molecular & Cellular Proteomics 16: 10.107 4/mcp. RA 117.000037, 1705-1717, 2017. (Year: 2017).
David Yin-wei Lin et al., The PD-1 /PD-L 1 complex resembles the antigen-binding Fv domains of antibodies and T cell receptors, PNAS, Feb. 26, 2008, vol. 105, No. 8, pp. 3011-3016.
Jefferis, "Glycosylation as a Strategy to Improve Antibody-Based Therapeutics," Nature Reviews Drug Discovery, 8(3), pp. 226-234, 2009.
Wang et al., "In Vitro Characterization of the Anti-PD-1 Antibody Nivolumab, BMS-936558, and In Vivo Toxicology in Non-Human Primates," Cancer Immunology Research, 2(9), pp. 846-856, 2014.

* cited by examiner

A
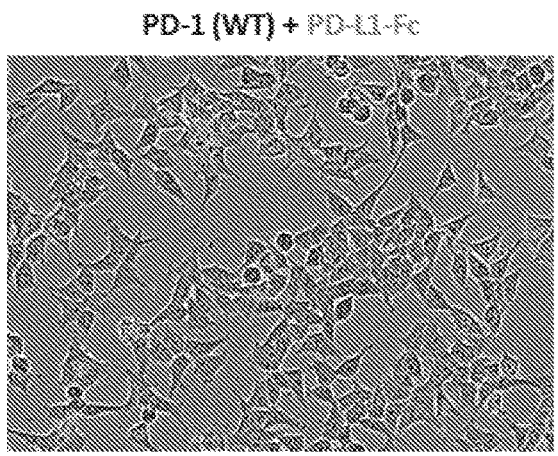
B
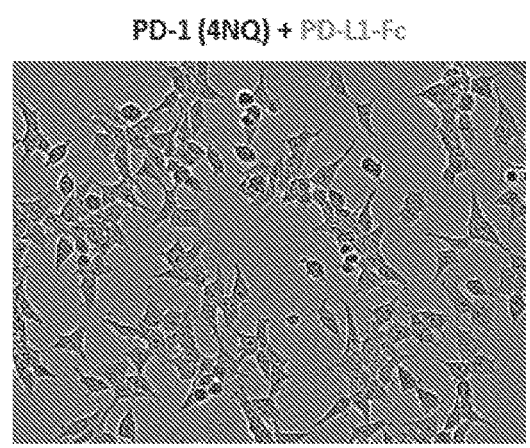
C
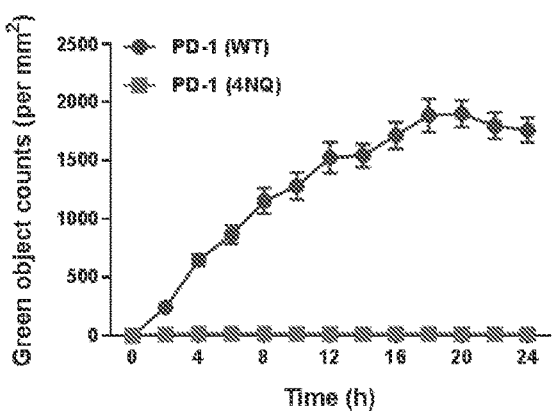
D
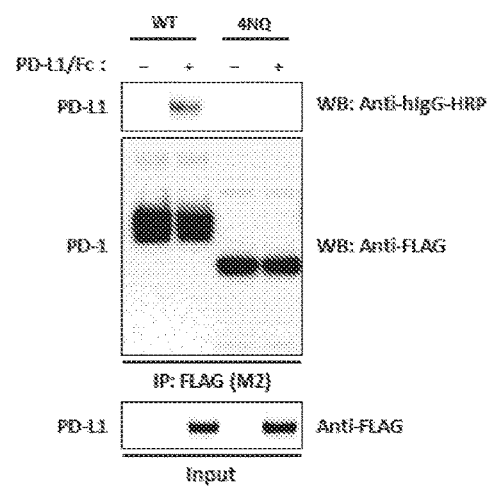
FIGS. 1A-D

US 10,858,432 B2

ANTIBODIES SPECIFIC TO GLYCOSYLATED PD-1 AND METHODS OF USE THEREOF

SEQUENCE LISTING

The instant application contains a Sequence Listing which has been filed electronically in ASCII format and is hereby incorporated by reference in its entirety. Said ASCII copy, created on Nov. 30, 2016, is named 24258_105005PCT_SL.txt and is 19,819 bytes in size.

FIELD

The present invention relates generally to the fields of medicine, molecular biology and oncology. More particularly, it concerns antibodies for treating cancers.

BACKGROUND

Perpetuation of T-cell activation has drastically reshaped the treatment of a broad spectrum of malignant cancer. For instance, the development of ipilimumab, the first FDA approved checkpoint blockade targeting T-cell response made treating metastatic melanoma probable (Hodi et al., *The New England Journal of Medicine* 363, 711-723 (2010)). While the anti-cytotoxic T lymphocyte antigen-4 (CTLA-4) monoclonal antibody showed promising results in treating melanoma patients, a second-generation checkpoint inhibitors targeting both PD-1 and PD-L1 have demonstrated better clinical activity and safety in phase III clinical trials (Topalian et al., *The New England Journal of Medicine* 366, 2443-2454 (2012); Brahmer et al., *The New England Journal of Medicine* 366, 2455-2465 (2012)). Because PD-L1 also possesses oncogenic potential that induces cancer cells progression (Topalian et al., *The New England Journal of Medicine* 366, 2443-2454 (2012); Page et al., *Annual Review of Medicine* 65, 185-202 (2014)), in addition to its immunosuppression activity, targeting PD-1/PD-L1 provides dual efficacy by blocking immunosuppression via PD-1 while reducing cell progression via PD-L1 (Okazaki et al., *Nature Immunology* 14, 1212-1218 (2013)) and is expected to have more sensitive outcome (Topalian et al., *The New England Journal of Medicine* 366, 2443-2454 (2012); Brahmer et al., *The New England Journal of Medicine* 366, 2455-2465 (2012); Hamid et al., *The New England Journal of Medicine,* 369, 134-144 (2013). In 2014, there were over 10 clinical trials ongoing in the U.S. testing the efficacy of anti-PD-L1 and/or anti-PD-1 antibodies either as a single agent or in combination (Page et al., *Annual Review of Medicine* 65, 185-202 (2014)). While there have been several successful clinic trials with promising outcomes, the pathophysiological function and regulatory mechanism of PD-L1 and PD-1 remains incompletely defined.

Reawakening silenced immune response has been recently added to a repertoire of treatment options after surgical removal, chemotherapy, radiotherapy, and targeted therapies. While the use of anti-CTLA-4 monoclonal antibody (Dunn et al., *Nature Immunology* 3, 991-998(2002); Leach et al., *Science* 271, 1734-1736 (1996)), initially demonstrated success in treating metastatic melanoma, it has been shown to also induce autoimmune response. Unlike anti-CTLA-4 which affects only immune cells, anti-PD-L1 and anti-PD-1 act mainly at the tumor sites which create the dual impacts from both cancer cell and T-cell, therefore limiting the adverse effects and providing better therapeutic efficacy (Okazaki et al., *Nature Immunology* 14, 1212-1218 (2013)). However, there remains a need for new therapeutics and methodologies for successful targeting of the PD-1/PD-L1 pathway in cancer cells.

SUMMARY

Provided herein are isolated monoclonal antibodies that selectively bind to glycosylated PD-1 relative to unglycosylated PD-1 (anti-glycPD-1 antibodies herein). In some aspects, the antibodies selectively bind to PD-1 glycosylated at positions N49, N58, N74 and/or N116 relative to unglycosylated PD-1.

In some embodiments, the isolated antibodies selectively bind to human PD-1 that has N49 glycosylation. In some embodiments, the isolated antibodies selectively bind to human PD-1 that has N58 glycosylation. In some embodiments, the isolated antibodies selectively bind to human PD-1 that has N74 glycosylation. In some embodiments, the isolated antibodies selectively bind to human PD-1 that has N116 glycosylation. In some embodiments, the isolated antibodies selectively bind to human PD-1 that has N49 and N58 glycosylation. In some embodiments, the isolated antibodies selectively bind to human PD-1 that has N49 and N74 glycosylation. In some embodiments, the isolated antibodies selectively bind to human PD-1 that has N49 and N116 glycosylation. In some embodiments, the isolated antibodies selectively bind to human PD-1 that has N58 and N74 glycosylation. In some embodiments, the isolated antibodies selectively bind to human PD-1 that has N58 and N116 glycosylation. In some embodiments, the isolated antibodies selectively bind to human PD-1 that has N74 and N116 glycosylation. In some embodiments, the isolated antibodies selectively bind to human PD-1 that has N49, N58 and N74 glycosylation. In some embodiments, the isolated antibodies selectively bind to human PD-1 that has N49, N58 and N116 glycosylation. In some embodiments, the isolated antibodies selectively bind to human PD-1 that has N49, N74 and N116 glycosylation. In some embodiments, the isolated antibodies selectively bind to human PD-1 that has N58, N74, and N116 glycosylation. In some embodiments, the isolated antibodies selectively bind to human PD-1 that has PD-1 has N49, N58, N74, and N116 glycosylation.

In some aspects, the antibody selectively binds to one or more glycosylation motifs. In some aspects, the antibody binds to a glycopeptide comprising a glycosylation motif and the adjacent peptide. In some aspects, the antibody binds to a peptide sequence that is located near one or more of the glycosylation motifs in three dimensions. In certain aspects, the antibody binds to glycosylated PD-1 with $K_d$ less than half of the $K_d$ exhibited relative to unglycosylated PD-1. In further aspects, the antibody binds to glycosylated PD-1 with $K_d$ at least 10 times less than the $K_d$ exhibited relative to unglycosylated PD-1.

In certain aspects, the anti-glycPD-1 antibodies bind to PD-1 and mask or screen one or more glycosylation motifs to block binding or other interation of a molecule with that motif and can block glycosylation of PD-1 at that glycosylation site. In specific embodiments, the anti-glycPD-1 antibody masks the glycosylation site at one or more of N49, N58, N74 and N116.

Provided in a particular aspect is the anti-glycPD-1 monoclonal antibody STM418, which has heavy and light chain variable domains having amino acid sequences of SEQ ID NOs: 3 and 5, respectively (mature $V_H$ and $V_L$ region amino acid sequences without any signal sequence), and antigen binding portions thereof, and humanized and chimeric forms thereof. Provided herein are anti-glycPD-1 antibodies that compete for binding to glycosylated PD-1 with STM418 MAb and/or bind to the same epitope as STM418. The epitope of STM418 is as follows, with contact residues within the PD-1 amino acid sequence indicated by underlining:

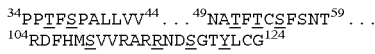

$^{34}$PPTFSPALLVV$^{44}$ ... $^{49}$NATFTCSFSNT$^{59}$ ...
$^{104}$RDFHMSVVRARRNDSGTYLCG$^{124}$ (Amino acids 34 to 44, 49 to 59 and 104 to 124 of SEQ ID NO:1). Provided are antibodies that bind an epitope with regions from amino acids 34 to 44, 49 to 59 and 104 to 124 of the glycosylated PD-1 sequence of SEQ ID NO: 1 and, in particular, with contacts at one or more of positions T36, S38, T51, T53, S55, S109, R115, S118 and Y121 of SEQ ID NO: 1. In specific embodiments, provided are antibodies that selectively bind glycosylated PD-1 and have binding contacts with all of positions 36, 38, 51, 53, 55, 109, 115, 118, and 121 of SEQ ID NO: 1.

Provided are the nucleic acid (DNA) and corresponding amino acid sequences of the heavy and light chain variable (V) domains of the STM418 MAb are shown in Table 3, infra. SEQ ID NOS: 2 and 3 are the nucleotide and amino acid sequences of the STM418 $V_H$ domain and SEQ ID NOS: 4 and 5 are the nucleotide and amino acid sequences of the mature form of the STM418 light kappa chain variable domain. Table 4 provides the Chothia, AbM, Kabat and Contact heavy and light chain V domain CDRs of STM418.

In an embodiment, the anti-glycPD-1 antibody that specifically and preferentially binds glycosylated PD-1 comprises a $V_H$ domain having an amino acid sequence of SEQ ID NO: 3 and/or a $V_L$ domain having an amino acid sequence of SEQ ID NO: 5. In an embodiment, the anti-glycPD-1 antibody competes for specific binding to glycosylated PD-1 with an antibody comprising a $V_H$ domain of SEQ ID NO: 3 and a $V_L$ domain of SEQ ID NO: 5. In other embodiments, the anti-glycPD-1 antibody comprises a $V_H$ domain that is at least 80%, 85%, 90%, 95%, 96%, 97%, 98% or 99% identical to the amino acid sequence of SEQ ID NO: 3 and/or a VL domain that is at least 80%, 85%, 90%, 95%, 96%, 97%, 98% or 99% identical to the amino acid sequence of SEQ ID NO: 5. These anti-glycPD-1 antibodies may be chimeric antibodies and comprise a human constant domain, for example, from a human IgG1, IgG2, IgG3 or IgG4.

In an embodiment, the anti-glycPD-1 antibody that specifically and preferentially binds glycosylated PD-1 comprises a $V_H$ domain comprising Chothia CDRs1-3 having amino acid sequences of SEQ ID NO: 6, SEQ ID NO: 7, and SEQ ID NO: 8, respectively; comprising AbM CDRs 1-3 having amino acid sequences of SEQ ID NO: 9, SEQ ID NO: 10, and SEQ ID NO: 8, respectively; comprising Kabat CDRs 1-3 having amino acid sequences of SEQ ID NO: 11, SEQ ID NO: 12, and SEQ ID NO: 8, respectively; or comprising Contact CDRs 1-3 having amino acid sequences of SEQ ID NO: 13, SEQ ID NO: 14, and SEQ ID NO: 15, respectively, or a combination thereof. In an embodiment, the anti-glycPD-1 antibody competes for specific binding to glycosylated PD-1 with an antibody comprising a $V_H$ domain comprising Chothia CDRs1-3 having amino acid sequences of SEQ ID NO: 6, SEQ ID NO: 7, and SEQ ID NO: 8, respectively; comprising AbM CDRs 1-3 having amino acid sequences of SEQ ID NO: 9, SEQ ID NO: 10, and SEQ ID NO: 8, respectively; comprising Kabat CDRs 1-3 having amino acid sequences of SEQ ID NO: 11, SEQ ID NO: 12, and SEQ ID NO: 8, respectively; or comprising Contact CDRs 1-3 having amino acid sequences of SEQ ID NO: 13, SEQ ID NO: 14, and SEQ ID NO: 15, respectively, or a combination thereof. In an embodiment, the anti-glycPD-1 antibody that specifically and preferentially binds glycosylated PD-1 comprises a $V_L$ domain comprising Chothia, AbM or Kabat CDRs1-3 having amino acid sequences of SEQ ID NO: 16, SEQ ID NO: 17, and SEQ ID NO: 18, respectively; or comprising Contact CDRs 1-3 having amino acid sequences of SEQ ID NO: 19, SEQ ID NO: 20, and SEQ ID NO: 21, respectively, or a combination thereof. In an embodiment, the anti-glycPD-1 antibody competes for specific binding to glycosylated PD-1 with an antibody comprising a $V_L$ domain comprising Chothia, AbM or Kabat CDRs1-3 having amino acid sequences of SEQ ID NO: 16, SEQ ID NO: 17, and SEQ ID NO: 18, respectively; or comprising Contact CDRs 1-3 having amino acid sequences of SEQ ID NO: 19, SEQ ID NO: 20, and SEQ ID NO: 21, respectively, or a combination thereof. In an embodiment, the anti-glycPD-1 antibody comprises or competes for binding to an antibody that comprises a $V_H$ domain comprising Chothia CDRs1-3 having amino acid sequences of SEQ ID NO: 6, SEQ ID NO: 7, and SEQ ID NO: 8, respectively; comprising AbM CDRs 1-3 having amino acid sequences of SEQ ID NO: 9, SEQ ID NO: 10, and SEQ ID NO: 8, respectively; comprising Kabat CDRs 1-3 having amino acid sequences of SEQ ID NO: 11, SEQ ID NO: 12, and SEQ ID NO: 8, respectively; or comprising Contact CDRs 1-3 having amino acid sequences of SEQ ID NO: 13, SEQ ID NO: 14, and SEQ ID NO: 15, respectively, and comprises a $V_L$ domain comprising Chothia, AbM or Kabat CDRs1-3 having amino acid sequences of SEQ ID NO: 16, SEQ ID NO: 17, and SEQ ID NO: 18, respectively; or comprising Contact CDRs 1-3 having amino acid sequences of SEQ ID NO: 19, SEQ ID NO: 20, and SEQ ID NO: 21, respectively. Preferably, the $V_H$ and $V_L$ domains have the same class of CDR, i.e., both have Chothia, AbM, Kabat or Contact CDRs.

In other embodiments, the anti-glycPD-1 antibody has a $V_H$ domain comprising CDRs H1, H2 and H3 with amino acid sequences that have 1, 2, 3, 4, or 5 amino acid substitutions in 1, 2 or 3 of the CDRs having the amino acid sequences of SEQ ID NO: 6, SEQ ID NO: 7, and SEQ ID NO: 8, respectively, or of the CDRs having the amino acid sequences of SEQ ID NO: 9, SEQ ID NO: 10, and SEQ ID NO: 8, respectively, or of the CDRs having the amino acid sequences of SEQ ID NO: 11, SEQ ID NO: 12, and SEQ ID NO: 8, respectively, or of the CDRs having the amino acid sequences of SEQ ID NO: 13, SEQ ID NO: 14, and SEQ ID NO: 15, respectively. The anti-glycPD-1 antibody may have a $V_L$ domain comprising CDRs L1, L2 and L3 with amino acid sequences that have 1, 2, 3, 4, or 5 amino acid substitutions in 1, 2 or 3 CDRs having the amino acid sequences of SEQ ID NO: 16, SEQ ID NO: 17, and SEQ ID NO: 18, respectively, or CDRs having the amino acid sequences of SEQ ID NO: 19, SEQ ID NO: 20, and SEQ ID NO: 21, respectively. The anti-glycPD-1 antibody may have amino acid substitutions in CDRs for both the $V_H$ and $V_L$ domains. In some embodiments, the amino acid substitutions are conservative substitutions.

Preferably the foregoing antibodies have human framework regions, i.e., are humanized forms of STM418, and optionally, comprise a human constant domain, for example, from a human IgG1, IgG2, IgG3 or IgG4.

It will be appreciated by those skilled in the art that one or more amino acid substitutions may be made in the CDRs and/or framework regions of a humanized antibody to improve binding affinity or other parameter. In embodiments, the anti-glycPD-1 antibody competes for specific binding to glycosylated PD-1 with an antibody comprising the above-described $V_H$ and $V_L$ domains and the CDRs therein. In embodiments, the anti-glycPD-1 antibody binds to glycosylated PD-1 with a $K_d$ less than half of the $K_d$ exhibited by the antibody's binding to unglycosylated PD-1. In an embodiment, the anti-glycPD-1 antibody binds to glycosylated PD-1 protein with a $K_d$ at least 5 times less than the $K_d$ exhibited relative to unglycosylated PD-1. In an embodiment, the anti-glycPD-1 antibody binds to glycosylated PD-1 protein with a $K_d$ at least 10 times less than the $K_d$ exhibited by the antibody's binding to unglycosylated PD-1 protein.

In an embodiment, in a cell flow cytometry binding assay as described in Example 2, the antibody exhibits binding as expressed as MFI to cells expressing wild type PD-1 that is 3 times, 5 times, 10 times, 20 times, 50 times, or 100 times greater than the MFI for binding to cells expressing unglycosylated PD-1. In an embodiment, the antibody is directly or indirectly detectable by a fluorescent label or marker. In an embodiment, the antibody is directly labeled with a fluorescent label or marker, such as FITC, or is detected by a fluorescently-labeled secondary antibody. In an embodiment, the binding affinity of STM418 MAb, or chimeric or humanized form thereof, for glycosylated PD-1 is from 5-20 nM or from 5-10 nM inclusive of the lower and upper values. In an embodiment, the antibody inhibits the interaction of PD-1 with PD-L1, and particularly inhibits the interaction of glycosylated PD-1 expressed by effector T-cells with PD-L1 expressed by tumor cells.

Provided in another particular aspect is the anti-glycPD-1 monoclonal antibody STM432 which has heavy and light chain variable domains having amino acid sequences of SEQ ID NOs: 23 and 25 respectively, (mature $V_H$ and $V_L$ region amino acid sequences), and antigen binding portions thereof, and humanized and chimeric forms thereof, that specifically bind glycosylated PD-1. The nucleic acid sequences encoding the heavy and light chain variable domains of the STM432 MAb, SEQ ID NOS. 22 and 24, respectively, are shown in Table 3, infra. Also shown in Table 5 are the Chothia, AbM, Kabat and Contact heavy and light chain V domain CDRs of STM432. STM432 MAb binds to an epitope on glycosylated PD-1 with the sequence $^{91}$DCRFRVTQLPNGRDFHM$^{107}$ . . . $^{123}$CGAISLAP KAQI$^{134}$ (amino acids D91 to M107 and C123 to I134 of SEQ ID NO: 1), with contact residues, R95, R103, S127, and K131 underlined. Accordingly, provided are anti-glycPD-1 antibodies that bind to the STM432 epitope as set forth above. Also provided are anti-glycPD-1 antibodies that compete for binding to glycosylated PD-1 with STM432 MAb.

In an embodiment, the anti-glycPD-1 antibody that specifically and preferentially binds glycosylated PD-1 comprises a $V_H$ domain having the amino acid sequence of SEQ ID NO: 23 and/or a $V_L$ domain having the amino acid sequence of SEQ ID NO: 25. In an embodiment, the anti-glycPD-1 antibody competes for specific binding to glycosylated PD-1 with an antibody comprising a $V_H$ domain of SEQ ID NO: 23 and a $V_L$ domain of SEQ ID NO: 25. In an embodiment, the anti-glycPD-1 antibody that specifically and preferentially binds glycosylated PD-1 comprises a $V_H$ domain that is at least 80%, 85%, 90%, 95%, 96%, 97%, 98% or 99% identical to the amino acid sequence of SEQ ID NO: 23 and/or a $V_L$ domain that is at least 80%, 85%, 90%, 95%, 96%, 97%, 98% or 99% identical to the amino acid sequence of SEQ ID NO: 25. These anti-glycPD-1 antibodies may be chimeric antibodies and comprise a human constant domain, for example, from a human IgG1, IgG2, IgG3 or IgG4.

In an embodiment, the anti-glycPD-1 antibody that specifically and preferentially binds glycosylated PD-1 comprises a $V_H$ domain comprising Chothia CDRs 1-3 having amino acid sequences of SEQ ID NO: 26, SEQ ID NO: 27, and SEQ ID NO: 28, respectively; AbM CDRs 1-3 having amino acid sequences of SEQ ID NO: 29, SEQ ID NO: 30, and SEQ ID NO: 28, respectively; Kabat CDRs 1-3 having amino acid sequences of SEQ ID NO: 31, SEQ ID NO: 32, and SEQ ID NO: 28, respectively; or Contact CDRs 1-3 having amino acid sequences of SEQ ID NO: 33, SEQ ID NO: 34, and SEQ ID NO: 35, respectively, or a combination thereof. In an embodiment, the anti-glycPD-1 antibody competes for specific binding to glycosylated PD-1 with an antibody comprising a $V_H$ domain comprising Chothia CDRs 1-3 having amino acid sequences of SEQ ID NO: 26, SEQ ID NO: 27, and SEQ ID NO: 28, respectively; AbM CDRs 1-3 having amino acid sequences of SEQ ID NO: 29, SEQ ID NO: 30, and SEQ ID NO: 28, respectively; Kabat CDRs 1-3 having amino acid sequences of SEQ ID NO: 31, SEQ ID NO: 32, and SEQ ID NO: 28, respectively; or Contact CDRs 1-3 having amino acid sequences of SEQ ID NO: 33, SEQ ID NO: 34, and SEQ ID NO: 35, respectively, or a combination thereof. In an embodiment, the anti-glycPD-1 antibody that specifically and preferentially binds glycosylated PD-1 comprises a $V_L$ domain comprising Chothia, AbM or Kabat CDRs 1-3 having amino acid sequences of SEQ ID NO: 36, SEQ ID NO: 37, and SEQ ID NO: 38, respectively or Contact CDRs 1-3 having amino acid sequences of SEQ ID NO: 39, SEQ ID NO: 40, and SEQ ID NO: 41, or a combination thereof. In an embodiment, the anti-glycPD-1 antibody competes for specific binding to glycosylated PD-1 with an antibody comprising a $V_L$ domain comprising Chothia, AbM or Kabat CDRs 1-3 having amino acid sequences of SEQ ID NO: 36, SEQ ID NO: 37, and SEQ ID NO: 38, respectively; or Contact CDRs 1-3 having amino acid sequences of SEQ ID NO: 39, SEQ ID NO: 40, and SEQ ID NO: 41, or a combination thereof. In an embodiment, the anti-glycPD-1 antibody that specifically and preferentially binds glycosylated PD-1 comprises, or competes for binding with an antibody that comprises a $V_H$ domain comprising Chothia CDRs 1-3 having amino acid sequences of SEQ ID NO: 26, SEQ ID NO: 27, and SEQ ID NO: 28, respectively; AbM CDRs 1-3 having amino acid sequences of SEQ ID NO: 29, SEQ ID NO: 30, and SEQ ID NO: 28, respectively, Kabat CDRs 1-3 having amino acid sequences of SEQ ID NO: 31, SEQ ID NO: 32, and SEQ ID NO: 28, respectively; or Contact CDRs 1-3 having amino acid sequences of SEQ ID NO: 33, SEQ ID NO: 34, and SEQ ID NO: 35, respectively, and comprises a $V_L$ domain comprising Chothia, AbM or Kabat CDRs 1-3 having amino acid sequences of SEQ ID NO: 36, SEQ ID NO: 7, and SEQ ID NO: 38, respectively, or Contact CDRs 1-3 having amino acid sequences of SEQ ID NO: 39, SEQ ID NO: 40, and SEQ ID NO: 41.

Provided in certain embodiments are anti-glycPD-1 antibodies which have a $V_H$ domain comprising CDRs H1, H2 and H3 with amino acid sequences that have 1, 2, 3, 4, or 5 amino acid substitutions in 1, 2 or 3 CDRs having the amino acid sequences of SEQ ID NO: 26, SEQ ID NO: 27, and SEQ ID NO: 28, respectively; or SEQ ID NO: 29, SEQ ID NO: 30, and SEQ ID NO: 28, respectively; or SEQ ID NO: 31, SEQ ID NO: 32, and SEQ ID NO: 28, respectively; or SEQ ID NO: 33, SEQ ID NO: 34, and SEQ ID NO: 35, respectively. The anti-glycPD-1 antibody also may have a $V_L$ domain comprising CDRs L1, L2 and L3 with amino acid sequences that have 1, 2, 3, 4, or 5 amino acid substitutions in 1, 2 or 3 CDRs having the amino acid sequences of SEQ ID NO: 36, SEQ ID NO: 37, and SEQ ID NO: 38, respectively; or SEQ ID NO: 39, SEQ ID NO: 40, and SEQ ID NO: 41, respectively. The anti-glycPD-1 antibody may have amino acid substitutions in CDRs in both the $V_H$ and $V_L$ domains. In some embodiments, the amino acid substitutions are conservative substitutions.

In embodiments, the anti-glycPD-1 antibody competes for specific binding to glycosylated PD-1 with an antibody comprising the above-described $V_H$ and $V_L$ domains and the CDRs therein. Preferably these antibodies have human framework regions, i.e., are humanized forms of STM432, and optionally, comprise a human constant domain, for example, from a human IgG1, IgG2, IgG3 or IgG4. It will be appreciated by those skilled in the art that one or more amino acid substitutions may be made in the CDRs or framework regions of a humanized antibody to improve binding affinity or other parameter. In embodiments, the anti-glycPD-1 antibody binds to glycosylated PD-1 with a $K_d$ less than half of the $K_d$ exhibited relative to unglycosylated PD-1. In embodiments, the anti-glycPD-1 antibody binds to glycosylated PD-1 with a $K_d$ less than half of the $K_d$ exhibited relative to unglycosylated PD-1. In an embodiment, the anti-glycPD-1 antibody binds to glycosylated PD-1 protein with a $K_d$ at least 5 times less than the $K_d$ exhibited by the antibody's binding to unglycosylated PD-1. In an embodiment, the anti-glycPD-1 antibody binds to glycosylated PD-1 protein with a $K_d$ at least 10 times less than the $K_d$ exhibited by the antibody's binding to unglycosylated PD-1 protein. In an embodiment, in a cell flow cytometry binding assay as described in Example 5, the antibody exhibits binding as expressed as MFI to cells expressing WT PD-1 that is 3 times, 5 times, 10 times, 20 times, 30 times or 50 times greater than the MFI for binding to cells expressing unglycosylated PD-1. In an embodiment, the antibody is directly or indirectly detectable by a fluorescent label or marker. In an embodiment, the antibody is directly labeled with a fluorescent label or marker such as FITC. In an embodiment, the binding affinity of STM432 MAb, or binding domain or humanized or chimeric form thereof, for glycosylated PD-1 is from 5-20 nM or from 5-10 nM inclusive of the lower and upper values. In an embodiment, the antibody inhibits the interaction of PD-1 with PD-1, and particularly inhibits the interaction of glycosylated PD-1 expressed by effector T-cells with PD-L1 expressed by tumor cells.

In some aspects, the antibody is recombinant. In certain aspects, the antibody is an IgG, IgM, IgA or an antigen binding fragment thereof. In other aspects, the antibody is a Fab', a F(ab')2, a F(ab')3, a monovalent scFv, a bivalent scFv, a bispecific antibody, a bispecific scFv, or a single domain antibody. In some aspects, the antibody is a human or humanized antibody. In further aspects, the antibody is conjugated to an imaging agent, a chemotherapeutic agent, a toxin or a radionuclide.

In a further embodiment, provided herein is a composition comprising an antibody of the embodiments (e.g., an antibody selectively binds to glycosylated PD-1 relative to unglycosylated PD-1) in a pharmaceutically acceptable carrier.

In still a further embodiment there is provided an isolated polypeptide comprising a fragment of at least 7 (e.g., at least 8, 9, 10, 11, 12, 13, 14, 15, 16, 17, 18, 19, 20 or more) contiguous amino acids of human PD-1 comprising at least one amino acid corresponding to position N49, N58, N74 or N116 of human PD-1. In further aspects, an isolated polypeptide of the embodiments comprises a fragment of at least 7 (e.g., at least 8, 9, 10, 11, 12, 13, 14, 15, 16, 17, 18, 19, 20 or more) contiguous amino acids of human PD-1, comprising at least one amino acid corresponding to position N49, N58, N74 or N116 of human PD-1 and wherein at least one of said amino acids corresponding to position N49, N58, N74 or N116 of human PD-1 is glycosylated. In some aspects, a polypeptide of the embodiments is fused or conjugated to an immunogenic polypeptide (e.g., keyhole limpet hemocyanin, KLH). In certain aspects, the polypeptide further comprises a Cys residue at the C- or N-terminus. For example, in some aspects, the polypeptide is conjugated to an immunogenic polypeptide by a disulfide linkage at the Cys residue.

In yet a further embodiment, a composition is provided comprising a polypeptide comprising a fragment of at least 7 (e.g., at least 8, 9, 10, 11, 12, 13, 14, 15, 16, 17, 18, 19, 20 or more) contiguous amino acids of human PD-1 comprising at least one amino acid corresponding to position N49, N58, N74 or N116 of human PD-1, wherein at least one of said amino acids corresponding to position N49, N58, N74 or N116 of human PD-1 is glycosylated, wherein the polypeptide is formulated in a pharmaceutically acceptable carrier.

In yet a further embodiment, an immunogenic composition is provided comprising a polypeptide comprising a fragment of at least 7 contiguous amino acids of human PD-1 comprising at least one amino acid corresponding to position N49, N58, N74 or N116 of human PD-1, wherein at least one of said amino acids corresponding to position N49, N58, N74 or N116 of human PD-1 is glycosylated, wherein the polypeptide is formulated in a pharmaceutically acceptable carrier. In some aspects, the immunogenic composition further comprises an adjuvant, such as alum or Freund's adjuvant.

In still a further embodiment provided herein is a method for treating a subject having a cancer comprising administering an effective amount of an antibody or an isolated polypeptide of the embodiments to the subject. In certain aspects, a method for treating a cancer comprises administering an effective amount of a polypeptide (e.g., a glycosylated PD-1 polypeptide) to a subject. In further aspects, a method of treating a cancer comprises administering an effective amount of an antibody of the embodiments (e.g., an antibody selectively binds to glycosylated PD-1 relative to unglycosylated PD-1), such as, but not limited to humanized or chimeric forms of STM418 or STM432, or antibodies that compete for binding to glycosylated PD-1 with STM418 or STM432, to a subject. In some aspects, the cancer is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In certain aspects, the cancer is an adrenal cancer, an anal cancer, a bile duct cancer, a bladder cancer, a bone cancer, a brain/CNS tumor in an adult, a brain/CNS tumor in a child, a breast cancer, a breast cancer in a man, cancer in an adolescent, cancer in a child, cancer in a young adult, cancer of unknown primary, Castleman disease, cervical cancer, colon/rectum cancer, endometrial cancer, esophagus cancer, Ewing family tumor, eye cancer, gallbladder cancer, gastrointestinal carcinoid tumor, gastrointestinal stromal tumor (GIST), gestational trophoblastic disease, Hodgkin disease, Kaposi sarcoma, kidney cancer, laryngeal or hypopharyngeal cancer, leukemia (e.g., adult acute lymphocytic (ALL), acute myeloid (AML), chronic lymphocytic (CLL), chronic myeloid (CML), chronic myelomonocytic (CMML), childhood leukemia), liver cancer, lung cancer (e.g., non-small cell, small cell), lung carcinoid tumor, lymphoma, lymphoma of the skin, malignant mesothelioma, multiple myeloma, myelodysplastic syndrome, naval cavity cancer, paranasal sinus cancer, nasopharyngeal cancer, neuroblastoma, non-Hodgkin lymphoma, non-Hodgkin lymphoma in a child, oral cavity cancer, oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma (e.g., adult soft tissue cancer), skin cancer (e.g., basal and squamous cell, melanoma, merkel cell), small intestine cancer, stomach cancer, testicular cancer, thymus cancer, thyroid cancer, uterine sarcoma, vaginal cancer, vulvar cancer, Waldenstrom macroglobulinemia, or Wilms tumor. In certain aspects, the antibody is in a pharmaceutically acceptable composition. In further aspects, the antibody is administered systemically. In particular aspects, the antibody is administered intravenously, intradermally, intratumorally, intramuscularly, intraperitoneally, subcutaneously or locally.

In some aspects, the method further comprises administering at least a second anticancer therapy to the subject. In certain aspects, wherein the second anticancer therapy is a surgical therapy, chemotherapy, radiation therapy, cryotherapy, hormonal therapy, immunotherapy or cytokine therapy.

In yet still a further embodiment provided herein is a method for assessing PD-1 glycosylation, N-linked glycosylation or N-glycosylation comprising contacting the PD-1-containing sample with an antibody of the embodiments (e.g., an antibody selectively binds to glycosylated PD-1 relative to unglycosylated PD-1). In some aspects, the method is an in vitro method. In certain aspects, the sample is cell sample.

In yet still a further embodiment a method of making an antibody is provided comprising administering a polypeptide according to the embodiments (e.g., a polypeptide having a fragment of at least 7 contiguous amino acids of human PD-1 comprising at least one amino acid corresponding to position N49, N58, N74 or N116 of human PD-1, wherein at least one of said amino acids corresponding to position N49, N58, N74 and N116 of human PD-1 is glycosylated) to an animal and isolating the antibody from the animal. For example, the animal can be a mouse, rat, rabbit or human. In certain aspects a method further includes identifying the CDRs of the antibody and humanizing the sequences surrounding the CDRs to produce a humanized antibody. In still further aspects, the method comprises recombinantly expressing the humanized antibody. Thus, in a further embodiment, provided herein is an isolated antibody produced by the foregoing method. Thus, in some embodiments, provided herein is an isolated antibody that selectively binds to a polypeptide of the embodiments (e.g., a polypeptide comprising a fragment of at least 7 contiguous amino acids of human PD-1 comprising at least one amino acid corresponding to position N49, N58, N74 or N116 of human PD-1, wherein at least one of said amino acids corresponding to position N49, N58, N74 or N116 of human PD-1 is glycosylated) relative to unglycosylated PD-1.

FIGURE LEGENDS

FIGS. 1A-1D. PD-L1-binding to PD-1 is glycosylation-specific. (A and B) Time lapse microscopy image (at 24 hr time point) showing the dynamic interaction between PD-L1 and wild type PD-1 and PD-1 4NQ mutant (i.e., unglycosylated PD-1) expressing 293T cells at the last time point. Green fluorescent (green fluorescent labeled PD-1/Fc protein) merged images (20×) of PD-1 WT (A) or 4NQ PD-1 mutant (B) expressing cells are shown. (C) The graph shows the quantitative binding of PD-L1/Fc protein to PD-1 WT or PD-1 4NQ expressing HEK293T cells at every hour time point. (D) Binding of PD-L1/Fc fusion to 293T cells expressing either wild type PD-1 or the 4NQ mutant PD-1 was assayed by co-immunoprecipitation and western blot analysis. WB:anti-hIgG-HRP indicates bound PD-L1/Fc as recognized by the anti-hIgG-HRP antibody in western blot analysis; WB:anti-FLAG indicates detection of PD-1 by western blot analysis; and Anti-FLAG in IP:FLAG indicates detection of PD-L1/Fc input by immunoprecipitation and detection with the anti-FLAG antibody.

FIG. 2. Western blot analysis of anti-glycPD-1 antibody binding to PD-1-Fc protein. Binding of STM418 and STM432 MAbs against wild type (WT), mutant (N49, N58 and N74) and wild type treated with PNGase is shown in western blot.

Figure 3A:
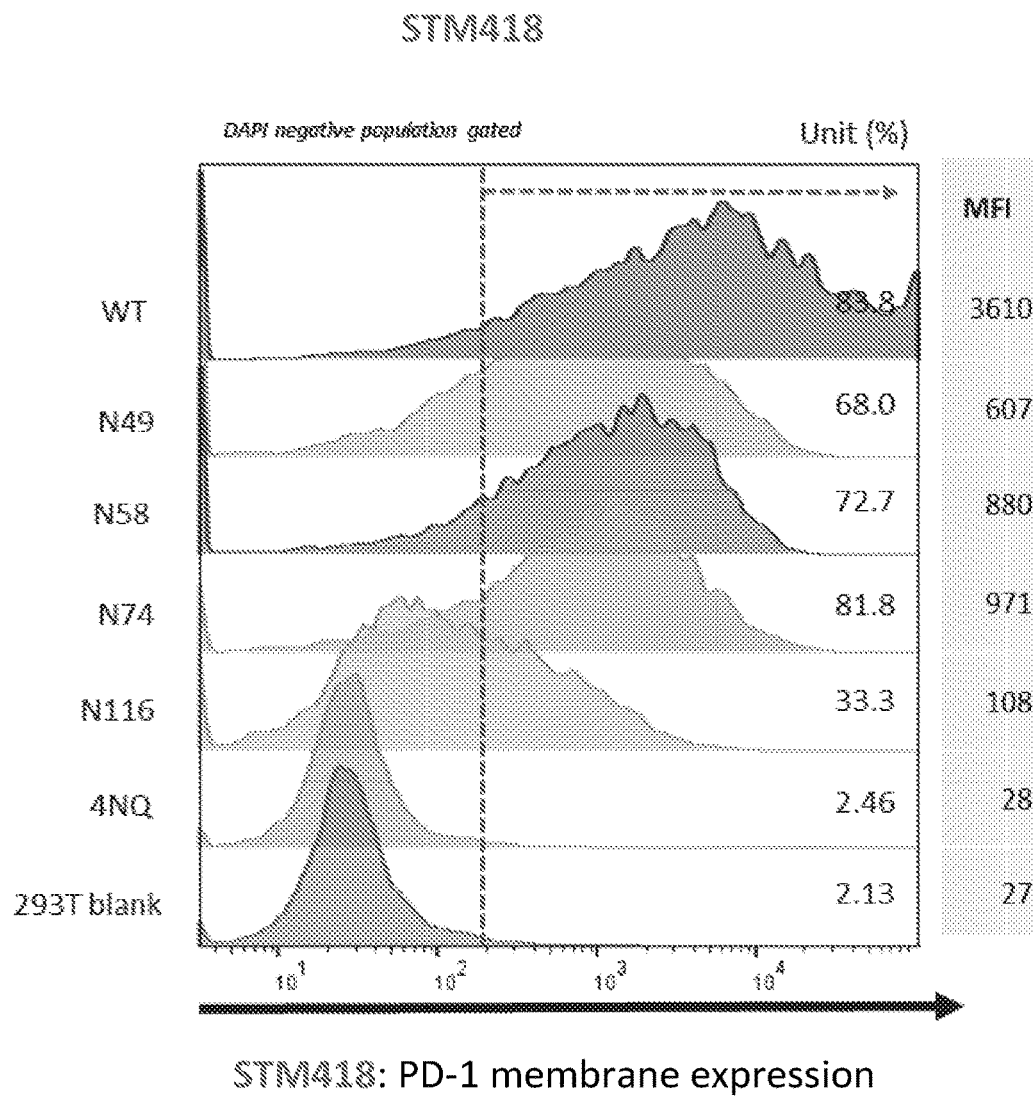
Figure 3B:
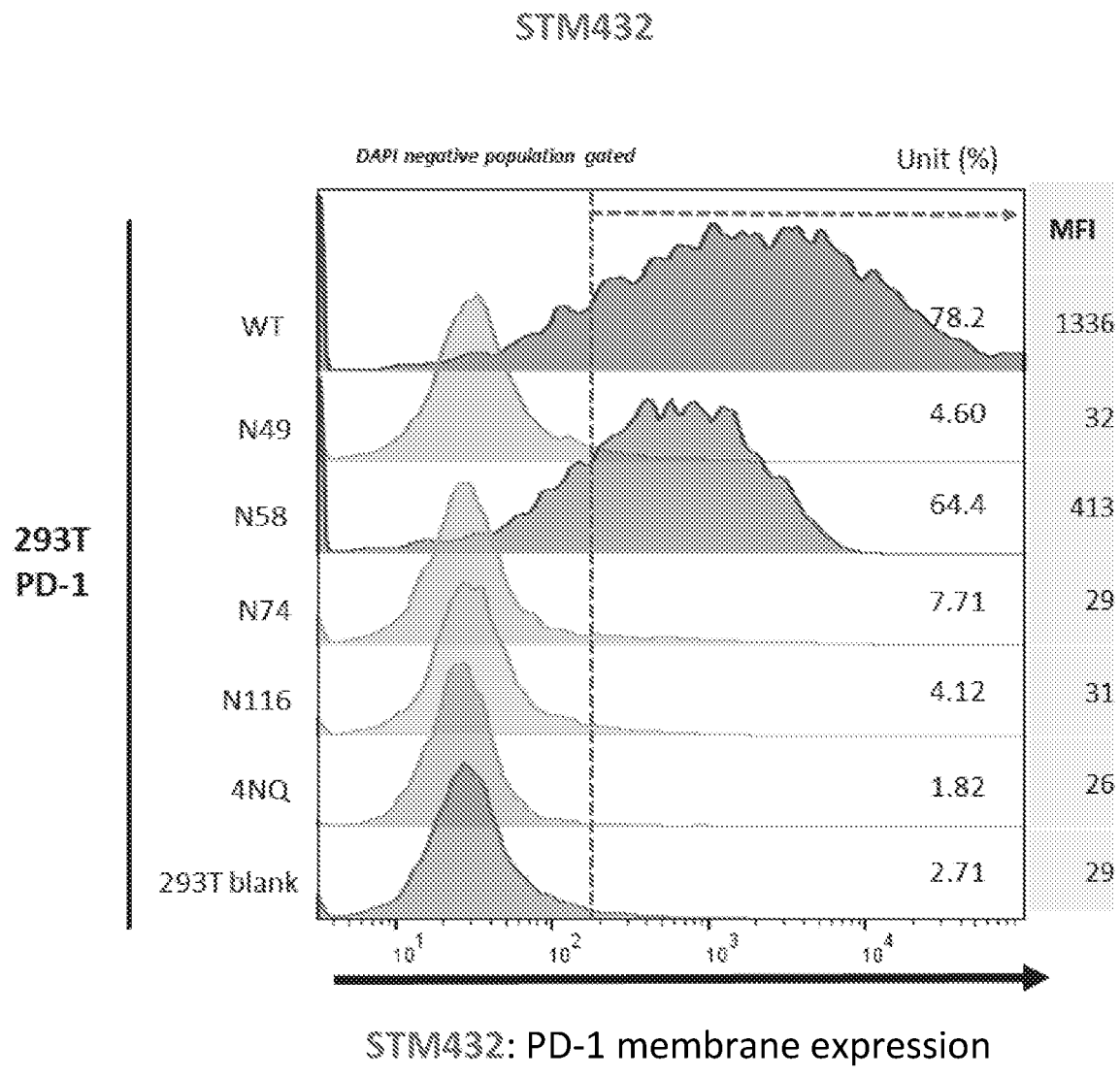
Figure 3C:
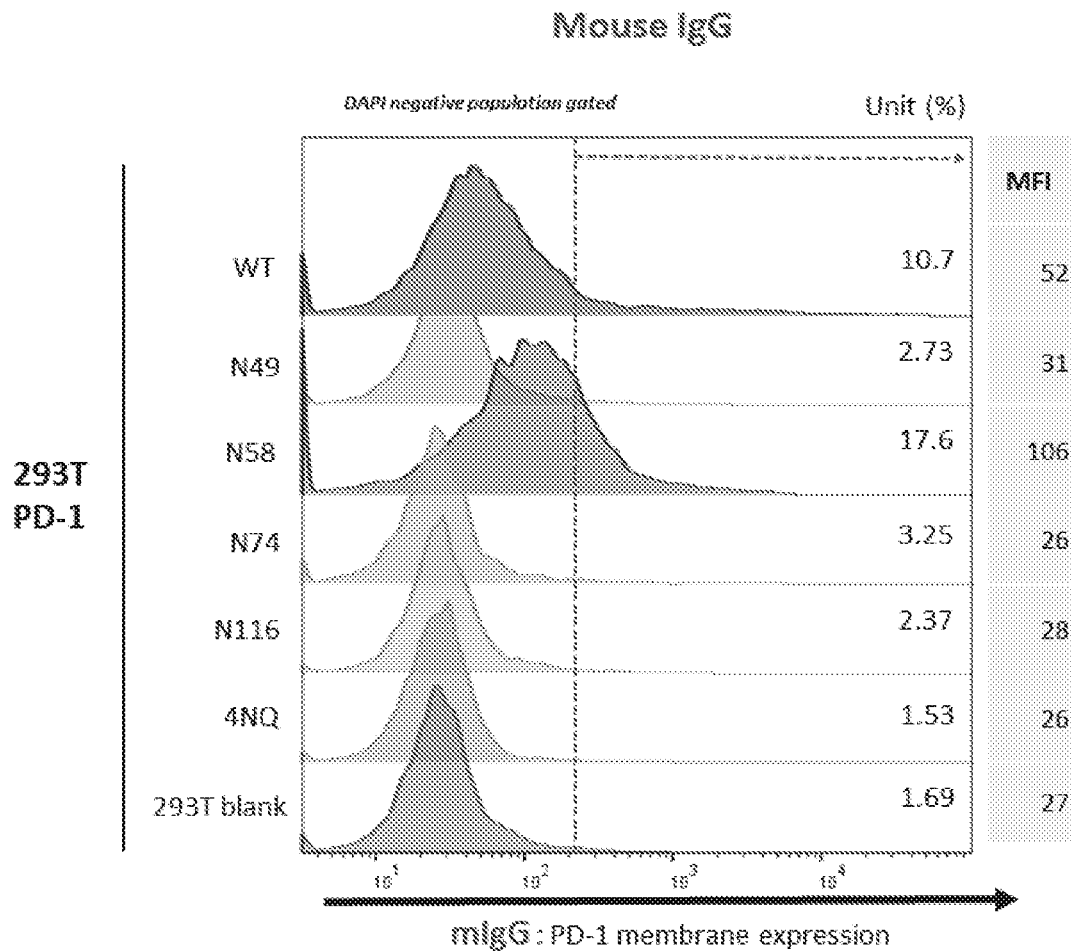

FIGS. 3A-3C. Binding of labeled anti-glycPD-1 and control antibodies to 293T cells expressing wild type and mutant PD-1 proteins—N49, having a Q substituted for N at position 49 of PD-1 (SEQ ID NO:1), N58, having a Q substituted for N at position 58, N 74, having a Q substituted for N at position 74, N116, having a Q substituted for N at position 116, and 4NQ, having Q substituted for N at each of positions 49, 58, 74, and 116, or control 293T cells is measured using flow cytometry. A. Binding of the anti-glycPD-1 antibody STM418 to the 293T cells expressing the wild type and mutant PD-1 proteins and control 293T cells. B. Binding of the anti-glycPD-1 antibody STM432 to the 293T cells expressing the wild type and mutant PD-1 proteins and control 293T cells. C. Binding of control mouse IgG to the 293T cells expressing the wild type and mutant PD-1 proteins and control 293T cells.

Figure 4A:
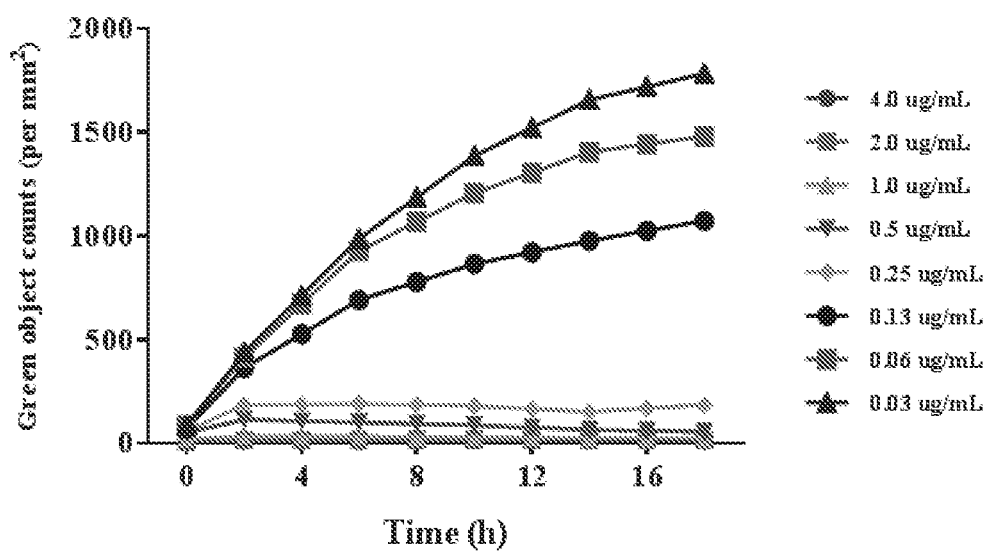
Figure 4B:
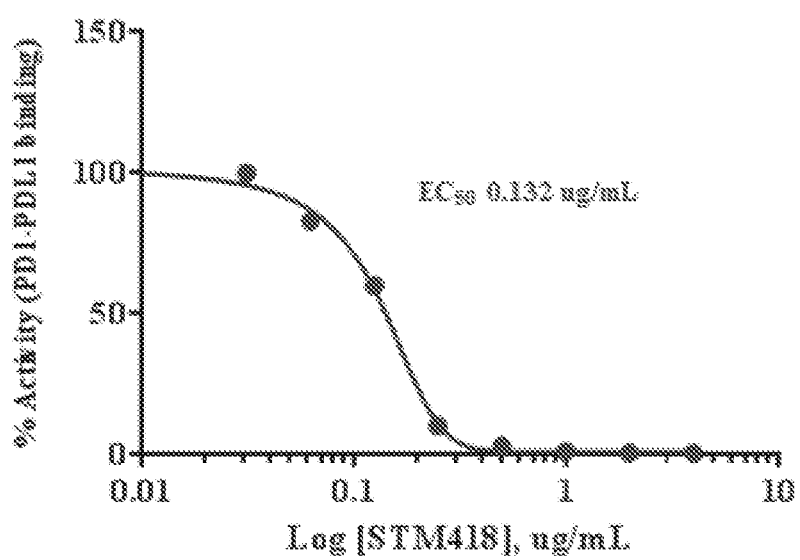

FIGS. 4A and 4B. Neutralizing activity and $EC_{50}$ of anti-glycPD-1 antibody STM418. A. Activity of STM418 to block binding of PD-L1-Fc protein to cells expressing PD-1 by antibody concentration. B. Inhibition of PD-1-PD-L1 binding as a function of STM418 concentration. $EC_{50}$ is 0.132 µg/ml.

Figure 5A:
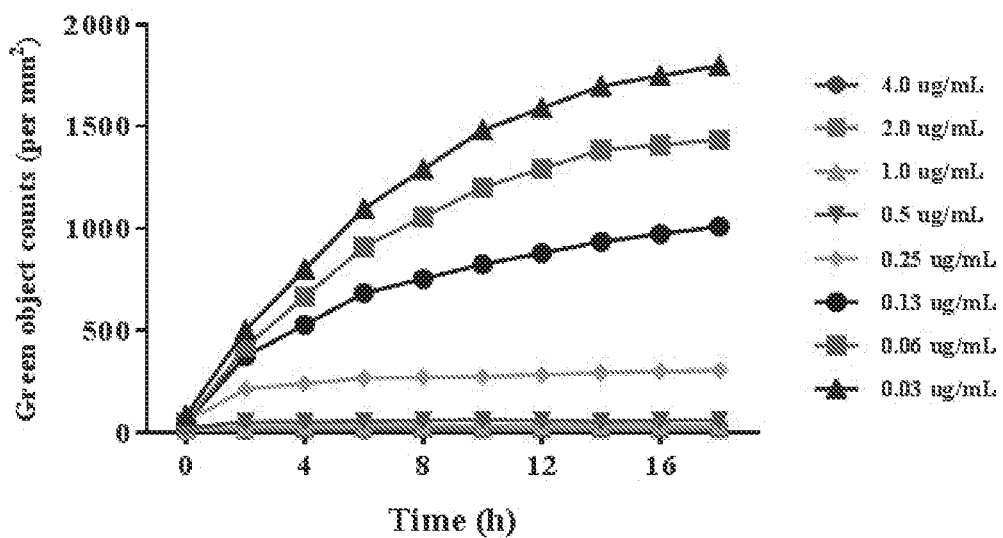
Figure 5B:
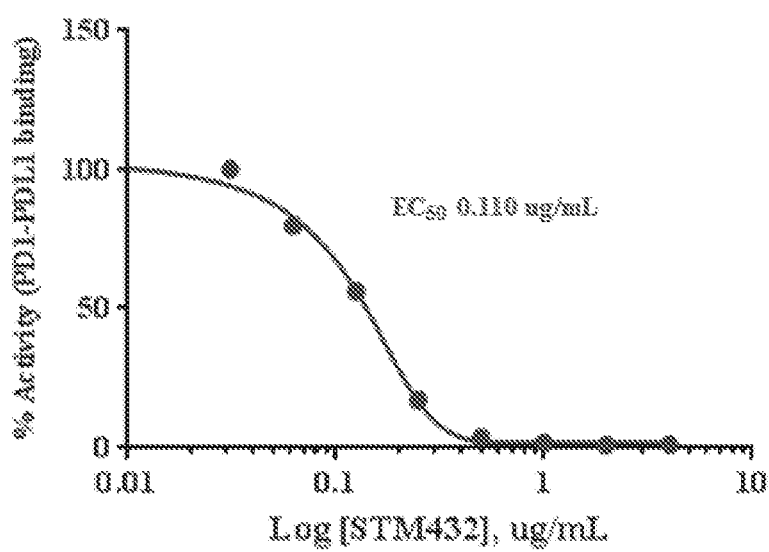

FIGS. 5A and 5B. Neutralizing activity and $EC_{50}$ of anti-glycPD-1 antibody STM432. A. Activity of STM432 to block binding of PD-L1-Fc protein to cells expressing PD-1 by antibody concentration. B. Inhibition of PD-1-PD-L1 binding as a function of STM432 concentration. $EC_{50}$ is 0.110 µg/ml.

Figure 6:
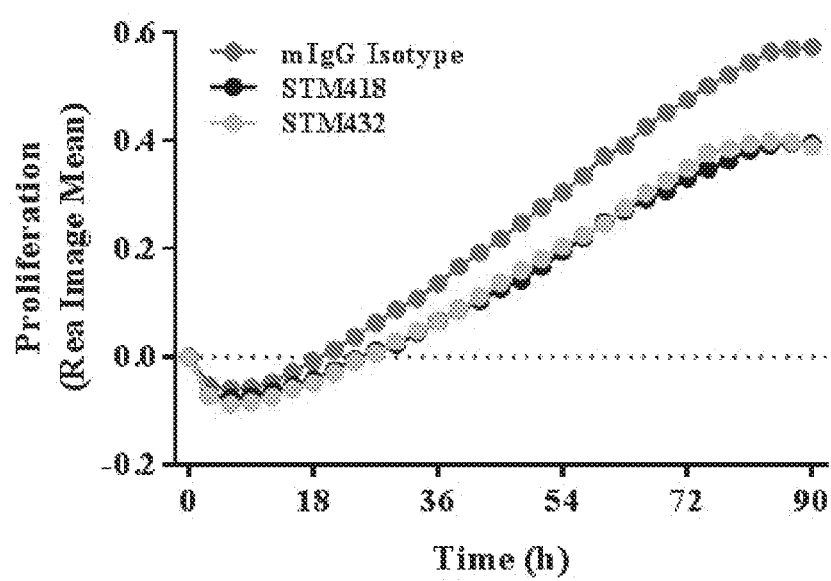

FIG. 6. Effect of STM418 and STM432 on T cell killing of cancer cells. Graph shows cancer cell proliferation, as level of red image detected cancer cells, in the presence of STM418 and STM432 antibodies and control murine IgG.

DETAILED DESCRIPTION

N-glycosylation is a posttranslational modification that is initiated in the endoplasmic reticulum (ER) and subsequently processed in the Golgi (Schwarz & Aebi, *Current Opinion in Structural Biology* 21, 576-582(2011)). This type of modification is first catalyzed by a membrane-associated oligosaccharyl transferase (OST) complex that transfers a preformed glycan composed of oligosaccharides to an asparagine (Asn) side-chain acceptor located within the NXT motif (-Asn-X-Ser/Thr-) (Cheung and Reithmeier, *Methods* 41(4): 451-59 (2007); Helenius and Aebi, *Science* 291 (5512): 2364-69 (2001)). The addition or removal of saccharides from the preformed glycan is mediated by a group of glycotransferases and glycosidases, respectively, which tightly regulate the N-glycosylation cascade in a cell- and location-dependent manner.

Extracellular interaction between programmed death ligand-1 (PD-L1) and programmed death (PD-1) has marked impact on tumor-associated immune escape. Despite the clinical success of immune checkpoint blockade using anti-PD-1 or PD-L1 antibody, the underlying regulatory mechanisms of PD-L1 and PD-1 interaction remain largely unknown. N-linked glycosylation of PD-1 can enhance its binding to PD-L1, resulting in the suppression of T cell-mediated immune response. Accordingly, anti-glycPD-1 antibodies can exhibit enhanced inhibitory effect relative to more general PD-1 antibodies.

As used herein, and unless otherwise specified, the term "programmed death-1" or "PD-1" refers to PD-1 from any vertebrate source, including mammals such as primates (e.g., humans, cynomolgus monkey (cyno)), dogs, and rodents (e.g., mice and rats). Unless otherwise specified, PD-1 also includes various PD-1 isoforms, related PD-1 polypeptides, including SNP variants thereof, as well as different modified forms of PD-1, including but not limited to phosphorylated PD-1, glycosylated PD-1, and ubiquitinated PD-1.

An exemplary amino acid sequence of human PD-1 is provided below, in which the sites for N-linked glycosylation are bolded and underlined (N49, N58, N74 or N116):

```
                                          (SEQ ID NO: 1)
MQIPQAPWPV VWAVLQLGWR PGWFLDSPDR PWNPPTFSPA

LLVVTEGDNA TFTCSFSNTS ESFVLNWYRM SPSNQTDKLA

AFPEDRSQPG QDCRFRVTQL PNGRDFHMSV VRARRNDSGT

YLCGAISLAP KAQIKESLRA ELRVTERRAE VPTAHPSPSP

RPAGQFQTLV VGVVGGLLGS LVLLVWVLAV ICSRAARGTI

GARRTGQPLK EDPSAVPVFS VDYGELDFQW REKTPEPPVP

CVPEQTEYAT IVFPSGMGTS SPARRGSADG PRSAQPLRPE

DGHCSWPL
```

| Feature key | Position(s) | Length | Description |
|---|---|---|---|
| Topological domain | 21-170 | 150 | Extracellular |
| Transmembrane | 171-191 | 21 | Helical |
| Topological domain | 192-288 | 97 | Cytoplasmic |

As shown in Table 1 below, all four N-glycosylation sites are located in the extracellular domain of PD1.

The specific glycosylation sites of a particular PD-1 isoform or variant can vary from amino acids at position 49, 58, 74 or 116 of that particular PD-1 isoform or variant.

In those circumstances, a person of ordinary skill in the art would be able to determine the glycosylation sites of any particular PD-1 isoform or variant that corresponding to N49, N58, N74 and N116 of the human PD-1 exemplified above based on sequence alignment and other common knowledge in the art. As such, provided herein are also antibodies that selectively bind to a glycosylated form of a PD-1 isoform or variant relative to the unglycosylated PD-1 isoform or variant. The glycosylated sites of a PD-1 isoform or variant can be the corresponding sites of N49, N58, N74 and N116 of human PD-1 sequence as provided above.

Provided herein are also polypeptides comprising a fragment of at least 7 (e.g., at least 8, 9, 10, 11, 12, 13, 14, 15, 16, 17, 18, 19, 20 or more) contiguous amino acids of a PD-1 isoform or variant comprising at least one amino acid corresponding to position N49, N58, N74 or N116 of the exemplary human PD-1 sequence as provided above.

As used herein, and unless otherwise specified, the articles "a," "an," and "the" refer to one or to more than one of the grammatical object of the article. By way of example, an antibody refers to one antibody or more than one antibodies.

As used herein, and unless otherwise specified, the term "or" is used interchangeably with "and/or" unless explicitly indicated to refer to alternatives only or the alternatives are mutually exclusive. As used herein, and unless otherwise specified, "another" refers to at least a second or more.

As used herein, and unless otherwise specified, the term "about" indicates that a value includes the inherent variation of error for the device, the method being employed to determine the value, or the variation that exists among the study subjects.

As used herein, and unless otherwise specified, the term "antibody" refers to a polypeptide product of B cells within the immunoglobulin (or "Ig") class of polypeptides that is able to bind to a specific molecular antigen, such as IgG, IgM, IgA, IgD, IgE, as well as other molecules having an antigen binding fragment thereof. An antibody can be composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press; Kuby (1997) *Immunology*, Third Edition, W.H. Freeman and Company, New York). Here, the specific molecular antigen includes the glycosylated human PD-1. Antibodies provided herein include, but are not limited to, polyclonal antibodies, monoclonal antibodies, synthetic antibodies, recombinantly produced antibodies, bi-specific antibodies, multispecific antibodies, human antibodies, humanized antibodies, camelized antibodies, chimeric antibodies, intrabodies, anti-idiotypic (anti-Id) antibodies.

As used herein, and unless otherwise specified, the term "isolated" when used in reference to an antibody, antigen binding fragment or polynucleotide means that the referenced molecule is free of at least one component as it is found in nature. The term includes an antibody, antigen binding fragment or polynucleotide that is removed from some or all other components as it is found in its natural environment. Components of an antibody's natural environment include, for example, erythrocytes, leukocytes, thrombocytes, plasma, proteins, nucleic acids, salts and nutrients. Components of an antigen binding fragment's or polynucleotide's natural environment include, for example, lipid membranes, cell organelles, proteins, nucleic acids, salts and nutrients. An antibody, antigen binding fragment or polynucleotide of the invention can also be free or all the way to substantially free from all of these components or any other component of the cells from which it is isolated or recombinantly produced.

As used herein, and unless otherwise specified, the term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane, *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, and unless otherwise specified, the term "human antibody" refers to an antibody that has a human variable region and/or a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. Here, a human antibody can include an antibody that binds to glycosylated human PD-1 and is encoded by a nucleic acid sequence that is a naturally occurring somatic variant of the human germline immunoglobulin nucleic acid sequence.

As used herein, and unless otherwise specified, the term "chimeric antibody" refers to an antibody that a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)).

As used herein, and unless otherwise specified, the term "humanized antibody" refers to chimeric antibodies that include human immunoglobulins (e.g., recipient antibody) in which the native Complementarity Determining Region ("CDR") residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can have residues that are not found in the recipient antibody or in the donor antibody. These modifications are made to further refine antibody performance. A humanized antibody heavy or light chain can have substantially all of at least one or more variable regions, in which all or substantially all of the CDRs correspond to those of a nonhuman immunoglobulin and all or substantially all of the FRs are those of a human immunoglobulin sequence. The humanized antibody can have at least a portion of an immunoglobulin constant region (Fc), typically that of a human immunoglobulin. For further details, see, Jones et al., *Nature*, 321:522-525 (1986); Riechmann et al., *Nature*, 332:323-329 (1988); and Presta, *Curr. Op. Struct. Biol.*, 2:593-596 (1992); Carter et al., *Proc. Natl. Acd. Sci. USA* 89:4285-4289 (1992); and U.S. Pat. Nos. 6,800,738, 6,719,971, 6,639,055, 6,407,213, and 6,054,297.

As used herein, and unless otherwise specified, the term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor, L. D. et al., *Nucl. Acids Res.* 20:6287-6295(1992)) or antibodies prepared, expressed, created or isolated by any other means that involves splicing of immunoglobulin gene sequences to other DNA sequences. Such recombinant antibodies can have variable and constant regions, including those derived from human germline immunoglobulin sequences (see Kabat, E. A. et al. (1991) *Sequences of Proteins of Immunological Interest*, Fifth Edition, U.S. Department of Health and Human Services, NIH Publication No. 91-3242). The recombinant antibodies can also be subjected to in vitro mutagenesis (or, when an animal transgenic for human Ig sequences is used, in vivo somatic mutagenesis) and thus the amino acid sequences of the $V_H$ and $V_L$ regions of the recombinant antibodies can be sequences that, while derived from and related to human germline $V_H$ and $V_L$ sequences, do not naturally exist within the human antibody germline repertoire in vivo.

As used herein, and unless otherwise specified, the term "antigen binding fragment" and similar terms refer to a portion of an antibody which includes the amino acid residues that immunospecifically bind to an antigen and confer on the antibody its specificity and affinity for the antigen. An antigen binding fragment can be referred to as a functional fragment of an antibody. An antigen binding fragment can be monovalent, bivalent, or multivalent.

Molecules having an antigen binding fragment include, for example, an Fd, Fv, Fab, F(ab'), F(ab)$_2$, F(ab')$_2$, F(ab)$_3$, F(ab')$_3$, single chain Fv (scFv), diabody, triabody, tetrabody, minibody, or a single domain antibody. A scFv can be monovalent scFv or bivalent scFv. Other molecules having an antigen binding fragment can include, for example, heavy or light chain polypeptides, variable region polypeptides or CDR polypeptides or portions thereof so long as such antigen binding fragments retain binding activity. Such antigen binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Plückthun and Skerra, *Meth. Enzymol.*, 178:497-515 (1989) and in Day, E. D., *Advanced Immunochemistry*, Second Ed., Wiley-Liss, Inc., New York, N.Y. (1990). An antigen binding fragment can be a polypeptide having an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The heavy chain of an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The light chain of an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The variable domain or variable region of an antibody refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) 5$^{th}$ ed. A variable region can be a human variable region.

A CDR refers to one of three hypervariable regions (H1, H2 or H3) within the non-framework region of the immunoglobulin (Ig or antibody) $V_H$ β-sheet framework, or one of three hypervariable regions (L1, L2 or L3) within the non-framework region of the antibody $V_L$ β-sheet framework. Accordingly, CDRs are variable region sequences interspersed within the framework region sequences. CDR regions are well known to those skilled in the art and have been defined by, for example, Kabat as the regions of most hypervariability within the antibody variable domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

A universal numbering system has been developed and widely adopted, ImMunoGeneTics (IMGT) Information System® (Lafranc et al., 2003, *Dev. Comp. Immunol.*, 27(1):55-77). IMGT is an integrated information system specializing in immunoglobulins (Ig), T cell receptors (TR) and the major histocompatibility complex (MHC) of human and other vertebrates. Herein, the CDRs are referred to in terms of both the amino acid sequence and the location within the light or heavy chain. As the "location" of the CDRs within the structure of the immunoglobulin V domain is conserved between species and present in structures called loops, by using numbering systems that align variable domain sequences according to structural features, CDR and framework residues and are readily identified. This information can be used in grafting and in the replacement of CDR residues from immunoglobulins of one species into an acceptor framework from, typically, a human antibody. An additional numbering system (AHon) has been developed by Honegger et al., 2001, *J. Mol. Biol.*, 309: 657-670. Correspondence between the numbering system, including, for example, the Kabat numbering and the IMGT unique numbering system, is well known to one skilled in the art (see, e.g., Kabat, Id; Chothia et al., Id.; Martin, 2010, *Antibody Engineering*, Vol. 2, Chapter 3, Springer Verlag; and Lefranc et al., 1999, *Nuc. Acids Res.*, 27:209-212).

CDR region sequences have also been defined by AbM and Contact methodologies. The AbM hypervariable regions represent a compromise between the Kabat CDRs and Chothia structural loops, and are used by Oxford Molecular's AbM antibody modeling software (see, e.g., Martin, 2010, *Antibody Engineering*, Vol. 2, Chapter 3, Springer Verlag). The "contact" hypervariable regions are based on an analysis of the available complex crystal structures. The residues from each of these hypervariable regions or CDRs are noted below.

Exemplary delineations of CDR region sequences are illustrated in Table 2 below. The positions of CDRs within a canonical antibody variable region have been determined by comparison of numerous structures (Al-Lazikani et al., 1997, *J. Mol. Biol.*, 273:927-948); Morea et al., 2000, *Methods*, 20:267-279). Because the number of residues within a hypervariable region varies in different antibodies, additional residues relative to the canonical positions are conventionally numbered with a, b, c and so forth next to the residue number in the canonical variable region numbering scheme (Al-Lazikani et al., Id). Such nomenclature is similarly well known to those skilled in the art.

TABLE 2

EXEMPLARY DELINEATIONS OF CDR REGION SEQUENCES

|  | IMGT | Kabat | AbM | Chothia | Contact |
|---|---|---|---|---|---|
| $V_H$ CDR1 | 27-38 | 31-35 | 26-35 | 26-32 | 30-35 |
| $V_H$ CDR2 | 56-65 | 50-65 | 50-58 | 53-55 | 47-58 |
| $V_H$ CDR3 | 105-117 | 95-102 | 95-102 | 96-101 | 93-101 |
| $V_L$ CDR1 | 27-38 | 24-34 | 24-34 | 26-32 | 30-36 |
| $V_L$ CDR2 | 56-65 | 50-56 | 50-56 | 50-52 | 46-55 |
| $V_L$ CDR3 | 105-117 | 89-97 | 89-97 | 91-96 | 89-96 |

One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest.

As used herein and unless otherwise specified, the term "bind" or "binding" refers to an interaction between molecules. Interactions can be, for example, non-covalent interactions including hydrogen bonds, ionic bonds, hydrophobic interactions, and/or van der Waals interactions. The strength of the total non-covalent interactions between an antibody and a single epitope of a target molecule, such as glycosylated human PD-1, is the affinity of the antibody for that epitope. "Binding affinity" generally refers to the strength of the sum total of noncovalent interactions between a single binding site of a molecule (e.g., a binding protein such as an antibody) and its binding partner (e.g., an antigen).

The affinity of a binding molecule X, such as an antibody, for its binding partner Y, such as the antibody's cognate antigen can generally be represented by the dissociation constant ($K_d$) or equilibrium dissociation constant ($K_D$). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. The "$K_D$" or "$K_D$ value" can be measured by assays known in the art, for example by a binding assay. The $K_D$ can be measured in a radiolabeled antigen binding assay (RIA), for example, performed with the Fab version of an antibody of interest and its antigen (Chen, et al., (1999) *J. Mol. Biol.* 293:865-881). The $K_D$ or $K_D$ value can also be measured by using surface plasmon resonance assays by Biacore, using, for example, a BIAcore™-2000 or a BIAcore™-3000 BIAcore, Inc., Piscataway, N.J.), or by biolayer interferometry using, for example, the OctetQK384 system (ForteBio, Menlo Park, Calif.). As used herein, and unless otherwise specified, an antibody that is said to be able to "selectively bind" a first molecular antigen relative to a second molecular antigen if the antibody binds to the first molecular antigen with higher affinity than the second molecular antigen. An antibody in general does not bind to a totally unrelated antigen.

As used herein, and unless otherwise specified, the term "polypeptide," as used herein, includes an oligopeptide having between 2 and 30 amino acids (e.g., 2, 3, 4, 5, 6, 7, 8, 9, 10, 12, 14, 16, 18, 20, 25 or 30 amino acids) as well as longer amino acid chains, for example, more than 30 amino acids, more than 50 amino acids, more than 100 amino acids, more than 150 amino acids, more than 200 amino acids, more than 300 amino acids, more than 400 amino acids, more than 500 amino acids, or more than 600 amino acids. A polypeptide can be produced, for example, recombinant expression, or by chemical synthesis. The polypeptide of this disclosure can be posttranslationally or chemically modified (e.g., glycosylation, carbamylation, phosphorylation, biotinylation, attachment of fluorescent dyes, and the like). A polypeptide can be glycosylated at specific sites. A polypeptide can include unnatural amino acids that are not encoded by the natural genetic code. For example, a polypeptide can include methylated backbone structures, peptoid backbone structures (poly-N-substituted glycines), L-amino acids, R-amino acids, and the like. A polypeptide can have a wild-type sequence, naturally occurring variant sequence, mutant sequences (e.g., point mutants, deletion mutants), and the like.

Anti-glycPD-1 Antibodies

Provided herein are isolated antibodies that selectively binds to glycosylated PD-1 relative to unglycosylated PD-1. The PD-1 can be human PD-1. The glycosylated PD-1 can be a specific N-glycan structure of PD-1 or a glycopeptide of PD-1. In some embodiments, the antibodies provided herein are antigen binding fragments that selectively bind to glycosylated PD-1 relative to unglycosylated PD-1.

In some embodiments, the isolated antibodies provided herein selectively bind to human PD-1 glycosylated at N49, N58, N74, N116, or any combination thereof, relative to unglycosylated PD-1. In some embodiments, the isolated antibodies selectively bind to human PD-1 that has N49 glycosylation. In some embodiments, the isolated antibodies selectively bind to human PD-1 that has N58 glycosylation. In some embodiments, the isolated antibodies selectively bind to human PD-1 that has N74 glycosylation. In some embodiments, the isolated antibodies selectively bind to human PD-1 that has N116 glycosylation. In some embodiments, the isolated antibodies selectively bind to human PD-1 that has N49 and N58 glycosylation. In some embodiments, the isolated antibodies selectively bind to human PD-1 that has N49 and N74 glycosylation. In some embodiments, the isolated antibodies selectively bind to human PD-1 that has N49 and N116 glycosylation. In some embodiments, the isolated antibodies selectively bind to human PD-1 that has N58 and N74 glycosylation. In some embodiments, the isolated antibodies selectively bind to human PD-1 that has N58 and N116 glycosylation. In some embodiments, the isolated antibodies selectively bind to human PD-1 that has N74 and N116 glycosylation. In some embodiments, the isolated antibodies selectively bind to human PD-1 that has N49, N58 and N74 glycosylation. In some embodiments, the isolated antibodies selectively bind to human PD-1 that has N49, N58 and N116 glycosylation. In some embodiments, the isolated antibodies selectively bind to human PD-1 that has N49, N74 and N116 glycosylation. In some embodiments, the isolated antibodies selectively bind to human PD-1 that has N58, N74, and N116 glycosylation. In some embodiments, the isolated antibodies selectively bind to human PD-1 that has PD-1 has N49, N58, N74, and N116 glycosylation.

In certain aspects, the anti-glycPD-1 antibodies bind to PD-1 and mask or screen one or more glycosylation motifs to block binding or other interation of a molecule with that motif and can block glycosylation of PD-1 at that glycosylation site. In specific embodiments, the anti-glycPD-1 antibody masks the glycosylation site at one or more of N49, N58, N74 and N116.

In some embodiments, the antibodies provided herein selectively bind to one or more glycosylation motifs of PD-1. In some embodiments, the antibodies selectively bind to a glycopeptide having a glycosylation motif and the adjacent peptide. In some embodiments, the antibodies selectively bind to glycosylated PD-1 with $K_d$ less than at least 30%, 40%, 50%, 60%, 70%, 80%, or 90% of the $K_d$ exhibited relative to unglycosylated PD-1. In certain embodiments, the antigen binding fragment binds to glycosylated PD-1 with $K_d$ less than 50% of the $K_d$ exhibited relative to unglycosylated PD-1. In some embodiments, the antibodies bind to glycosylated PD-1 with $K_d$ that is less than 1%, 2%, 3%, 4%, 5%, 6%, 7%, 8%, 9%, 10%, 15%, 20%, 30%, 40%, 50% of the $K_d$ exhibited relative to unglycosylated PD-1. In further aspects, the antibodies bind to glycosylated PD-1 with $K_d$ at least 10 times less than the $K_d$ exhibited relative to unglycosylated PD-1.

Provided are monoclonal antibodies that preferentially bind glycosylated PD-1, particularly, STM418 and STM432, described herein. Also provided are humanized and chimeric forms of STM418 and STM432 and antibodies that compete for binding to STM418 and STM432. The heavy and light chain variable domains of STM418 and STM432 are provided in Table 3 below.

Provided in a particular aspect is the anti-glycPD-1 monoclonal antibody STM418, which has heavy and light chain variable domains having amino acid sequences of SEQ ID NOs: 3 and 5, respectively, (mature $V_H$ and $V_L$ region amino acid sequences without any signal sequence), and antigen binding portions thereof, and humanized and chimeric forms thereof. Provided herein are anti-glycPD-1 antibodies that compete for binding to PD-1 with STM418 MAb and/or bind to the same epitope as STM418.

Provided are monoclonal the nucleic acid (DNA) and corresponding amino acid sequences of the heavy and light chain variable (V) domains of the STM418 MAb are shown in Table 3, infra. SEQ ID NOS: 2 and 3 are the nucleotide and amino acid sequences of the STM418 $V_H$ domain and SEQ ID NOS: 4 and 5 are the nucleotide and amino acid sequences of the mature form of the STM418 kappa $V_L$ domain. Table 4 provides the Chothia, AbM, Kabat and Contact heavy and light chain V domain CDRs of STM418.

The epitope of STM418 on glycosylated PD-1 has been determined to be as follows, with the PD-1 positions as in SEQ ID NO.1 and with contact residues, as determined by antigen-antibody cross-linking experiments, indicated by underlining:

$$^{34}PP\underline{T}FS\underline{P}ALLVV^{44}\ldots^{49}NA\underline{TFT}C\underline{S}FSNT^{59}\ldots$$
$$^{104}RDFHM\underline{S}VVRAR\underline{RN}DSGT\underline{Y}LCG^{124}$$

(Amino acids 34 to 44, 49 to 59 and 104 to 124 of SEQ ID NO:1). Accordingly, provided are antibodies that bind an epitope with regions from amino acids 34 to 44, 49 to 59 and 104 to 124 of the glycosylated PD-1 sequence of SEQ ID NO: 1 and, in particular, with contacts at one or more of positions T36, S38, T51, T53, S55, S109, R115, S118 and Y121 of SEQ ID NO: 1. In specific embodiments, provided are antibodies that selectively bind glycosylated PD-1 and have binding contacts with all of positions 36, 38, 51, 53, 55, 109, 115, 118, and 121 of SEQ ID NO: 1.

In an embodiment, the anti-glycPD-1 antibody that specifically and preferentially binds glycosylated PD-1 comprises a $V_H$ domain having an amino acid sequence of SEQ ID NO: 3 and/or a $V_L$ domain having an amino acid sequence of SEQ ID NO: 5. In an embodiment, the anti-glycPD-1 antibody competes for specific binding to glycosylated PD-1 with an antibody comprising a $V_H$ domain of SEQ ID NO: 3 and a $V_L$ domain of SEQ ID NO: 5. In other embodiments, the anti-glycPD-1 antibody comprises a $V_H$ domain that is at least 80%, 85%, 90%, 95%, 96%, 97%, 98% or 99% identical to the amino acid sequence of SEQ ID NO: 3 and/or a $V_L$ domain that is at least 80%, 85%, 90%, 95%, 96%, 97%, 98% or 99% identical to the amino acid sequence of SEQ ID NO: 5. These anti-glycPD-1 antibodies may be chimeric antibodies and comprise a human constant domain, for example, from a human IgG1, IgG2, IgG3 or IgG4.

In an embodiment, the anti-glycPD-1 antibody that specifically and preferentially binds glycosylated PD-1 comprises a $V_H$ domain comprising Chothia CDRs1-3 having amino acid sequences of SEQ ID NO: 6, SEQ ID NO: 7, and SEQ ID NO: 8, respectively; comprising AbM CDRs 1-3 having amino acid sequences of SEQ ID NO: 9, SEQ ID NO: 10, and SEQ ID NO: 8, respectively; comprising Kabat CDRs 1-3 having amino acid sequences of SEQ ID NO: 11, SEQ ID NO: 12, and SEQ ID NO: 8, respectively; or comprising Contact CDRs 1-3 having amino acid sequences of SEQ ID NO: 13, SEQ ID NO: 14, and SEQ ID NO: 15, respectively, or a combination thereof. In an embodiment, the anti-glycPD-1 antibody competes for specific binding to glycosylated PD-1 with an antibody comprising a $V_H$ domain comprising Chothia CDRs1-3 having amino acid sequences of SEQ ID NO: 6, SEQ ID NO: 7, and SEQ ID NO: 8, respectively; comprising AbM CDRs 1-3 having amino acid sequences of SEQ ID NO: 9, SEQ ID NO: 10, and SEQ ID NO: 8, respectively; comprising Kabat CDRs 1-3 having amino acid sequences of SEQ ID NO: 11, SEQ ID NO: 12, and SEQ ID NO: 8, respectively; or comprising Contact CDRs 1-3 having amino acid sequences of SEQ ID NO: 13, SEQ ID NO: 14, and SEQ ID NO: 15, respectively, or a combination thereof. In an embodiment, the anti-glycPD-1 antibody that specifically and preferentially binds glycosylated PD-1 comprises a $V_L$ domain comprising Chothia, AbM or Kabat CDRs1-3 having amino acid sequences of SEQ ID NO: 16, SEQ ID NO: 17, and SEQ ID NO: 18, respectively; or comprising Contact CDRs 1-3 having amino acid sequences of SEQ ID NO: 19, SEQ ID NO: 20, and SEQ ID NO: 21, respectively, or a combination thereof. In an embodiment, the anti-glycPD-1 antibody competes for specific binding to glycosylated PD-1 with an antibody comprising a $V_L$ domain comprising Chothia, AbM or Kabat CDRs1-3 having amino acid sequences of SEQ ID NO: 16, SEQ ID NO: 17, and SEQ ID NO: 18, respectively; or comprising Contact CDRs 1-3 having amino acid sequences of SEQ ID NO: 19, SEQ ID NO: 20, and SEQ ID NO: 21, respectively, or a combination thereof. In an embodiment, the anti-glycPD-1 antibody comprises or competes for binding to an antibody that comprises a $V_H$ domain comprising Chothia CDRs1-3 having amino acid sequences of SEQ ID NO: 6, SEQ ID NO: 7, and SEQ ID NO: 8, respectively; comprising AbM CDRs 1-3 having amino acid sequences of SEQ ID NO: 9, SEQ ID NO: 10, and SEQ ID NO: 8, respectively; comprising Kabat CDRs 1-3 having amino acid sequences of SEQ ID NO: 11, SEQ ID NO: 12, and SEQ ID NO: 8, respectively; or comprising Contact CDRs 1-3 having amino acid sequences of SEQ ID NO: 13, SEQ ID NO: 14, and SEQ ID NO: 15, respectively, and comprises a $V_L$ domain comprising Chothia, AbM or Kabat CDRs1-3 having amino acid sequences of SEQ ID NO: 16, SEQ ID NO: 17, and SEQ ID NO: 18, respectively; or comprising Contact CDRs 1-3 having amino acid sequences of SEQ ID NO: 19, SEQ ID NO: 20, and SEQ ID NO: 21, respectively. Preferably, the $V_H$ and $V_L$ domains have the same class of CDR, i.e., both have Chothia, AbM, Kabat or Contact CDRs.

In other embodiments, the anti-glycPD-1 antibody has a $V_H$ domain comprising CDRs H1, H2 and H3 with amino acid sequences that have 1, 2, 3, 4, or 5 amino acid substitutions in 1, 2 or 3 of the CDRs having the amino acid sequences of SEQ ID NO: 6, SEQ ID NO: 7, and SEQ ID NO: 8, respectively, or of the CDRs having the amino acid sequences of SEQ ID NO: 9, SEQ ID NO: 10, and SEQ ID NO: 8, respectively, or of the CDRs having the amino acid sequences of SEQ ID NO: 11, SEQ ID NO: 12, and SEQ ID NO: 8, respectively, or of the CDRs having the amino acid sequences of SEQ ID NO: 13, SEQ ID NO: 14, and SEQ ID NO: 15, respectively. The anti-glycPD-1 antibody may have a V_L domain comprising CDRs L1, L2 and L3 with amino acid sequences that have 1, 2, 3, 4, or 5 amino acid substitutions in 1, 2 or 3 CDRs having the amino acid sequences of SEQ ID NO: 16, SEQ ID NO: 17, and SEQ ID NO: 18, respectively, or CDRs having the amino acid sequences of SEQ ID NO: 19, SEQ ID NO: 20, and SEQ ID NO: 21, respectively. The anti-glycPD-1 antibody may have amino acid substitutions in CDRs for both the $V_H$ and $V_L$ domains. In some embodiments, the amino acid substitutions are conservative substitutions.

Preferably the foregoing antibodies have human framework regions, i.e., are humanized forms of STM418, and optionally, comprise a human constant domain, for example, from a human IgG1, IgG2, IgG3 or IgG4.

It will be appreciated by those skilled in the art that one or more amino acid substitutions may be made in the CDRs and/or framework regions of a humanized antibody to improve binding affinity or other parameter. In embodiments, the anti-glycPD-1 antibody competes for specific binding to glycosylated PD-1 with an antibody comprising the above-described $V_H$ and $V_L$ domains and the CDRs therein. In embodiments, the anti-glycPD-1 antibody binds to glycosylated PD-1 with a $K_d$ less than half of the $K_d$ exhibited by the antibody's binding to unglycosylated PD-1. In an embodiment, the anti-glycPD-1 antibody binds to glycosylated PD-1 protein with a $K_d$ at least 5 times less than the $K_d$ exhibited relative to unglycosylated PD-1. In an embodiment, the anti-glycPD-1 antibody binds to glycosylated PD-1 protein with a $K_d$ at least 10 times less than the $K_d$ exhibited by the antibody's binding to unglycosylated PD-1 protein. In an embodiment, in a cell flow cytometry binding assay as described in Example 2, the antibody exhibits binding as expressed as MFI to cells expressing WT PD-1 that is 5 times, 10 times, 20 times, 30 times, 50 times, 70 times or 100 times greater than the MFI for binding to cells expressing unglycosylated PD-1. In an embodiment, the antibody is directly or indirectly detectable by a fluorescent label or marker. In an embodiment, the antibody is directly labeled with a fluorescent label or marker, such as FITC. In an embodiment, the binding affinity of STM418 MAb, or chimeric or humanized form thereof, for glycosylated PD-1 is from 5-20 nM or from 5-10 nM inclusive of the lower and upper values. In an embodiment, the antibody inhibits the interaction of PD-1 with PD-L1, and particularly inhibits the interaction of glycosylated PD-1 expressed by effector T-cells with PD-L1 expressed by tumor cells.

Provided in another particular aspect is the anti-glycPD-1 monoclonal antibody STM432 which has heavy and light chain variable domains having amino acid sequences of SEQ ID NOs: 23 and 25, respectively, (mature $V_H$ and $V_L$ region amino acid sequences), and antigen binding portions thereof, and humanized and chimeric forms thereof, that specifically bind glycosylated PD-1. The nucleic acid sequences encoding the heavy and light chain variable (V) domains of the STM432 MAb, SEQ ID NOS: 22 and 24, respectively, are shown in Table 3 infra. Also shown in Table 5 are the Chothia, AbM, Kabat and Contact heavy and light chain V domain CDRs of STM432.

STM432 has been determined to bind an epitope on glycosylated PD-1 corresponding to the sequence $^{91}$DCRFRVTQLPNGRDFHM$^{107}$ ... $^{123}$CGAISLAPKAQI$^{134}$ (amino acids D91 to M107 and C123 to I134 of the PD-1 amino acid sequence of SEQ ID NO: 1. As shown herein, the amino acid residues R95, R103, S127, and K131, which comprise the epitope recognized by MAb STM432, i.e., are contacted by the mAb bound to PD-1, are underlined. Accordingly, provided are anti-glycPD-1 antibodies that bind the STM432 epitope as defined herein. Also provided are anti-glycPD-1 antibodies that compete for binding to glycosylated PD-1 with STM432 MAb and/or bind to the same epitope as STM432.

In an embodiment, the anti-glycPD-1 antibody that specifically and preferentially binds glycosylated PD-1 comprises a $V_H$ domain having the amino acid sequence of SEQ ID NO: 23 and/or a $V_L$ domain having the amino acid sequence of SEQ ID NO: 25. In an embodiment, the anti-glycPD-1 antibody competes for specific binding to glycosylated PD-1 with an antibody comprising a $V_H$ domain of SEQ ID NO: 23 and a $V_L$ domain of SEQ ID NO: 25. In an embodiment, the anti-glycPD-1 antibody that specifically and preferentially binds glycosylated PD-1 comprises a $V_H$ domain that is at least 80%, 85%, 90%, 95%, 96%, 97%, 98% or 99% identical to the amino acid sequence of SEQ ID NO: 23 and/or a $V_L$ domain that is at least 80%, 85%, 90%, 95%, 96%, 97%, 98% or 99% identical to the amino acid sequence of SEQ ID NO: 25. These anti-glycPD-1 antibodies may be chimeric antibodies and comprise a human constant domain, for example, from a human IgG1, IgG2, IgG3 or IgG4.

In an embodiment, the anti-glycPD-1 antibody that specifically and preferentially binds glycosylated PD-1 comprises a $V_H$ domain comprising Chothia CDRs 1-3 having amino acid sequences of SEQ ID NO: 26, SEQ ID NO: 27, and SEQ ID NO: 28, respectively; AbM CDRs 1-3 having amino acid sequences of SEQ ID NO: 29, SEQ ID NO: 30, and SEQ ID NO: 28, respectively; Kabat CDRs 1-3 having amino acid sequences of SEQ ID NO: 31, SEQ ID NO: 32, and SEQ ID NO: 28, respectively; or Contact CDRs 1-3 having amino acid sequences of SEQ ID NO: 33, SEQ ID NO: 34, and SEQ ID NO: 35, respectively, or a combination thereof. In an embodiment, the anti-glycPD-1 antibody competes for specific binding to glycosylated PD-1 with an antibody comprising a $V_H$ domain comprising Chothia CDRs 1-3 having amino acid sequences of SEQ ID NO: 26, SEQ ID NO: 27, and SEQ ID NO: 28, respectively; AbM CDRs 1-3 having amino acid sequences of SEQ ID NO: 29, SEQ ID NO: 30, and SEQ ID NO: 28, respectively, Kabat CDRs 1-3 having amino acid sequences of SEQ ID NO: 31, SEQ ID NO: 32, and SEQ ID NO: 28, respectively; or Contact CDRs 1-3 having amino acid sequences of SEQ ID NO: 33, SEQ ID NO: 34, and SEQ ID NO: 35, respectively, or a combination thereof. In an embodiment, the anti-glycPD-1 antibody that specifically and preferentially binds glycosylated PD-1 comprises a $V_L$ domain comprising Chothia, AbM and Kabat CDRs 1-3 having amino acid sequences of SEQ ID NO: 36, SEQ ID NO: 37, and SEQ ID NO: 38, respectively; or Contact CDRs 1-3 having amino acid sequences of SEQ ID NO: 39, SEQ ID NO: 40, and SEQ ID NO: 41, or a combination thereof. In an embodiment, the anti-glycPD-1 antibody competes for specific binding to glycosylated PD-1 with an antibody comprising a $V_L$ domain comprising Chothia, AbM or Kabat CDRs 1-3 having amino acid sequences of SEQ ID NO: 36, SEQ ID NO: 37, and SEQ ID NO: 38, respectively, or Contact CDRs 1-3 having amino acid sequences of SEQ ID NO: 39, SEQ ID NO: 40, and SEQ ID NO: 41, or a combination thereof. In an embodiment, the anti-glycPD-1 antibody that specifically and preferentially binds glycosylated PD-1 comprises, or competes for binding with an antibody that comprises, a $V_H$ domain comprising Chothia CDRs 1-3 having amino acid sequences of SEQ ID NO: 26, SEQ ID NO: 27, and SEQ ID NO: 28, respectively; AbM CDRs 1-3 having amino acid sequences of SEQ ID NO: 29, SEQ ID NO: 30, and SEQ ID NO: 28, respectively; Kabat CDRs 1-3 having amino acid sequences of SEQ ID NO: 31, SEQ ID NO: 32, and SEQ ID NO: 28, respectively; or Contact CDRs 1-3 having amino acid sequences of SEQ ID NO: 33, SEQ ID NO: 34, and SEQ ID NO: 35, respectively, and comprises a $V_L$ domain comprising Chothia, AbM or Kabat CDRs 1-3 having amino acid sequences of SEQ ID NO: 36, SEQ ID NO: 7, and SEQ ID NO: 38, respectively; or Contact CDRs 1-3 having amino acid sequences of SEQ ID NO: 39, SEQ ID NO: 40, and SEQ ID NO: 41. Preferably, the $V_H$ and $V_L$ domains have the same class of CDR, i.e., both have Chothia, AbM, Kabat or Contact CDRs.

Provided in certain embodiments are anti-glycPD-1 antibodies which have a $V_H$ domain comprising CDRs H1, H2 and H3 with amino acid sequences that have 1, 2, 3, 4, or 5 amino acid substitutions in 1, 2 or 3 CDRs having the amino acid sequences of SEQ ID NO: 26, SEQ ID NO: 27, and SEQ ID NO: 28, respectively; or SEQ ID NO: 29, SEQ ID NO: 30, and SEQ ID NO: 28, respectively; or SEQ ID NO: 31, SEQ ID NO: 32, and SEQ ID NO: 28, respectively; or SEQ ID NO: 33, SEQ ID NO: 34, and SEQ ID NO: 35, respectively. The anti-glycPD-1 antibody also may have a $V_L$ domain comprising CDRs L1, L2 and L3 with amino acid sequences that have 1, 2, 3, 4, or 5 amino acid substitutions in 1, 2 or 3 CDRs having the amino acid sequences of SEQ ID NO: 36, SEQ ID NO: 37, and SEQ ID NO: 38, respectively; or SEQ ID NO: 39, SEQ ID NO: 40, and SEQ ID NO: 41, respectively. The anti-glycPD-1 antibody may have amino acid substitutions in CDRs in both the $V_H$ and $V_L$ domains. In some embodiments, the amino acid substitutions are conservative substitutions.

In embodiments, the anti-glycPD-1 antibody competes for specific binding to glycosylated PD-1 with an antibody comprising the above-described $V_H$ and $V_L$ domains and the CDRs therein. Preferably these antibodies have human framework regions, i.e., are humanized forms of STM432, and optionally, comprise a human constant domain, for example, from a human IgG1, IgG2, IgG3 or IgG4. It will be appreciated by those skilled in the art that one or more amino acid substitutions may be made in the CDRs or framework regions of a humanized antibody to improve binding affinity or other parameter. In embodiments, the anti-glycPD-1 antibody binds to glycosylated PD-1 with a $K_d$ less than half of the $K_d$ exhibited relative to unglycosylated PD-1. In embodiments, the anti-glycPD-1 antibody binds to glycosylated PD-1 with a $K_d$ less than half of the $K_d$ exhibited relative to unglycosylated PD-1. In an embodiment, the anti-glycPD-1 antibody binds to glycosylated PD-1 protein with a $K_d$ at least 5 times less than the $K_d$ exhibited by the antibody's binding to unglycosylated PD-1. In an embodiment, the anti-glycPD-1 antibody binds to glycosylated PD-1 protein with a $K_d$ at least 10 times less than the $K_d$ exhibited by the antibody's binding to unglycosylated PD-1 protein. In an embodiment, in a cell flow cytometry binding assay as described in Example 2, the antibody exhibits binding as expressed as MFI to cells expressing WT PD-1 that is 5 times, 10 times, 20 times, 30 times, 40 times, or 50 times greater than the MFI for binding to cells expressing unglycosylated PD-1. In an embodiment, the antibody is directly or indirectly detectable by a fluorescent label or marker. In an embodiment, the antibody is directly labeled with a fluorescent label or marker such as FITC. In an embodiment, the binding affinity of STM432 MAb, or binding domain or humanized or chimeric form thereof, for glycosylated PD-1 is from 5-20 nM or from 5-10 nM inclusive of the lower and upper values. In an embodiment, the antibody inhibits the interaction of PD-1 with PD-1, and particularly inhibits the interaction of PD-1 expressed by effector T-cells with PD-1, particularly, glycosylated PD-1, expressed by tumor cells.

In an embodiment, the antibody inhibits the interaction of PD-1 with PD-1, and particularly inhibits the interaction of glycosylated PD-1 expressed by effector T-cells with PD-L1 expressed by tumor cells.

Yet another embodiment provides an isolated nucleic acid molecule encoding an anti-glycPD-1 $V_H$ domain comprising a nucleotide sequence that is at least 90-98% identical to SEQ ID NOs: 2 or 22 and/or encoding an anti-glycPD-1 antibody $V_L$ domain comprising a nucleotide sequence that is at least 90-98% identical to SEQ ID NO: 4 or 24, respectively. In embodiments, the nucleotide sequences encoding the $V_H$ and/or the $V_L$ domains are 90%, 91%, 92%, 93%, 94%, 95%, 96%, 97%, 98%, 99%, or more identical to SEQ ID NOs: 2 or 22, or SEQ ID NOs: 4 or 24, respectively.

Table 3 below provides the nucleotide and amino acid sequences of the heavy and light chain variable domains of STM418 and STM432.

TABLE 3

HEAVY AND LIGHT CHAIN VARIABLE DOMAIN NUCLEOTIDE AND AMINO ACID SEQUENCES OF STM418 AND STM432

| Description | Sequence |
| --- | --- |
| MAb STM418 mature heavy chain V domain nucleotide sequence | gaagtgatgctggtggagtctggggggaggcttagtgaagcctggagg gtccctgaaactctcctgtgcagcctctggattcactttcagtagct atggcatgtcttgggttcgtcagactccggagaagaggctggagtgg gtcgcaaccattagtggtggtggtggtaacacctactatccagacac tgtgaagggccgattcaccatctccagagacaatgccaagaacaccc tgtacctgcaaatgagcagtctgaggtctgaggacacggccttgtat tattgtacaagctattactacgggattgactactggggccaaggcac cactctcacagtctcctca (SEQ ID NO: 2) |
| MAb STM418 mature heavy chain V domain amino acid sequence | EVMLVESGGGLVKPGGSLKLSCAASGFTFSSYGMSWVRQTPEKRLEW VATISGGGGNTYYPDTVKGRFTISRDNAKNTLYLQMSSLRSEDTALY YCTSYYYGIDYWGQGTTLTVSS (SEQ ID NO: 3) |
| MAb STM418 mature Kappa light chain V domain nucleotide sequence | gacattgtgatgacccagtctcacaaattcatgtccacatcagtagg agacagggtcagcatcacctgcaaggccagtcaggatgtgagtactg ctgtagcctggtatcaacaaaaaccagggcaatctcctaaattactg atttactgggcatccacccggcaaactggagtccctgatcgcttcac aggcagtggatctgggacagagtatactctcaccatcagcagtgtgc aggctgaagacctggcactttattactgtcagcaacattatagcatt ccgtggacgttcggtggaggcaccaagctggaaatcaaacgg (SEQ ID NO: 4) |

TABLE 3-continued

HEAVY AND LIGHT CHAIN VARIABLE DOMAIN NUCLEOTIDE AND AMINO ACID SEQUENCES OF STM418 AND STM432

| Description | Sequence |
|---|---|
| MAb STM418 mature Kappa light chain V domain amino acid sequence | DIVMTQSHKFMSTSVGDRVSITCKASQDVSTAVAWYQQKPGQSPKLL IYWASTRQTGVPDRFTGSGSGTEYTLTISSVQAEDLALYYCQQHYSI PWTFGGGTKLEIKR (SEQ ID NO: 5) |
| MAb STM432 mature heavy chain V domain nucleotide sequence | gaagtgatgctggtggagcctgggggaggcttagtgaagcctggagggtcc ctgaaactctcctgtgcagcctctggattcactttcagtagctatggcatg tcttgggttcgccagactccggagaagaggctggagtgggtcgcaaccatt agtggtggtggtgctaacacctactatccagacactgtgaaggcccgattc accatctccagagacaatgccaagaacaccctgtacctgcaaatgaacagt ctgaggtctgaggacacggccttgtattactgtgcaagatatggttacgac acggtctttgcttactggggccaagggactctggtcactgtctctgca (SEQ ID NO: 22) |
| MAb STM418 mature heavy chain V domain amino acid sequence | EVMLVEPGGGLVKPGGSLKLSCAASGFTFSSYGMSWVRQTPEKRLEWVATI SGGGANTYYPDTVKGRFTISRDNAKNTLYLQMNSLRSEDTALYYCARYGYD TVFAYWGQGTLVTVSA (SEQ ID NO: 23) |
| MAb STM418 mature kappa light chain V domain nucleotide sequence | gacattgtgctgacccaatctccagcttctttggctgtgtctctagggcag aaggccaccatctcctgcagagccagcgaaagtgttgatgattatggcatt ggttttatgaactggttccaacagaaaccaggtcagccacccaaactcctc atctatactacatccaaccaaggatccggggtccctgccaggtttagtggc agtgggtctgggacagacttcagcctcaacatccatcctatggtggaggat gatactgcaatgtatttctgtcagcaaagtaaggaggttccgtggacgttc ggtggcggcaccaagctggaaatcaaa (SEQ ID NO: 24) |
| MAb STM418 mature heavy chain V domain nucleotide (DNA) sequence | DIVLTQSPASLAVSLGQKATISCRASESVDDYGIGFMNWFQQKPGQPPKLL IYTTSNQGSGVPARFSGSGSGTDFSLNIHPMVEDDTAMYFCQQSKEVPWTF GGGTKLEIK (SEQ ID NO: 25) |

Provided in Tables 4 and 5 below are the CDR sequences of STM418 and STM432 antibodies according to the Chothia, AbM, Kabat, and Contact CDRs. Accordingly, provided are humanized forms of STM418 and STM432 that preferentially bind glycosylated PD-1 as compared to unglycosylated PD-1 that comprise the CDRs of Tables 4 and 5 below engrafted into human framework regions.

TABLE 4

CDR SEQUENCES OF STM418

| | Region Definition | CDR1 | CDR2 | CDR3 |
|---|---|---|---|---|
| STM418 Heavy chain | Chothia | GFTFSSY (SEQ ID NO: 6) | SGGGGN (SEQ ID NO: 7) | YYYGIDY (SEQ ID NO: 8) |
| | AbM | GFTFSSYGMS (SEQ ID NO: 9) | TISGGGGNTY (SEQ ID NO: 10) | YYYGIDY (SEQ ID NO: 8) |
| | Kabat | SYGMS (SEQ ID NO: 11) | TISGGGGNTYYPDTVKG (SEQ ID NO: 12) | YYYGIDY (SEQ ID NO: 8) |
| | Contact | SSYGMS (SEQ ID NO: 13) | WVATISGGGGNTY (SEQ ID NO: 14) | TSYYYGID (SEQ ID NO: 15) |
| STM418 Kappa light chain | Chothia | KASQDVSTAVA (SEQ ID NO: 16) | WASTRQT (SEQ ID NO: 17) | QQHYSIPWT (SEQ ID NO: 18) |
| | AbM | KASQDVSTAVA (SEQ ID NO: 16) | WASTRQT (SEQ ID NO: 17) | QQHYSIPWT (SEQ ID NO: 18) |
| | Kabat | KASQDVSTAVA (SEQ ID NO: 16) | WASTRQT (SEQ ID NO: 17) | QQHYSIPWT (SEQ ID NO: 18) |
| | Contact | STAVAWY (SEQ ID NO: 19) | LLIYWASTRQ (SEQ ID NO: 20) | QQHYSIPW (SEQ ID NO: 21) |

TABLE 5

CDR SEQUENCES OF STM432

| | Region Definition | CDR1 | CDR2 | CDR3 |
|---|---|---|---|---|
| STM432 Heavy chain | Chothia | GFTFSSAY (SEQ ID NO: 26) | SGGGAN (SEQ ID NO: 27) | YGYDTVFAY (SEQ ID NO: 28) |
| | AbM | GFTFSSAYGMS (SEQ ID NO: 29) | TISGGGANTY (SEQ ID NO: 30) | YGYDTVFAY (SEQ ID NO: 28) |
| | Kabat | SYGMS (SEQ ID NO: 31) | TISGGGANTYYPDTVKG (SEQ ID NO: 32) | YGYDTVFAY (SEQ ID NO: 28) |
| | Contact | SSYGMS (SEQ ID NO: 33) | WVATISGGGANTY (SEQ ID NO: 34) | ARYGYDTVFA (SEQ ID NO: 35) |
| STM432 Kappa light chain | Chothia | RASESVDDYGIGFMN (SEQ ID NO: 36) | TTSNQGS (SEQ ID NO: 37) | QQSKEVPWT (SEQ ID NO: 38) |
| | AbM | RASESVDDYGIGFMN (SEQ ID NO: 36) | TTSNQGS SEQ ID NO: 37) | QQSKEVPWT (SEQ ID NO: 38) |
| | Kabat | RASESVDDYGIGFMN (SEQ ID NO: 36) | TTSNQGS SEQ ID NO: 37) | QQSKEVPWT (SEQ ID NO: 38) |
| | Contact | DDYGIGFMNWF (SEQ ID NO: 39) | LLIYTTSNQG (SEQ ID NO: 40) | QQSKEVPW (SEQ ID NO: 41) |

In some embodiments, the anti-glycPD-1 antibodies provided herein can be an IgG, IgM, IgA, IgD, or IgE. The anti-glycPD-1 antibody can also be a chimeric antibody, an affinity matured antibody, a humanized antibody, or a human antibody. The anti-glycPD-1 antibody can also be a camelized antibody, an intrabody, an anti-idiotypic (anti-Id) antibody. In some embodiments, the anti-glycPD-1 antibody can be a polyclonal antibody or monoclonal antibody.

In some embodiments, the antibodies provided herein are antigen binding fragments that selectively binds to glycosylated PD-1 relative to unglycosylated PD-1. The antigen binding fragment can be Fd, Fv, Fab, F(ab'), F(ab)$_2$, F(ab')$_2$, F(ab)$_3$, F(ab')$_3$, single chain Fv (scFv), diabody, triabody, tetrabody, minibody, or a single domain antibody. A scFv can be a monovalent scFv, or a bivalent scFv.

By known means and as described herein, polyclonal or monoclonal antibodies, antigen binding fragments, and binding domains and CDRs (including engineered forms of any of the foregoing) can be created that are specific to glycosylated PD-1, one or more of its respective epitopes, or conjugates of any of the foregoing, whether such antigens or epitopes are isolated from natural sources or are synthetic derivatives or variants of the natural compounds.

Antibodies can be produced from any animal source, including birds and mammals. In some embodiments, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is hereby incorporated by reference in its entirety. These techniques are further described in Marks et al., Bio/Technol., 10:779-783(1992); Stemmer, Nature, 370:389-391(1994); Gram et al., Proc. Natl. Acad. Sci. USA, 89:3576-3580 (1992); Barbas et al., Proc. Natl. Acad. Sci. USA, 91:3809-3813(1994); and Schier et al., Gene, 169(2): 147-155(1996); which are hereby incorporated by reference in their entireties.

Methods for producing polyclonal antibodies in various animal species, as well as for producing monoclonal antibodies of various types, including humanized, chimeric, and fully human, are well known in the art. For example, the following U.S. patents provide enabling descriptions of such methods and are herein incorporated by reference: U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,891,024; 7,407,659; and 8,178,098, which are hereby incorporated by reference in their entireties.

In some embodiments, the anti-glycPD-1 antibodies can be monoclonal antibodies. In some embodiments, the anti-glycPD-1 can be polyclonal antibodies. Animals can be inoculated with an antigen, such as a glycosylated PD-1 polypeptide in order to produce antibodies specific for a glycosylated PD-1 polypeptide. Frequently an antigen is bound or conjugated to another molecule to enhance the immune response. A conjugate can be any peptide, polypeptide, protein, or non-proteinaceous substance bound to an antigen that is used to elicit an immune response in an animal. Antibodies produced in an animal in response to antigen inoculation have a variety of non-identical molecules (polyclonal antibodies) made from a variety of individual antibody producing B lymphocytes. Given the correct conditions for polyclonal antibody production in an animal, most of the antibodies in the animal's serum recognize the collective epitopes on the antigenic compound to which the animal has been immunized.

This specificity can be further enhanced by affinity purification to select only those antibodies that recognize the antigen or epitope of interest. The methods for generating monoclonal antibodies (MAbs) can begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and can provide certain advantages. Mice (e.g., BALB/c mice) are routinely used and generally give a high percentage of stable fusions.

Hybridoma technology involves the fusion of a single B lymphocyte from a mouse previously immunized with a glycosylated PD-1 polypeptide with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) can be produced.

The anti-glycPD-1 antibodies can be produced by any method known in the art useful for the production of polypeptides, e.g., in vitro synthesis, recombinant DNA production, and the like. The humanized antibodies can be produced by recombinant DNA technology. The antibodies described herein can also be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757; which are hereby incorporated by reference in their entireties. Techniques for the recombinant expression of immunoglobulins, including humanized immunoglobulins, can also be found, in Goeddel et al., *Gene Expression Technology Methods in Enzymology* Vol. 185 Academic Press (1991), and Borreback, *Antibody Engineering*, W. H. Freeman (1992); which are hereby incorporated by reference in their entireties. Additional information concerning the generation, design and expression of recombinant antibodies can be found in Mayforth, *Designing Antibodies*, Academic Press, San Diego (1993).

Methods have been developed to replace light and heavy chain constant domains of the monoclonal antibody with analogous domains of human origin, leaving the variable regions of the foreign antibody intact. Alternatively, fully human monoclonal antibodies are produced in mice or rats transgenic for human immunoglobulin genes. Methods have also been developed to convert variable domains of monoclonal antibodies to more human form by recombinantly constructing antibody variable domains having both rodent and human amino acid sequences. In humanized monoclonal antibodies, only the hypervariable CDR is derived from non-human (e.g., mouse, rat, chicken, llama) monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody can also be subject to genetic mutation or other changes, which may or may not alter the binding specificity of antibodies produced by the hybridoma.

Engineered antibodies can be created, by using monoclonal and other antibodies and recombinant DNA technology to produce other antibodies or chimeric molecules that retain the antigen or epitope specificity of the original antibody, i.e., the molecule has binding domain. Such techniques can involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091,513 and 6,881,557, which are incorporated herein by reference.

In certain embodiments, the anti-glycPD-1 antibody is a human antibody. Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a glycosylated PD-1 polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, therapeutically useful IgG, IgA, IgM and IgE antibodies can be produced. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a rat. In one embodiment, an antigen binding sequence is synthetic, e.g., obtained by mutagenesis (e.g., phage display screening of a human phage library, etc.). In one embodiment, a chimeric antibody provided herein has murine V regions and human C regions. In one embodiment, the murine light chain V region is fused to a human kappa light chain. In one embodiment, the murine heavy chain V region is fused to a human IgG1 C region.

Methods for producing chimeric antibodies are known in the art. See e.g., Morrison, *Science* 229:1202 (1985); Oi et al., *BioTechniques* 4:214 (1986); Gillies et al., *J. Immunol. Methods* 125:191-202(1989); and U.S. Pat. Nos. 6,311,415, 5,807,715, 4,816,567, and 4,816,397; all of which are hereby incorporated by references in their entireties. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan, *Molecular Immunology* 28(4/5):489-498 (1991); Studnicka et al., *Protein Engineering* 7:805 (1994); and Roguska et al., *Proc. Natl. Acad. Sci. USA* 91:969 (1994)), and chain shuffling (U.S. Pat. No. 5,565,332); all of which are hereby incorporated by references in their entireties.

An exemplary process for the production of the recombinant chimeric anti-glycPD-1 antibodies can include the following: a) constructing, by conventional molecular biology methods, an expression vector that encodes and expresses an antibody heavy chain in which the CDRs and variable region of the murine anti-glycPD-1 monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-glycPD-1 monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized anti-glycPD-1 antibodies can include the following: a) constructing, by conventional molecular biology methods, an expression vector that encodes and expresses an antibody heavy chain in which the CDRs and a minimal portion of the variable region framework that are required to retain donor antibody binding specificity are derived from a non-human immunoglobulin, such as the murine anti-glycPD-1 monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the murine anti-glycPD-1 monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains can comprise cDNA or genomic DNA or both. The host cell used to express the recombinant antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands). Furthermore, codon usage can by optimized when host cell is selected to account for species specific codon usage bias and enhance protein expression. For example, for CHO cell expression the DNA encoding the antibodies can incorporate codons used preferentially by *Cricetulus griseus* (from where Chinese Hamster ovaries cells are derived. Methods of codon optimization may be employed to facilitate improved expression by a desired host cell (see e.g., Wohlgemuth et al., *Philos. Trans. R. Soc. Lond. B Biol. Sci.* 366(1580): 2979-2986 (2011); Jestin et al., *J. Mol. Evol.* 69(5):452-457 (2009); Bollenbach et al., *Genome Res.* 17(4):401-404 (2007); Kurland et al., *Prog. Nucleic Acid Res. Mol. Biol.* 31:191-219 (1984); Grosjean et al., *Gene* 18(3): 199-209 (1982)).

In one embodiment, the antibody is an immunoglobulin single variable domain derived from a camelid antibody, preferably from a heavy chain camelid antibody, devoid of light chains, which are known as $V_HH$ domain sequences or Nanobodies™. A Nanobody™ (Nb) is the smallest functional fragment or single variable domain ($V_HH$) of a naturally occurring single-chain antibody and is known to the person skilled in the art. They are derived from heavy chain only antibodies seen in camelids (Hamers-Casterman et al., *Nature* 363: 446-448 (1993); Desmyter et al., *Nat. Struct. Biol.*, 803-811 (1996)). In the family of "camelids," immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody™ or a $V_HH$ antibody. The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies, attached to reporter molecules, or humanized. Nbs are stable, survive the gastro-intestinal system and can easily be manufactured.

Unifying two antigen binding sites of different specificity into a single construct, bispecific antibodies have the ability to bring together two discreet antigens with exquisite specificity and therefore have great potential as therapeutic agents. Bispecific antibodies can be originally made by fusing two hybridomas, each capable of producing a different immunoglobulin. Bispecific antibodies can also be produced by joining two scFv antibody fragments while omitting the Fc portion present in full immunoglobulins. Each scFv unit in such constructs can be made up of one variable domain from each of the heavy ($V_H$) and light ($V_L$) antibody chains, joined with one another via a synthetic polypeptide linker, the latter often being genetically engineered so as to be minimally immunogenic while remaining maximally resistant to proteolysis. Respective scFv units can be joined by a number of techniques including incorporation of a short (usually less than 10 amino acids) polypeptide spacer bridging the two scFv units, thereby creating a bispecific single chain antibody. The resulting bispecific single chain antibody is therefore a species containing two $V_H/V_L$ pairs of different specificity on a single polypeptide chain, wherein the $V_H$ and $V_L$ domains in a respective scFv unit are separated by a polypeptide linker long enough to allow intramolecular association between these two domains, and wherein the thusly formed scFv units are contiguously tethered to one another through a polypeptide spacer kept short enough to prevent unwanted association between, for example, the $V_H$ domain of one scFv unit and the $V_L$ of the other scFv unit.

Examples of antigen binding fragments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (U.S. Pat. No. 5,091,513); and (ix) diabodies, multivalent, or multispecific fragments constructed by gene fusion (U.S. Patent Appln. Publn. No. 20050214860). Fv, scFv, or diabody molecules may be stabilized by the incorporation of disulfide bridges linking the VH and VL domains. Minibodies having a scFv joined to a CH3 domain can also be made (Hu et al., *Cancer Res.*, 56:3055-3061 (1996)).

Antibody-like binding peptidomimetics are also contemplated in embodiments. Liu et al., *Cell Mol. Biol.*, 49:209-216(2003) describe "antibody like binding peptidomimetics" (ABiPs), which are peptides that act as pared-down antibodies and have certain advantages of longer serum half-life as well as less cumbersome synthesis methods.

Glycosylated PD-1 Polypeptides

In yet a further embodiment, a composition is provided comprising a polypeptide comprising a fragment of at least 7 (e.g., at least 8, 9, 10, 11, 12, 13, 14, 15, 16, 17, 18, 19, 20 or more) contiguous amino acids of human PD-1 comprising at least one amino acid corresponding to position N49, N58, N74 or N116 of human PD-1, wherein at least one of said amino acids corresponding to position N49, N58, N74 or N116 of human PD-1 is glycosylated, wherein the polypeptide is formulated in a pharmaceutically acceptable carrier.

In some embodiments, provided herein are also polypeptides of at least 7 contiguous amino acids of human PD-1 having at least one amino acid corresponding to position N49, N58, N74 or N116 of human PD-1, wherein at least one of said amino acids corresponding to position N49, N58, N74 or N116 of human PD-1 is glycosylated. In some embodiments, the polypeptide has at least 7 contiguous amino acids of human PD-1 having an amino acid corresponding to position N49 which is glycosylated. In some embodiments, the polypeptide has at least 7 contiguous amino acids of human PD-1 having an amino acid corresponding to position N58 which is glycosylated. In some embodiments, the polypeptide has at least 7 contiguous amino acids of human PD-1 having an amino acid corresponding to position N74 which is glycosylated. In some embodiments, the polypeptide has at least 7 contiguous amino acids of human PD-1 having an amino acid corresponding to position N116 which is glycosylated.

For example, the polypeptide can be a fragment of amino acids 44-50 of human PD-1, wherein N49 is glycosylated. For another example, the polypeptide can be a fragment of amino acids 70-80 of human PD-1, wherein N74 is glycosylated. For yet another example, the polypeptide can be a fragment of amino acids 50-80 of human PD-1, wherein N58 and N74 are glycosylated. A person of ordinary skill in the art would understand polypeptides as contemplated here include any and all polypeptide that have at least 7 contiguous amino acids of human PD-1 including at least one amino acid corresponding to position N49, N58, N74 or N116 of human PD-1, wherein at least one of said amino acids corresponding to position N49, N58, N74 or N116 of human PD-1 is glycosylated.

In some embodiments, the polypeptide has at least 8, 9, 10, 11, 12, 13, 14, 15, 16, 17, 18, 19 or 20 contiguous amino acids of human PD-1. In some embodiments, the polypeptide has at least 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, 210, 220, 230, 240, 250, 260, or 270, 280 contiguous amino acids of human PD-1. In some embodiments, provided herein is a composition having at least two polypeptides provided herein. The at least two polypeptides can be separate molecule or linked as one molecule. In some embodiments, the composition has at least three polypeptides, at least four polypeptides, or at least five polypeptides. In some embodiments, the composition has two polypeptides, three polypeptides, four polypeptides, or five polypeptides.

In some embodiments, the polypeptides provided herein include unnatural amino acids. In some embodiments, the unnatural amino acids are methylated at the α-amino-group to produce peptides with methylated backbones. In some embodiments, the unnatural amino acids are R-amino acids. In some embodiments, the unnatural amino acid can include a dye (e.g., a fluorescent dye) or an affinity tag. In some embodiments, the polypeptides provided herein includes chemical modification. Chemical modifications include, for example, chemical modifications with biotin, fluorescent dyes. A skilled artisan will recognize that methods for introducing unnatural amino acids into a polypeptide and for chemically modifying a polypeptide are well known in the art.

In some embodiments, a polypeptide of the embodiments is fused or conjugated to an immunogenic polypeptide (e.g., keyhole limpet hemocyanin, KLH). In certain aspects, the polypeptide further comprises a Cys residue at the C- or N-terminus. For example, in some aspects, the polypeptide is conjugated to an immunogenic polypeptide by a disulfide linkage at the Cys residue.

In yet a further embodiment, an immunogenic composition is provided herein having a polypeptide comprising a fragment of at least 7 contiguous amino acids of human PD-1 comprising at least one amino acid corresponding to position N49, N58, N74 or N116 of human PD-1, wherein at least one of said amino acids corresponding to position N49, N58, N74 or N116 of human PD-1 is glycosylated, wherein the polypeptide is formulated in a pharmaceutically acceptable carrier. In some aspects, the immunogenic composition further comprises an adjuvant, such as alum or Freund's adjuvant.

In some embodiments, a method of making an antibody is provided, which includes administering a polypeptide to an animal and isolating the antibody from the animal, wherein the polypeptide has a fragment of at least 7 contiguous amino acids of human PD-1 having at least one amino acid corresponding to position N49, N58, N74 or N116 of human PD-1, and wherein at least one of said amino acids corresponding to position N49, N58, N74 and N116 of human PD-1 is glycosylated. The animal can be a mouse, rat, rabbit or human. In certain aspects a method further includes identifying the CDRs of the antibody and humanizing the sequences surrounding the CDRs to produce a humanized antibody. In still further aspects, the method comprises recombinantly expressing the humanized antibody. Thus, in a further embodiment, there is provided an isolated antibody produced by the foregoing method. Thus, in some embodiments, provided herein is an isolated antibody that selectively binds to a polypeptide of the embodiments (e.g., a polypeptide comprising a fragment of at least 7 contiguous amino acids of human PD-1 comprising at least one amino acid corresponding to position N49, N58, N74 or N116 of human PD-1, wherein at least one of said amino acids corresponding to position N49, N58, N74 or N116 of human PD-1 is glycosylated) relative to unglycosylated PD-1.

The polypeptides provided herein can be prepared by any methods known in the art. For example, the polypeptides can be prepared by chemical synthesis or recombinant production. Exemplary methods for expressing and purifying a recombinant polypeptide can be found, for example, in Scopes R. K., *Protein Purification—Principles and Practice, Springer Advanced Texts in Chemistry*, $3^{rd}$ Edition (1994); Simpson R. J. et al., *Basic Methods in Protein Purification and Analysis: A Laboratory Manual*, Cold Spring Harbor Laboratory Press, $1^{st}$ Edition (2008); Green M. R. and Sambrook J., *Molecular Cloning: A Laboratory Manual*, Cold Spring Harbor Laboratory Press, $4^{st}$ Edition (2012); Jensen K. J. et al., Peptide Synthesis and Applications (Methods in Molecular Biology), Humana Press, $2^{nd}$ Edition (2013). Chemically synthesis of a polypeptide can be accomplished by using methodologies well known in the art (see Kelley and Winkler, 1990, In: *Genetic Engineering Principles and Methods*, Setlow J. K, ed., Plenum Press, N.Y., Vol. 12, pp 1-19; Stewart et al., 1984, J. M. Young, J. D., *Solid Phase Peptide Synthesis*, Pierce Chemical Co., Rockford, Ill.; Marglin and Merrifield, *Ann. Rev. Biochem,* 39:841-866, at 862 (1970). Merrifield, R. B., 1963, *J. Am. Chern. Soc.* 85:2149-2154; *Chemical Approaches to the Synthesis of Peptides and Proteins*, Williams et al., Eds., 1997, CRC Press, Boca Raton Fla.; *Solid Phase Peptide Synthesis: A Practical Approach*, Atherton & Sheppard, Eds., 1989, IRL Press, Oxford, England; see also U.S. Pat. Nos. 4,105,603; 3,972,859; 3,842,067; and 3,862,925).

Modifications and Derivatives

Antibodies to glycosylated PD-1 can have the ability to neutralize or counteract the effects of glycosylated PD-1 regardless of the animal species, monoclonal cell line or other source of the antibody. Certain animal species may be less preferable for generating therapeutic antibodies because they may be more likely to cause allergic response due to activation of the complement system through the Fc portion of the antibody. However, whole antibodies can be enzymatically digested into Fc (complement binding) fragment, and into antibody fragments having the binding domain or CDR. Removal of the Fc portion reduces the likelihood that the antibody fragment will elicit an undesirable immunological response and, thus, antibodies without Fc can be used for prophylactic or therapeutic treatments. As described above, antibodies can also be constructed so as to be chimeric, partially or fully human, so as to reduce or eliminate the adverse immunological consequences resulting from administering to an animal an antibody that has been produced in, or has sequences from, other species.

The binding properties of anti-glycPD-1 antibodies can be further improved by screening for variants that exhibit desired properties. For example, such improvement can be done using various phage display methods known in the art. In phage display methods, functional antibody domains are displayed on the surface of phage particles, which carry the polynucleotide sequences encoding them. In a particular embodiment, such phage can be utilized to display antigen binding fragments, such as Fab and Fv or disulfide-bond stabilized Fv, expressed from a repertoire or combinatorial antibody library (e.g., human or murine). Phage expressing an antigen binding fragment that binds the antigen of interest can be selected or identified with antigen, e.g., using labeled antigen or antigen bound or captured to a solid surface or bead. Phage used in these methods are typically filamentous phage, including fd and M13. The antigen binding fragments are expressed as a recombinantly fused protein to either the phage gene III or gene VIII protein. Examples of phage display methods that can be used to make the antibodies or polypeptides as described herein include those disclosed in Brinkman et al., *J Immunol Methods*, 182:41-50 (1995); Ames et al., *J. Immunol. Methods*, 184:177-186 (1995); Kettleborough et al., *Eur. J. Immunol.*, 24:952-958(1994); Persic et al., *Gene*, 187:9-18 (1997); Burton et al., *Adv. Immunol.* 57:191-280 (1994); PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; all of which are hereby incorporated by references in their entireties.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT Publication WO 92/22324; Mullinax, R. L. et al., *BioTechniques*, 12(6):864-869 (1992); and Sawai et al., *Am. J Reprod. Immunol.* 34:26-34 (1995); and Better, M. et al. *Science* 240:1041-1043(1988); all of which are hereby incorporated by references in their entireties. Examples of techniques which can be used to produce single-chain Fvs and antibodies include those described in U.S. Pat. Nos. 4,946,778 and 5,258,498; Huston, J. S. et al., *Methods in Enzymology* 203:46-88(1991); Shu, L. et al., *Proc. Natl. Acad. Sci. (USA)* 90:7995-7999; and Skerra. A. et al., *Science* 240:1038-1040 (1988); all of which are hereby incorporated by references in their entireties.

Phage display technology can be used to increase the affinity of anti-glycPD-1 antibodies as described herein. This technique can be used in obtaining high affinity antibodies that could be used in the combinatorial methods described herein. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al., *J. Immunol.* 149:3903-3913(1992)). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al., *Proc. Natl. Acad. Sci.* (USA) 95(11):6037-6042 (1998); Yelton, D. E. et al., *J. Immunol.* 155:1994-2004 (1995). CDR walking which randomizes the light chain can also be used. (see Schier et al., *J. Mol. Biol.* 263:551-567 (1996)).

Random mutagenesis can be used in concert with methods of phage display to identify improved CDRs and/or variable regions. Phage display technology can alternatively be used to increase (or decrease) CDR affinity by directed mutagenesis (e.g., affinity maturation or "CDR-walking"). This technique uses the target antigen or an antigenic fragment thereof to identify antibodies having CDRs that bind with higher (or lower) affinity to the antigen when compared with the initial or parental antibody (see, e.g., Glaser, S. M. et al., *J. Immunol.* 149:3903-3913(1992)).

Methods for accomplishing such affinity maturation are described for example in: Krause, J. C. et al., *M Bio.* 2(1) pii: e00345-10. doi: 10.1128/mBio.00345-10(2011); Kuan, C. T. et al., *Int. J. Cancer* 10.1002/ijc.25645; Hackel, B. J. et al., *J. Mol. Biol.* 401(1):84-96(2010); Montgomery, D. L. et al., *MAbs* 1(5):462-474(2009); Gustchina, E. et al., *Virology* 393(1):112-119 (2009); Finlay, W. J. et al., *J. Mol. Biol.* 388(3):541-558 (2009); Bostrom, J. et al., Methods Mol. Biol. 525:353-376 (2009); Steidl, S. et al., *Mol. Immunol.* 46(1):135-144 (2008); and Barderas, R. et al., *Proc. Natl. Acad. Sci.* (*USA*) 105(26):9029-9034 (2008); all of which are hereby incorporated by references in their entireties.

Provided herein are also derivatives of anti-glycPD-1 antibodies or glycosylated PD-1 polypeptides that have one, two, three, four, five or more amino acid substitutions, additions, deletions or modifications relative to a "parental" (or wild-type) molecule. Such amino acid substitutions or additions can introduce naturally occurring (i.e., DNA-encoded) or non-naturally occurring amino acid residues. Such amino acids can be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In some embodiments, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al., *J. Biol. Chem.* 277(30): 26733-26740 (2002); Davies J. et al. *Biotechnology & Bioengineering* 74(4): 288-294(2001); all of which are hereby incorporated by references in their entireties). Methods of altering carbohydrate contents are known to those skilled in the art, see, e.g., Wallick, S. C. et al., *J. Exp. Med.* 168(3): 1099-1109(1988); Tao, M. H. et al., *J. Immunol.* 143(8): 2595-2601 (1989); Routledge, E. G. et al., *Transplantation* 60(8):847-53 (1995); Elliott, S. et al., *Nature Biotechnol.* 21:414-21(2003); Shields, R. L. et al., *J. Biol. Chem.* 277(30): 26733-26740 (2002); all of which are hereby incorporated by references in their entireties.

Substitutional variants can contain the exchange of one amino acid for another at one or more sites within the antibodies or polypeptides as provided herein, and can be designed to modulate one or more properties of the antibodies or polypeptide, with or without the loss of other functions or properties. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions can be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

In some embodiments, a humanized antibody is a derivative antibody. Such a humanized antibody includes amino acid residue substitutions, deletions or additions in one or more non-human CDRs. The humanized antibody derivative can have substantially the same binding, better binding, or worse binding when compared to a non-derivative humanized antibody. In some embodiments, one, two, three, four, or five amino acid residues of the CDR have been mutated, such as substituted, deleted or added.

In some embodiments, a polypeptide is a derivative polypeptide. Such a polypeptide includes amino acid residue substitutions, deletions or additions compared to wildtype human PD-1. The derivative polypeptide can have substantially the same binding, better binding, or worse binding with an anti-glycPD-1 antibody as compared with a non-derivative polypeptide. In some embodiments, one, two, three, four, or five amino acid residues of human PD-1 have been mutated, such as substituted, deleted or added.

The antibodies or polypeptides as described herein can be modified by chemical modifications using techniques known to those of skill in the art, including, but not limited to, specific chemical cleavage, acetylation, formulation, metabolic synthesis of tunicamycin, etc. In one embodiment, a derivative polypeptide or a derivative antibody possesses a similar or identical function as the parental polypeptide or antibody. In another embodiment, a derivative polypeptide or a derivative antibody exhibits an altered activity relative to the parent polypeptide or parental antibody. For example, a derivative antibody (or fragment thereof) can bind to its epitope more tightly or be more resistant to proteolysis than the parental antibody.

Substitutions, additions or deletions in the derivatized antibodies can be in the Fc region of the antibody and can thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821; all of which are hereby incorporated by references in their entireties. In some embodiments, the antibodies or other molecules can have altered affinity for an activating FcγR, e.g., FcγRIIIA Preferably such modifications also have an altered Fc-mediated effector function. Modifications that affect Fc-mediated effector function are well known in the art (see U.S. Pat. No.

6,194,551, and WO 00/42072). In some embodiments, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1 q binding activity, an altered complement-dependent cytotoxicity activity (CDC), a phagocytic activity, or any combination thereof.

Derivative antibodies or polypeptides can also have altered half-lives (e.g., serum half-lives) of parental molecules or antibodies in a mammal, preferably a human. In some embodiments, such alteration results in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of humanized antibodies or polypeptides in a mammal, preferably a human, results in a higher serum titer of said antibodies or polypeptides in the mammal, and thus, reduces the frequency of the administration of said a antibodies or polypeptides and/or reduces the concentration of said antibodies or polypeptides to be administered. Antibodies or polypeptides having increased in vivo half-lives can be generated by techniques known to those of skill in the art. For example, antibodies or polypeptides with increased in vivo half-lives can be generated by modifying (e.g., substituting, deleting or adding) amino acid residues identified as involved in the interaction between the Fc domain and the FcRn receptor. The humanized antibodies as described herein can be engineered to increase biological half-lives (see, e.g. U.S. Pat. No. 6,277,375). For example, humanized antibodies as described herein can be engineered in the Fc-hinge domain to have increased in vivo or serum half-lives.

Antibodies or polypeptides as described herein with increased in vivo half-lives can be generated by attaching to said antibodies or polypeptides polymer molecules such as high molecular weight polyethyleneglycol (PEG). PEG can be attached to the antibodies or polypeptides with or without a multifunctional linker either through site-specific conjugation of the PEG to the N- or C-terminus of said molecules or antibodies or via epsilon-amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies or polypeptides as described herein can also be modified by the methods and coupling agents described by Davis et al. (See U.S. Pat. No. 4,179,337) in order to provide compositions that can be injected into the mammalian circulatory system with substantially no immunogenic response. Removal of the Fc portion can reduce the likelihood that the antibody fragment elicits an undesirable immunological response and, thus, antibodies without Fc can be used for prophylactic or therapeutic treatments. As described above, antibodies can also be constructed so as to be chimeric, partially or fully human, so as to reduce or eliminate the adverse immunological consequences resulting from administering to an animal an antibody that has been produced in, or has sequences from, other species.

Fusions and Conjugates

The anti-glycPD-1 antibodies or glycosylated PD-1 polypeptides provided herein can also be expressed as fusion proteins with other proteins or chemically conjugated to another moiety.

In some embodiments, provided herein are antibodies or polypeptides that have an Fc portion, wherein the Fc portion can be varied by isotype or subclass, can be a chimeric or hybrid, and/or can be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al., *Mol. Immun.* 34(6): 441-452 (1997), Swann, P. G., *Curr. Opin. Immun.* 20:493-499 (2008), and Presta, L. G., *Curr. Opin. Immun.* 20:460-470 (2008). In some embodiments the Fc region is the native IgG1, IgG2, or IgG4 Fc region. In some embodiments the Fc region is a hybrid, for example a chimeric having of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region can include the entire hinge region, or less than the entire hinge region.

Another embodiment includes IgG2-4 hybrids and IgG4 mutants that have reduce binding to FcR which increase their half-life. Representative IG2-4 hybrids and IgG4 mutants are described in Angal et al., *Molec. Immunol.* 30(1):105-108 (1993); Mueller et al., *Mol. Immun.* 34(6): 441-452 (1997); and U.S. Pat. No. 6,982,323; all of which are hereby incorporated by references in their entireties. In some embodiments the IgG1 and/or IgG2 domain is deleted for example, Angal et al. describe IgG1 and IgG2 having serine 241 replaced with a proline.

In some embodiments, provided herein are fusion proteins or polypeptides having at least 10, at least 20, at least 30, at least 40, at least 50, at least 60, at least 70, at least 80, at least 90 or at least 100 amino acids.

In some embodiments, provided herein are anti-glycPD-1 antibodies or glycosylated PD-1 polypeptides that link to or covalently bind or form into a complex with at least one moiety. Such a moiety can be, but is not limited to, one that increases the efficacy of molecules as diagnostic or therapeutic agents. In some embodiments, the moiety can be image agents, toxins, therapeutic enzymes, antibiotics, radio-labeled nucleotides and the like.

In some embodiments, the moiety can be enzymes, hormones, cell surface receptors, toxins (such as abrin, ricin A, *pseudomonas* exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, monomethyl auristatin F (MMAF), monomethyl auristatin E (MMAE; e.g., vedotin) and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; Thorpe et al., *Immunol. Rev.* 62:119-158 (1982); Carter et al., *Cancer J.* 14(3):154-169 (2008); Alley et al., *Curr. Opin. Chem. Biol.* 14(4):529-537 (2010); Carter et al., *Amer. Assoc. Cancer Res. Educ. Book.* 2005(1):147-154 (2005); Carter et al., *Cancer J.* 14(3):154-169(2008); Chari, *Acc. Chem Res.* 41(1):98-107 (2008); Doronina et al., Nat. Biotechnol. 21(7):778-784(2003); Ducry et al., *Bioconjug Chem.* 21(1):5-13(2010); Senter, *Curr. Opin. Chem. Biol.* 13(3):235-244 (2009); and Teicher, *Curr Cancer Drug Targets.* 9(8):982-1004 (2009). auristatin E) (MMAE), e.g., vedotin; or combinations thereof.

In preferred embodiments, the antibody is conjugated to a maytansine is a benzoansamacrolide that was first isolated from the bark of the Ethiopian shrub *Maytenus ovatus*. This cytotoxic agent and derivatives thereof (e.g., maytansinoids) bind to tubulin near the *Vinca* alkaloid binding site. They are considered to have a high affinity for tubulin located at the ends of microtubules and lower affinity to sites distributed throughout the microtubules. The suppression of microtubule dynamics causes cells to arrest in the G2/M phase of the cell cycle, ultimately resulting in cell death by apoptosis. (Oroudjev et al., *Mol. Cancer Ther.*, 10L2700-2713 (2010)). Two maytansine derivatives (thiol-containing maytansinoids) include DM1 and DM4 (ImmunoGen, Inc., Waltham, Mass.) have been widely used in combination with irreversible and reversible linkers. In particular, DM1 attached to an antibody with a thioether linker is called "emtansine;" DM1 attached to an antibody with an SPP linker is called "mertansine". DM4 attached with an SPDB linker is called "ravtansine;" and DM4 attached with an sSPDB linker is called "soravtansine." (ImmunoGen, Inc., Waltham, Mass.). In an embodiment, the anti-glycPD-1 antibody-ADC comprises the tubulin-acting maytansinoid payload DM1. In an embodiment, the anti-glycPD-1 antibody-ADC comprises the tubulin-acting maytansinoid payload DM4. In an embodiment, the anti-glycPD-1 antibody-ADC comprises a DNA-acting payload, e.g., DGN462 (ImmunoGen, Inc., Waltham, Mass.). In an embodiment, the anti-glycPD-1 antibody component of the anti-glycPD-1 antibody-ADC is a chimeric or humanized form of STM418, or a binding portion thereof. In an embodiment, the anti-glycPD-1 antibody component of the anti-glycPD-1 antibody-ADC is a chimeric or humanized form of STM432, or a binding portion thereof.

In a particular embodiment, the cytotoxic agent conjugated to the anti-glycPD-1 antibody is MMAE (monomethyl auristatin E (or desmethyl-auristatin E)), a highly toxic, antineoplastic agent whose antimitotic activity involves inhibiting cell division by blocking the polymerization of tubulin. Vedotin, an International Nonproprietary Name, refers to MMAE plus its linking structure to an antibody in an MMAE-antibody conjugate. In more particular embodiments, the ADC is STM418 (chimeric or humanized form)-MMAE or STM432 (chimeric or humanized form)-MMAE.

A number of chemical linkers are known and used for conjugating a cytotoxic or DNA-acting drug payload to an antibody to produce ADCs. Certain linkers embraced for use alone or in combination for producing ADCs comprising the anti-glycPD-1 antibodies, particularly, those that internalize after binding their target as described herein, include SMCC (4-(N-Maleimidomethyl) cyclohexanecarboxylic acid N-hydroxysuccinimide ester); SPDB (N-succinimidyl 3-(2-pyridyldithio)butyrate); SPP (N-succinimidyl 4-(2-pyridyl-dithio)pentanoate); sulfo-SPDB or sSPDB (N-succinimidyl-4-(2-pyridyldithio)-2-sulfobutanoate); the thioether linker succinimidyl-4-(N-maleimidomethyl)cyclohexane-1-carboxylate (MCC); and vc (valine-citrulline dipeptide linker). By way of example, engineered linkers (e.g., SMCC, SPDB, S-SPDB), (Immunogen, Inc.) have been designed to be stable prior to the binding of an ADC to a tumor and then to optimize payload efficacy once the ACD is internalized inside a cancer cell. Other linkers, such as the dipeptide vc linker, which is a cathepsin-cleavable linker, may be used to conjugate an antibody to a cytotoxic agent, such as an auristatin which is a mitotic inhibitor derived from dolastatin 10, e.g., monomethylauristatin E (MMAE), e.g., vedotin. The cytotoxins may be conjugated to the antibody such that more than one toxin molecule is attached to each antibody molecule, for example, there may be, on average, 2, 3, 4, 5, 6, 7 or 8 toxin molecules per antibody.

In a particular embodiment, MMAE is indirectly linked to antibody cysteines by a maleimidocaproyl (MC) attachment group, which is coupled to valine-citrulline-p-aminobenzyloxycarbonyl-MMAE (MC-vc-PAB-MMAE). In the "MC-vc-PAB-MMAE" linear structure, "MC" consists of maleimide and caproic acid and is the moiety that attaches to an antibody, typically via cysteine groups on the H chain. In turn, "MC" is attached to a "vc" linker which consists of valine (Val) and citruline (Cit) and which is a cathepsin-cleavable linker that is cleaved by cathepsin inside of tumor or cancer cells. "vc" is attached to the spacer "PAB", i.e., paraminobenzoic acid, to which the MMAE cytotoxin is linked. MC-vc-PAB-MMAE ADCs release free, membrane-permeable MMAE when cleaved by proteases such as cathepsin B. In an embodiment, the linker to the antibody is stable in extracellular fluid, but is cleaved by cathepsin once the ADC has entered a tumor or cancer cell, thus activating the antimitotic mechanism of MMAE or other toxin drug. In another embodiment, monomethylauristatin F, (MMAF) is linked to antibody cysteines by maleimidocaproyl (MC- MMAF). In contrast to MC-vc-PAB-MMAE ADCs, MC-MMAF ADCs are uncleavable, like MCC-DM1 ADCs, and must be internalized and degraded within a cell, releasing cysteine-MC-MMAF as the active drug inside the cell.

In an embodiment, the cytotoxic payload is released in the lysosome following internalization of the ADC into a cell. In the lysosome, lysosomal enzymes digest the antibody component of the ADC. Following lysosomal degradation, the drug (and drug-linker) payload is released into the cytoplasm, where the drug binds intracellular targets, ultimately causing cell death. Optimally, the released payload is fully active, with the linker still attached. In other embodiments in which the target bound to the ADC results in poor trafficking to the lysosome, linkers which are stable outside of the target cell, but which cleave the payload from the antibody component once inside the cell provide an alternative mode for payload release within the cell, but outside of the lysosome. In other embodiments, the linker is stable in extracellular fluid, but is cleaved by cathepsin once the ADC has entered a tumor or cancer cell, thus activating the antimitotic or other cytotoxic mechanism of the toxin drug. In other embodiments, a payload released by the action of cleavable linkers is able to enter a neighboring cancer cells and kill them via a bystander effect, thus augmenting the targeting and tumor killing activity of an ADC.

In some embodiments, antibodies and polypeptides as described herein can be conjugated to a marker, such as a peptide, to facilitate purification. In some embodiments, the marker is a hexa-histidine peptide (SEQ ID NO:42), the hemagglutinin "HA" tag, which corresponds to an epitope derived from the influenza hemagglutinin protein (Wilson, I. A. et al., *Cell,* 37:767-778 (1984)), or the "flag" tag (Knappik, A. et al., *Biotechniques* 17(4):754-761 (1994)).

In some embodiments, the moiety can be an image agent that can be detected in an assay. Such image agent can be enzymes, prosthetic groups, radiolabels, nonradioactive paramagnetic metal ions, haptens, fluorescent labels, phosphorescent molecules, chemiluminescent molecules, chromophores, luminescent molecules, bioluminescent molecules, photoaffinity molecules, colored particles or ligands, such as biotin.

In some embodiments, the enzymes include, but not limited to, horseradish peroxidase, alkaline phosphatase, beta-galactosidase, or acetylcholinesterase; the prosthetic group complexes include, but not limited to, streptavidin/biotin and avidin/biotin; the fluorescent materials include, but not limited to, umbelliferone, fluorescein, fluorescein isothiocyanate, rhodamine, dichlorotriazinylamine fluorescein, dansyl chloride or phycoerythrin; the luminescent material such as, but not limited to, luminol; the bioluminescent materials include, but not limited to, luciferase, luciferin, and aequorin; the radioactive material include, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb) yttrium ($^{90}$Y), zinc ($^{65}$Zn); positron emitting metals using various positron emission tomographies, and nonradioactive paramagnetic metal ions.

The image agent can be conjugated to the antibodies or polypeptides provided herein either directly, or indirectly through an intermediate (such as, for example, a linker known in the art) using techniques known in the art. See, for example, U.S. Pat. No. 4,741,900 for metal ions which can be conjugated to antibodies and other molecules as described herein for use as diagnostics. Some conjugation methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Monoclonal antibodies can also be reacted with an enzyme in the presence of a coupling agent such as glutaraldehyde or periodate. Conjugates with fluorescein markers can be prepared in the presence of these coupling agents or by reaction with an isothiocyanate.

In some embodiments, antibodies or polypeptides as described herein can be conjugated to a second antibody to form an antibody heteroconjugate as described by Segal in U.S. Pat. No. 4,676,980. Such heteroconjugate antibodies can additionally bind to haptens (e.g., fluorescein), or to cellular markers (e.g., 4-1-BB, B7-H4, CD4, CD8, CD14, CD25, CD27, CD40, CD68, CD163, CTLA4, GITR, LAG-3, OX40, TIM3, TIM4, TLR2, LIGHT, ICOS, B7-H3, B7-H7, B7-H7CR, CD70, CD47) or to cytokines (e.g., IL-7, IL-15, IL-12, IL-4 TGF-beta, IL-10, IL-17, IFNγ, Flt3, BLys) or chemokines (e.g., CCL21).

In some embodiments, the anti-glycPD-1 antibodies or glycosylated PD-1 polypeptides described herein can also be attached to solid supports, which can be useful for immunoassays or purification of the target antigen or of other molecules that are capable of binding to target antigen that has been immobilized to the support via binding to an antibody or antigen binding fragment as described herein. Such solid supports include, but are not limited to, glass, cellulose, polyacrylamide, nylon, polystyrene, polyvinyl chloride or polypropylene.

Protein Purification

Protein purification techniques are well known to those of skill in the art. These techniques involve, at one level, the homogenization and crude fractionation of the cells, tissue, or organ into polypeptide and non-polypeptide fractions. The protein or polypeptide of interest can be further purified using chromatographic and electrophoretic techniques to achieve partial or complete purification (or purification to homogeneity) unless otherwise specified. Analytical methods particularly suited to the preparation of a pure peptide are ion-exchange chromatography, size-exclusion chromatography, reverse phase chromatography, hydroxyapatite chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC). As is generally known in the art, it is believed that the order of conducting the various purification steps can be changed, or that certain steps may be omitted, and still result in a suitable method for the preparation of a substantially purified polypeptide.

A purified polypeptide is intended to refer to a composition, isolatable from other components, wherein the polypeptide is purified to any degree relative to its naturally-obtainable state. An isolated or purified polypeptide, therefore, also refers to a polypeptide free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a composition in which the polypeptide forms the major component of the composition, such as constituting about 50%, about 60%, about 70%, about 80%, about 90%, about 95%, or more of the proteins in the composition.

Various methods for quantifying the degree of purification of the polypeptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "fold purification number." The actual units used to represent the amount of activity will, of course, be dependent upon the particular assay technique chosen to follow the purification, and whether or not the expressed polypeptide exhibits a detectable activity.

There is no general requirement that the polypeptide will always be provided in its most purified state. Indeed, it is contemplated that less substantially purified products can have utility in certain embodiments. Partial purification can be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size-exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase. The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

Provided herein also is a method for assessing PD-1 glycosylation, N-linked glycosylation or N-glycosylation comprising contacting the PD-1-containing sample with an antibody of the embodiments (e.g., an antibody selectively binds to glycosylated PD-1 relative to unglycosylated PD-1). In some aspects, the method is an in vitro method. In certain aspects, the sample is cell sample.

Nucleic Acids.

The present disclosure also contemplates nucleic acid molecules (DNA or RNA) that encode any anti-glycPD-1 antibodies or glycosylated PD-1 polypeptides as described herein. Provided herein are also vector molecules (such as plasmids) that are capable of transmitting or of replication such nucleic acid molecules. The nucleic acids can be single-stranded, double-stranded, and can contain both single-stranded and double-stranded portions.

Pharmaceutical Preparations

Where clinical application of a pharmaceutical composition containing an antibody is undertaken, it will generally be beneficial to prepare a pharmaceutical or therapeutic composition appropriate for the intended application. Generally, pharmaceutical compositions can have an effective amount of anti-glycPD-1 antibodies or glycosylated PD-1 polypeptides as described herein, or with additional agents dissolved or dispersed in a pharmaceutically acceptable carrier.

Provided herein are also compositions having anti-glycPD-1 antibodies or glycosylated PD-1 polypeptides as described herein. In some embodiments, the composition can have at least 0.1% by weight the antibodies or polypeptides. In some embodiments, the composition can have at least 0.5%, 1%, 2%, 3%, 4%, 5%, 6%, 7% 8%, 9%, 10%, 15%, 20%, 25%, 30%, 35%, 40%, 45%, 50%, 55%, 60%, 65%, 70%, 75%, 80%, 85%, 90%, or more by weight of anti-glycPD-1 antibodies or glycosylated PD-1 polypeptides. In other embodiments, for example, anti-glycPD-1 or glycosylated PD-1 polypeptides can constitute between about 2% to about 75% of the weight of the composition, between about 25% to about 60%, between about 30% to about 50%, or any range therein. The amount of active compound(s) in each therapeutically useful composition can be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

The composition can be a pharmaceutical composition having anti-glycPD-1 antibodies or glycosylated PD-1 polypeptides as the active ingredient as well as a pharmaceutically acceptable carrier. The pharmaceutical composition can further include one or more additional active ingredient. A pharmaceutically acceptable carrier can be a carrier approved by a regulatory agency of the Federal or a state government, or listed in the U.S. Pharmacopeia, European Pharmacopeia or other generally recognized Pharmacopeia for use in animals, and more particularly in humans.

As used herein, and unless otherwise specified, the term "carrier" refers to a diluent, adjuvant (e.g., Freund's adjuvant (complete or incomplete)), excipient, stabilizers or vehicle with which a therapeutic agent is administered. A "pharmaceutically acceptable carrier" is a carrier that is nontoxic to the cell or mammal being exposed thereto at the dosages and concentrations employed, which can be sterile liquids, such as water and oils, including those of petroleum, animal, vegetable or synthetic origin, such as peanut oil, soybean oil, mineral oil, sesame oil and the like. Pharmaceutically acceptable molecular entities or compositions do not produce an adverse, allergic, or other untoward reaction when administered to an animal, such as a human, as appropriate. The preparation of a pharmaceutical composition having an antibody or additional active ingredient is known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by FDA Office of Biological Standards.

It is contemplated that the compositions include about 0.001 mg and about 10 mg of total antibodies or polypeptides per ml. Thus, the concentration of antibodies or polypeptides in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% can be an anti-glycPD-1 antibody or a glycosylated PD-1 polypeptide.

The preparation of a pharmaceutical composition having the antibodies or other polypeptides as described herein as active ingredient are known to those of skill in the art in light of the present disclosure, as exemplified by Remington's Pharmaceutical Sciences, 18th Ed., 1990, incorporated herein by reference. Moreover, for animal (including human) administration, it is understood that preparations should meet sterility, pyrogenicity, general safety, and purity standards as required by FDA Office of Biological Standards.

The pharmaceutically acceptable carriers include liquid, semi-solid, i.e., pastes, or solid carriers. Examples of carriers or diluents include fats, oils, water, saline solutions, lipids, liposomes, resins, binders, fillers, and the like, or combinations thereof. The pharmaceutically acceptable carrier can include aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, anti-oxidants, preservatives (e.g., antibacterial or antifungal agents, anti-oxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects of the present disclosure, the composition can be combined with the carrier in any convenient and practical manner, i.e., by solution, suspension, emulsification, admixture, encapsulation, absorption, grinding, and the like. Such procedures are routine for those skilled in the art.

In some embodiments, a pharmaceutically acceptable carrier can be an aqueous pH buffered solution. Examples include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

In some embodiments, pharmaceutically acceptable carriers can be sterile liquids, such as water and oils, including those of petroleum, animal, vegetable or synthetic origin, such as peanut oil, soybean oil, mineral oil, sesame oil and the like. Water can be a carrier, particularly when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, polysorbate-80 and the like. The composition can also contain minor amounts of wetting or emulsifying agents, or pH buffering agents. These compositions can take the form of solutions, suspensions, emulsion, tablets, pills, capsules, powders, sustained-release formulations and the like.

Certain embodiments of the present disclosure can have different types of carriers depending on whether it is to be administered in solid, liquid, or aerosol form, and whether it needs to be sterile for the route of administration, such as injection. The compositions can be formulated for administration intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference). Typically, such compositions can be prepared as either liquid solutions or suspensions; solid forms suitable for use to prepare solutions or suspensions upon the addition of a liquid prior to injection can also be prepared; and, the preparations can also be emulsified.

The anti-glycPD-1 antibodies or glycosylated PD-1 polypeptides can be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, 2-ethylamino ethanol, histidine, or procaine.

In further embodiments, provided herein are pharmaceutical compositions having a lipid. A lipid can broadly include a class of substances that are characteristically insoluble in water and extractable with an organic solvent. Examples include compounds that contain long-chain aliphatic hydrocarbons and their derivatives. A lipid can be naturally occurring or synthetic (i.e., designed or produced by man). A lipid can be a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Compounds other than those specifically described herein that are understood by one of skill in the art as lipids can also be used.

One of ordinary skill in the art would be familiar with the range of techniques that can be employed for dispersing a composition in a lipid vehicle. For example, antibodies or polypeptides can be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of active ingredient in each therapeutically useful composition can be prepared in such a way that a suitable dosage will be obtained in any given unit dose of the compound. Factors, such as solubility, bioavailability, biological half-life, route of administration, product shelf life, as well as other pharmacological considerations, can be contemplated by one skilled in the art of preparing such pharmaceutical formulations, and as such, a variety of dosages and treatment regimens may be desirable.

A unit dose or dosage refers to physically discrete units suitable for use in a subject, each unit containing a predetermined quantity of the pharmaceutical composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose can have from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject.

As a person of ordinary skill in the art would understand, the compositions described herein are not limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy varies according to the type of use and mode of administration, as well as the particularized requirements of individual subjects. The actual dosage amount of a composition administered to an animal patient, including a human patient, can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount can vary according to the response of the subject. The practitioner responsible for administration will, in any event, determine the concentration of active ingredient(s) in a composition and appropriate dose(s) for the individual subject.

Treatment of Diseases

As used herein, and unless otherwise specified, the term "subject" refers to an animal that is the object of treatment, observation and/or experiment. "Animal" includes vertebrates and invertebrates, such as fish, shellfish, reptiles, birds, and, in particular, mammals. "Mammal" includes, but not limited to, mice, rats, rabbits, guinea pigs, dogs, cats, sheep, goats, cows, horses, primates, such as monkeys, chimpanzees, apes, and humans. In some embodiments, the subject is a human.

As used herein, and unless otherwise specified, the term "cancer" or "cancerous" refers to the physiological condition in mammals that is typically characterized by unregulated cell growth. Examples of cancer include, but are not limited to, hematological cancers and solid tumors.

As used herein, and unless otherwise specified, the term "treat," "treating," or "treatment" refer to administration or application of a therapeutic agent to a subject or performance of a procedure or modality on a subject for the purpose of obtaining a therapeutic benefit of a disease or health-related condition. For example, a treatment can include administration of a therapeutically effective amount of an anti-glycPD-1 antibody to a subject. When used in reference to a cancer patient, the term "treat," "treating," or "treatment" refers to an action that potentially reduces the severity of the cancer, or retards or slows the progression of the cancer, including (a) inhibiting the cancer growth, reducing cancer growth rate, arresting development, reducing cancer invasiveness or preventing metastasis of the cancer, and (b) causing regression of the cancer, delaying or minimizing one or more symptoms associated with the presence of the cancer, or prolonging the survival of a cancer patient.

As used herein, and unless otherwise specified, the term "therapeutically effective amount" refers to the amount of an agent (e.g., an antibody or a polypeptide described herein or any other agent described herein) that is sufficient to reduce and/or ameliorate the severity and/or duration of a given disease, disorder or condition, and/or a symptom related thereto. A therapeutically effective amount of an agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody provided herein). A therapeutically effective amount of a substance/molecule/agent of the present disclosure (e.g., an anti-glycPD-1 antibody or glycosylated PD-1 polypeptide) can vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects.

As used herein, and unless otherwise specified, the term "administer" or "administration" refers to the act of injecting or otherwise physically delivering a substance as it exists outside the body into a patient, such as by mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

Provided herein are also therapeutic uses of the anti-glycPD-1 antibodies and glycosylated PD-1 polypeptides. These antibodies or polypeptides can be used to modulate the activity of PD-1/PD-L1 signaling. These antibodies or polypeptides can also be used treat a disease by inhibiting the suppressive activity of PD-1 in T cell activation or proliferation. Accordingly, provided herein are uses of such antibodies or polypeptides in up-modulating the immune system of a subject by inhibiting or blocking the PD-1 signaling. In some embodiments, provided herein are uses of the antibodies or polypeptides to block PD-1 from binding PD-L1.

In some embodiments, provided herein are also therapeutic uses of the anti-glycPD-1 antibodies and glycosylated PD-1 polypeptides in treating cancer. Up-modulation of the immune system is particularly desirable in the treatment of cancers, and thus provided herein are also methods of cancer treatment. A cancer refers to a neoplasm or tumor resulting from abnormal uncontrolled growth of cells. A cancer can be a primary cancer or a metastatic cancer. In specific embodiments, the cancer cells are positive for PD-L1.

In certain aspects, a polypeptide or antibody of the embodiments (e.g., a glycosylated PD-1 polypeptide or an antibody that binds to glycosylated PD-1) can be administered to treat a cancer. In specific embodiments, the anti-glycPD-1 antibody is a chimeric or humanized form of STM418 or STM432. Cancers for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer can specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the antibodies or polypeptides provided herein can be used to treat a cancer that is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer.

The polypeptide or antibody can be used herein as an antitumor agent in a variety of modalities. In a particular embodiment, provided herein are methods of using a polypeptide or antibody as an antitumor agent, and therefore comprises contacting a population of tumor cells with a therapeutically effective amount of a polypeptide or antibody for a time period sufficient to inhibit tumor cell growth.

Various delivery systems are also known and can be used to administer the anti-glycPD-1 antibodies or related molecules of glycosylated PD-1 polypeptides, or related pharmaceutical compositions, such as encapsulation in liposomes, microparticles, microcapsules, recombinant cells capable of expressing the antibody or fusion protein, receptor-mediated endocytosis (see, e.g., Wu and Wu, 1987, J. Biol. Chem. 262:4429-4432), construction of a nucleic acid as part of a retroviral or other vector, etc.

The methods of administration as provided herein include, but are not limited to, injection, as by parenteral administration (e.g., intradermal, intramuscular, intraperitoneal, intravenous and subcutaneous), epidural, and mucosal (e.g., intranasal and oral routes). In some embodiments, the antibodies, other molecules, or pharmaceutical compositions provided herein are administered intramuscularly, intravenously, subcutaneously, intravenously, intraperitoneally, orally, intramuscularly, subcutaneously, intracavity, transdermally, or dermally. The compositions can be administered by any convenient route, for example, by infusion or bolus injection, by absorption through epithelial or mucocutaneous linings (e.g., oral mucosa, rectal and intestinal mucosa, etc.) and can be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903; all of which are hereby incorporated by reference in their entireties. In some embodiments, the antibodies, other molecules, or pharmaceutical compositions provided herein are administered locally to the area in need of treatment, which can be achieved by, for example, local infusion, by injection, or by means of an implant, said implant being of a porous, non-porous, or gelatinous material, including membranes, such as sialastic membranes, or fibers. In some embodiments, when administering antibodies or other molecules as described herein, care is taken to use materials to which the antibodies or other molecules do not absorb.

In some embodiments, the antibodies or polypeptides provided herein are formulated in liposomes for targeted delivery. Liposomes are vesicles comprised of concentrically ordered phopsholipid bilayers which encapsulate an aqueous phase. Liposomes typically have various types of lipids, phospholipids, and/or surfactants. The components of liposomes are arranged in a bilayer configuration, similar to the lipid arrangement of biological membranes. Liposomes can be useful delivery vehicles due, in part, to their biocompatibility, low immunogenicity, and low toxicity. Methods for preparation of liposomes are known in the art and are provided herein, see, e.g., Epstein et al., 1985, *Proc. Natl. Acad. Sci. USA*, 82: 3688; Hwang et al., 1980 *Proc. Natl. Acad. Sci. USA*, 77: 4030-4; U.S. Pat. Nos. 4,485,045 and 4,544,545; all of which are hereby incorporated by reference in their entireties.

Provided herein are also methods of preparing liposomes with a prolonged serum half-life, i.e., enhanced circulation time, such as those disclosed in U.S. Pat. No. 5,013,556. In some embodiments, liposomes used in the methods provided herein are not rapidly cleared from circulation, i.e., are not taken up into the mononuclear phagocyte system (MPS). Provided herein are also sterically stabilized liposomes which are prepared using common methods known to one skilled in the art. Sterically stabilized liposomes can contain lipid components with bulky and highly flexible hydrophilic moieties, which reduces the unwanted reaction of liposomes with serum proteins, reduces oposonization with serum components and reduces recognition by MPS. Sterically stabilized liposomes can be prepared using polyethylene glycol. For preparation of liposomes and sterically stabilized liposome, see, e.g., Bendas et al., 2001 *BioDrugs*, 15(4): 215-224; Allen et al., 1987 *FEBS Lett.* 223: 42-6; Klibanov et al., 1990 *FEBS Lett.*, 268: 235-7; Blum et al., 1990, *Biochim. Biophys. Acta.*, 1029: 91-7; Torchilin et al., 1996, *J. Liposome Res.* 6: 99-116; Litzinger et al., 1994, *Biochim. Biophys. Acta*, 1190: 99-107; Maruyama et al., 1991, *Chem. Pharm. Bull.*, 39: 1620-2; Klibanov et al., 1991, *Biochim Biophys Acta*, 1062; 142-8; Allen et al., 1994, *Adv. Drug Deliv. Rev,* 13: 285-309, which are hereby incorporated by reference in their entireties.

Provided herein are also liposomes that are adapted for specific organ targeting, see, e.g., U.S. Pat. No. 4,544,545, or specific cell targeting, see, e.g., U.S. Patent Application Publication No. 2005/0074403, which are hereby incorporated by reference in their entireties. Particularly useful liposomes for use in the compositions and methods provided herein can be generated by reverse phase evaporation method with a lipid composition comprising phosphatidylcholine, cholesterol, and PEG derivatized phosphatidylethanolamine (PEG-PE). Liposomes can be extruded through filters of defined pore size to yield liposomes with the desired diameter. In some embodiments, a molecule having an antigen binding fragment, e.g., F(ab'), can be conjugated to the liposomes using previously described methods, see, e.g., Martin et al., 1982, *J. Biol. Chem.* 257: 286-288, which is hereby incorporated by reference in its entirety.

The humanized or chimeric antibodies as described herein can also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art, see, e.g., U.S. Pat. No. 6,787,153; Allen et al., 1995, *Stealth Liposomes, Boca Rotan*: CRC Press, 233-44; Hansen et al., 1995, *Biochim. Biophys. Acta*, 1239: 133-144, which are hereby incorporated by reference in their entireties. In some embodiments, immunoliposomes for use in the methods and compositions provided herein are further sterically stabilized. In some embodiments, the humanized antibodies as described herein are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phospahtidylinositol (PI). To achieve a covalent linkage between an antibody and a hydrophobic anchor, any of the known biochemical strategies in the art can be used, see, e.g., J. Thomas August ed., 1997, *Gene Therapy: Advances in Pharmacology*, Volume 40, Academic Press, San Diego, Calif., p. 399-435, which are hereby incorporated by reference in their entireties. For example, a functional group on an antibody molecule can react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, *Biochemistry*, 35: 1100-1105; Loughrey et al., 1987, *Biochim. Biophys. Acta*, 901: 157-160; Martin et al., 1982, *J. Biol. Chem.* 257: 286-288; Martin et al., 1981, *Biochemistry*, 20: 4429-38, which are hereby incorporated by reference in their entireties. The immunoliposomal formulations having the anti-glycosylated PD-1 antibodies can be particularly effective as therapeutic agents, since they deliver the active ingredient to the cytoplasm of the target cell, i.e., the cell comprising the receptor to which the antibody binds. In some embodiments, the immunoliposomes can have an increased half-life in blood, specifically target cells, and can be internalized into the cytoplasm of the target cells thereby avoiding loss of the therapeutic agent or degradation by the endolysosomal pathway.

The immunoliposomal compositions provided herein can have one or more vesicle forming lipids, an antibody or other molecule of the invention or a fragment or derivative thereof, and, optionally, a hydrophilic polymer. A vesicle forming lipid can be a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations provided herein are known to one skilled in the art and encompassed within the description. In some embodiments, the immunoliposomal compositions further include a hydrophilic polymer, e.g., polyethylene glycol, and ganglioside GM1, which increases the serum half-life of the liposome. Methods of conjugating hydrophilic polymers to liposomes are well known in the art and encompassed within the description. Additional exemplary immunoliposomes and methods of preparing them can be find in, e.g., U.S. Patent Application Publication No. 2003/0044407; PCT International Publication No. WO 97/38731, Vingerhoeads et al., 1994, *Immunomethods*, 4: 259-72; Maruyama, 2000, *Biol. Pharm. Bull.* 23(7): 791-799; Abra et al., 2002, *Journal of Liposome Research*, 12(1&2): 1-3; Park, 2002, *Bioscience Reports*, 22(2): 267-281; Bendas et al., 2001 *BioDrugs*, 14(4): 215-224, J. Thomas August ed., 1997, *Gene Therapy: Advances in Pharmacology*, Volume 40, Academic Press, San Diego, Calif., p. 399-435; all of which are hereby incorporated by reference in their entireties.

Provided herein are also methods of treating a cancer patient by administering a unit dose to the patient the anti-glycPD-1 antibodies. Provided herein are also methods of treating a cancer patient by administering a unit dose to the patient glycosylated PD-1 polypeptides. A unit dose refers to physically discrete units suitable as unitary dosage for the subject, each unit containing a predetermined quantity of active material calculated to produce the desired therapeutic effect in association with the required diluent, i.e., carrier, or vehicle.

The antibodies, polypeptides, or compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual subject. However, suitable dosage ranges for systemic application are disclosed herein and depend on the route of administration. Suitable regimes for initial and booster administration are also contemplated and typically include by an initial administration followed by repeated doses at one or more hour intervals by a subsequent injection or other administration. Exemplary multiple administrations are described herein and are useful to maintain continuously high serum and tissue levels of polypeptide or antibody. Alternatively, continuous intravenous infusion sufficient to maintain concentrations in the blood in the ranges specified for in vivo therapies are contemplated.

A therapeutically effective amount is a predetermined amount calculated to achieve the desired effect. Generally, the dosage will vary with age of, condition of, sex of, and extent of the disease in the patient and can be determined by one of skill in the art. The dosage can be adjusted by the individual physician in the event of any complication.

In some embodiments, the antibodies, polypeptides, or pharmaceutical compositions provided herein are packaged in a hermetically sealed container, such as an ampoule or sachette. In one embodiment, the antibodies, polypeptides, or pharmaceutical compositions provided herein are supplied as a dry sterilized lyophilized powder or water free concentrate in a hermetically sealed container and can be reconstituted, e.g., with water or saline to the appropriate concentration for administration to a subject. In some embodiments, the antibodies, polypeptides, or pharmaceutical compositions provided herein are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies, polypeptides, or pharmaceutical compositions provided herein should be stored at between 2 and 8° C. in their original container and should be administered within 12 hours, preferably within 6 hours, within 5 hours, within 3 hours, or within 1 hour after being reconstituted. In an alternative embodiment, the antibodies, polypeptides, or pharmaceutical compositions provided herein are supplied in liquid form in a hermetically sealed container indicating the quantity and concentration of the antibodies, polypeptides, or pharmaceutical compositions. In some embodiments, the liquid form of the antibodies, polypeptides, or pharmaceutical compositions provided herein are supplied in a hermetically sealed container at least 1 mg/ml, more preferably at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml.

The precise dose to be employed in the formulation will also depend on the route of administration, and the seriousness of the condition, and should be decided according to the judgment of the practitioner and each patient's circumstances. Effective doses can be extrapolated from dose-response curves derived from in vitro or animal model test systems. For the anti-glycPD-1 antibodies or glycosylated PD-1 polypeptides, the dosage administered to a patient is typically 0.01 mg/kg to 100 mg/kg of the patient's body weight. In some embodiments, the dosage administered to a patient is between 0.01 mg/kg and 20 mg/kg, 0.01 mg/kg and 10 mg/kg, 0.01 mg/kg and 5 mg/kg, 0.01 and 2 mg/kg, 0.01 and 1 mg/kg, 0.01 mg/kg and 0.75 mg/kg, 0.01 mg/kg and 0.5 mg/kg, 0.01 mg/kg to 0.25 mg/kg, 0.01 to 0.15 mg/kg, 0.01 to 0.10 mg/kg, 0.01 to 0.05 mg/kg, or 0.01 to 0.025 mg/kg of the patient's body weight. In particular, the dosage administered to a patient can be 0.2 mg/kg, 0.3 mg/kg, 1 mg/kg, 3 mg/kg, 6 mg/kg or 10 mg/kg. A dose as low as 0.01 mg/kg is predicted to show appreciable pharmacodynamic effects. Dose levels of 0.10-1 mg/kg are predicted to be most appropriate. Higher doses (e.g., 1-30 mg/kg) can also be expected to be active. Generally, human antibodies have a longer half-life within the human body than antibodies from other species due to the immune response to the foreign polypeptides. Thus, lower dosages of human antibodies and less frequent administration can be practiced. Further, the dosage and frequency of administration of antibodies or polypeptides provided herein can be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations having one or more antibodies, molecules, or pharmaceutical compositions provided herein. See, e.g., U.S. Pat. No. 4,526,938; PCT publication WO 91/05548; PCT publication WO 96/20698; Ning et al., *Radiotherapy & Oncology* 39:179-189 (1996), Song et al., *PDA Journal of Pharmaceutical Science & Technology* 50:372-397 (1995); Cleek et al., *Pro. Int'l. Symp. Control. Rel. Bioact. Mater.* 24:853-854 (1997); and Lam et al., *Proc. Int'l. Symp. Control Rel. Bioact. Mater.* 24:759-760(1997); all of which are hereby incorporated by reference in their entireties. In one embodiment, a pump can be used in a controlled release system (See Langer, supra; Sefton, 1987, *CRC Crit. Ref Biomed. Eng.* 14:20; Buchwald et al., 1980, *Surgery* 88:507; and Saudek et al., 1989, *N. Engl. J. Med.* 321:574). In another embodiment, polymeric materials can be used to achieve controlled release of antibodies or polypeptides (see e.g., Medical Applications of Controlled Release, Langer and Wise (eds.), CRC Pres, Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912,015; 5,989,463; 5,128,326; PCT Publication No. WO 99/15154; and PCT Publication No. WO 99/20253); all of which are hereby incorporated by references in their entireties.

Examples of polymers that can be used in sustained release formulations include, but are not limited to, poly(-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (see U.S. Pat. No. 5,945,155), which is hereby incorporated by references in its entirety. Based upon the therapeutic effect of the in situ controlled release of the bioactive material from the polymer system, the implantation can generally occur anywhere within the body of the patient in need of therapeutic treatment.

In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (see U.S. Pat. No. 5,888,533). Controlled release systems are also discussed in the review by Langer (1990, *Science* 249:1527-1533). Any technique known to one of skill in the art can be used to produce sustained release formulations comprising one or more therapeutic agents provided herein. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760; all of which are hereby incorporated by references in their entireties.

Provided herein are also embodiment wherein the composition has nucleic acids encoding antibodies or polypeptides as provided herein, wherein the nucleic acid can be administered in vivo to promote expression of its encoded antibody or polypeptide, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

Treatment of a subject with a therapeutically effective amount of antibodies, polypeptides or pharmaceutical composition provided herein can include a single treatment or a series of treatments. It is contemplated that the antibodies, polypeptides, or pharmaceutical compositions provided herein can be administered systemically or locally to treat disease, such as to inhibit tumor cell growth or to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive. In some embodiments, they can be administered after the regression of primary cancer to prevent metastasis.

Combination Treatments

In certain embodiments, the compositions and methods of the embodiments involve administration of glycosylated PD-1 polypeptide or an antibody that selectively binds to glycosylated PD-1, in combination with a second or additional therapy. Such therapy can be applied in the treatment of any disease that is associated with PD-1 or glycosylated PD-1. For example, the disease can be a cancer, and the second therapy is an anticancer or anti-hyperproliferative therapy.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process can involve administering a polypeptide or antibody and a second therapy. The second therapy may or may not have a direct cytotoxic effect. For example, the second therapy can be an agent that upregulates the immune system without having a direct cytotoxic effect. A tissue, tumor, or cell can be exposed to one or more compositions or pharmacological formulation(s) comprising one or more of the agents (e.g., an antibody or an anti-cancer agent), or by exposing the tissue, tumor, and/or cell with two or more distinct compositions or formulations, wherein one composition provides 1) a polypeptide or antibody, 2) an anti-cancer agent, or 3) both a polypeptide or antibody and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic polypeptide or antibody and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

The anti-glycPD-1 antibodies or glycosylated PD-1 polypeptides can be administered before, during, after, or in various combinations relative to a second or an additional anti-cancer treatment. The administrations can be in intervals ranging from concurrently to minutes to days to weeks. In embodiments where the antibodies or polypeptides are provided to a patient separately from an anti-cancer agent, one would generally ensure that a significant period of time do not expire between the time of each delivery, such that the two compounds would still be able to exert an advantageously combined effect on the patient. In such instances, it is contemplated that one can provide a patient with the anti-glycPD-1 antibodies or glycosylated PD-1 polypeptides and the second therapy within about 12 to 24 or 72 h of each other and, more particularly, within about 6-12 h of each other. In some situations the time period for treatment can be extended significantly where several days (2, 3, 4, 5, 6, or 7) to several weeks (1, 2, 3, 4, 5, 6, 7, or 8) lapse between respective administrations.

In specific embodiments, the anti-glycPD-1 antibodies are administered in combination with one or more other anti-PD-1 antibodies, including administration in combination with pembrolizumab, nivolumab or pidilizumab to a patient for treatment of cancer. In other embodiments, the anti-glycPD-1 antibodies are administered in combination with one or more anti-PD-L1 antibodies to a patient for treatment of cancer. In specific embodiments, the anti-glycPD-1 antibodies are administered in combination with atezolizumab, durvalumab or avelumab. In other embodiments, the anti-glycPD-1 antibodies are administered in combination with one or more anti-CTLA-4 antibodies, and, in a specific embodiment, the anti-CLTA-4 antibody is ipilimumab. In other embodiments, the anti-glycPD-1 antibodies are administered with an agent that inhibits the activity of PD-1, PD-L1 or CTLA-4, for example an immunoadhesin that has the extracellular-receptor or ligand binding portion of the PD-1, PD-L1 or CTLA-4 protein fused to an Fc domain.

In specific embodiments, the anti-glycPD-1 antibodies are administered in combination with antibodies that preferentially bind glycosylated PD-L1 as compared to unglycosylated PD-L1. In particular, the anti-glycPD-1 antibodies may be administered in combination with chimeric or humanized forms of the anti-PD-L1 antibodies STM004 or STM115, which preferentially bind glycosylated PD-L1 as compared to unglycosylated PD-L1, and the amino acid sequences (and encoding nucleotide sequences) of the heavy and light chain variable domains are disclosed in PCT Publication WO2016/160792, published Oct. 6, 2016, entitled "Antibodies Specific To Glycosylated PD-L1 And Methods Of Use Thereof," which is incorporated herein by reference. The anti-glyc-PD-1 antibodies are also administered in combination with chimeric or humanized forms of anti-PD-L1 antibodies STM073 and SMT108, which preferentially bind glycosylated PD-L1 as compared to unglycosylated PD-L1, and the amino acid sequences (and encoding nucleotide sequences) of the heavy and light chain variable domains are disclosed in U.S. provisional application No. 62/314,652, filed Mar. 29, 2016, entitled "Dual Function Antibodies Specific To Glycosylated PD-L1 And Methods Of Use Thereof," which is incorporated herein by reference.

In certain embodiments, a course of treatment can last 1-90 days or more (this such range includes intervening days). It is contemplated that one agent can be given on any day of day 1 to day 90 (this such range includes intervening days) or any combination thereof, and another agent is given on any day of day 1 to day 90 (this such range includes intervening days) or any combination thereof. Within a single day (24-hour period), the patient can be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. The treatment cycles can be repeated as necessary.

Various combinations can be employed. Listed below are some examples with the treatment with the anti-glycPD-1 antibody or glycosylated PD-1 polypeptide as "A" and a second anti-cancer therapy as "B":

Chemotherapy

A wide variety of chemotherapeutic agents can be used in accordance with the present embodiments as the second therapy. A chemotherapeutic can be a compound or composition that is administered in the treatment of cancer. These agents or drugs can be categorized by their mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine;

---

A/B/A B/A/B B/B/A A/A/B A/B/B B/A/A A/B/B/B B/A/B/B B/B/B/A B/B/A/B
A/A/B/B A/B/A/B A/B/B/A B/B/A/A B/A/B/A B/A/A/B A/A/A/B B/A/A/A A/B/A/A
A/A/B/A

---

Administration of any antibodies, polypeptides, or pharmaceutical compositions provided herein, in combination of a second therapy to a patient will follow general protocols for the administration of such second therapy, taking into account the toxicity, if any, of the second therapy. Therefore, in some embodiments there is a step of monitoring toxicity that is attributable to combination therapy.

androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

Radiotherapy

Another conventional anticancer therapy that can be used in combination with the methods and compositions described herein is radiotherapy, or radiation therapy. Radiotherapy include using γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

Tumor microenvironment is intrinsically inhibitory due to the presence of myeloid-derived suppressor cells and regulatory T cells that infiltrate the tumor and function to suppress immune responses. In addition, the expression of certain inhibitory molecules on T cells and antigen presenting cells (APCs) can limit effective immune responses. Radiation mediates anti-tumor effects through the induction of tumor cell apoptosis, senescence, autophagy, and in some situations, can stimulate more effective immune responses.

The abscopal effect is a physiological process whereby targeted radiation of a primary tumor induces an anti-tumor response at a distant site that is not in the field of radiation. The mechanisms responsible for the abscopal effect are thought to be immune mediated and involve enhanced presentation of tumor antigens to T cells as well as the release of cytokines and other pro-inflammatory factors that stimulate local and systemic immune responses. As the abscopal effect affects tumors distally located from the primary tumor that receives radiation treatment, an agent that can trigger the abscopal effect would be particularly advantageous in treating metastatic tumors, which are often more difficult to treat once they have spread to secondary sites within the body.

The anti-glycPD-1 antibodies or glycosylated PD-1 polypeptides described herein can stimulate local and systemic immune response. In some embodiments, a therapeutically effective amount of the antibodies, polypeptides or pharmaceutical compositions as described herein are administered before, at the same time with, or after a radiotherapy to achieve a synergistic abscopal effect.

In some embodiments, a therapeutically effective amount of the antibodies, polypeptides or pharmaceutical compositions described herein are administered that effectively sensitizes a tumor in a host to irradiation. Irradiation can be ionizing radiation and in particular gamma radiation. In some embodiments, the gamma radiation is emitted by linear accelerators or by radionuclides. The irradiation of the tumor by radionuclides can be external or internal.

In some embodiments, the administration of the antibodies, polypeptides or pharmaceutical compositions described herein commences up to one month, in particular up to 10 days or a week, before the irradiation of the tumor. Additionally, irradiation of the tumor is fractionated the administration of the antibodies, polypeptides or pharmaceutical compositions described herein is maintained in the interval between the first and the last irradiation session.

Irradiation can be also be X-ray radiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Immunotherapy

The skilled artisan will understand that immunotherapies can be used in combination or in conjunction with methods of the embodiments. In the context of cancer treatment, immunotherapeutics generally rely on the use of immune effector cells and molecules to target and destroy cancer cells. Rituximab (RITUXAN®) is such an example. Checkpoint inhibitors, such as, for example, ipilumimab, pembrolizuman, nivolumab, and atezolizumab are other examples. The immune effector can be, for example, an antibody specific for some marker on the surface of a tumor cell. The antibody alone can serve as an effector of therapy or it can recruit other cells to actually affect cell killing. The antibody also can be conjugated to a drug or toxin (e.g., chemotherapeutic, radionuclide, ricin A chain, cholera toxin, pertussis toxin) and serve merely as a targeting agent. Alternatively, the effector can be a lymphocyte carrying a surface molecule that interacts, either directly or indirectly, with a tumor cell target. Various effector cells include cytotoxic T cells and NK cells.

In one aspect of immunotherapy, the tumor cell bear some marker that is amenable to targeting, i.e., is not present on the majority of other cells. Many tumor markers exist and any of these can be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, *Infect Immun.*, 66(11):5329-36 (1998); Christodoulides et al., *Microbiology*, 66(11):5329-36(1998)); cytokine therapy, e.g., interferons α, β, and γ, IL-1, GM-CSF, and TNF (Bukowski et al., *Clin Cancer Res.*, 4(10):2337-47 (1998); Davidson et al., *J Immunother.*, 21(5):389-98(1998); Hellstrand et al., *Acta Oncol.* 37(4): 347-53(1998)); gene therapy, e.g., TNF, IL-1, IL-2, and p53

(Qin et al., *Proc Natl Acad Sci USA*, 95(24):14411-6(1998); Austin-Ward and Villaseca, *Rev Med Chil,* 126(7):838-45 (1998); U.S. Pat. Nos. 5,830,880 and 5,846,945); and monoclonal antibodies, e.g., anti-PD1, anti-PDL1, anti-CD20, anti-ganglioside GM2, and anti-p185 (Topalian et al., *The New England journal of medicine,* 366:2443-2454 (2012); Brahmer et al., *The New England journal of medicine* 366:2455-2465 (2012); Hollander, *Front Immunol* (2012): 3:3. doi: 10.3389/fimmu.2012.00003; Hanibuchi et al., *Int J Cancer,* 78(4):480-5(1998); U.S. Pat. No. 5,824,311); all of which are hereby incorporated by reference in their entireties. It is contemplated that one or more anti-cancer therapies can be employed with the therapies described herein that involve the use anti-glycPD-1 antibodies or glycosylated PD-1 polypeptides.

Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment can be accomplished by perfusion, direct injection, or local application of the area with an additional anti-cancer therapy. Such treatment can be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments can be of varying dosages as well.

Other Agents

It is contemplated that other agents can be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions can increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, can be used in combination with certain aspects of the present embodiments to improve the treatment efficacy.

Kits and Diagnostics

In various aspects, provided herein is a kit containing therapeutic agents and/or other therapeutic and delivery agents. In some embodiments, a kit is contemplated for preparing and/or administering a therapy provided herein. The kit can comprise one or more sealed vials containing any of the pharmaceutical compositions provided herein. The kit can include, for example, at least an anti-glycPD-1 antibody, or a glycosylated PD-1 polypeptide, as well as reagents to prepare, formulate, and/or administer the components provided herein or perform one or more steps of the methods provided herein.

In some embodiments, the kit can include an anti-glycPD-1 antibody and at least one ancillary reagent. In some embodiments, the kit can include a glycosylated PD-1 polypeptide and at least one ancillary reagent.

In some embodiments, the kit further includes a second anticancer agent. The second anticancer agent can be a chemotherapeutic agent, a immunotherapeutic agent, a hormonal therapeutic agent, or a cytokine.

In some embodiments, the kit can also include a suitable container means, which is a container that does not react with components of the kit, such as an eppendorf tube, an assay plate, a syringe, a bottle, or a tube. The container can be made from sterilizable materials, such as plastic or glass.

The kit can further include an instruction sheet that outlines the procedural steps of the methods set forth herein, and will follow substantially the same procedures as described herein or are known to those of ordinary skill. The instruction information can be in a computer readable media containing machine-readable instructions that, when executed using a computer, cause the display of a real or virtual procedure of delivering a pharmaceutically effective amount of the antibodies or polypeptides provided herein. The kit can also include a notice in the form prescribed by a governmental agency regulating the manufacture, use or sale of pharmaceuticals or biological products, which notice reflects approval by the agency of manufacture, use or sale for human administration.

EXAMPLES

It is understood that modifications which do not substantially change the nature and spirit of the various embodiments described herein are also contemplated. Accordingly, the following example is intended to illustrate but not in any way limiting.

Materials and Methods

Cell culture, stable transfectants, and transfection. All cells were obtained from American Type Culture Collection (ATCC). These cells were grown in in DMEM/F I 2 or RPMI I 640 medium supplemented with 10% fetal bovine serum (FBS). PD-I stable transfectants in HEK293T cells were selected using puromycin (InvivoGen, San Diego, Calif., USA). For transient transfection, cells were transiently transfected with DNA, such as DNA encoding PD-I, using SN liposomes (Hu, M. C. et al., 2004, Cell, 117:225-237) Lipofectamine™ 2000 and lipofectamine LTX (Life Technologies, Carlsbad, Calif., USA).

Generation of stable cells using lentiviral infection. PD-1 gene was purchased from the Origene (rockville, MD, USA), and cloned into pCDH lentiviral expression vectors to establish PD-1-Flag expression cell lines using known molecular biological techniques. pCDHI PD-1-Flag expression vector was used as a template to generate the PD-1-Flag NQ mutants N49Q, N58Q, N74Q, N116Q, and 4NQ (N49Q/N58Q/N79Q/N116Q) by performing site directed mutagenesis. All constructs were confirmed using enzyme digestion and DNA sequencing. To generate PD-1 expressing stable cells, the plasmids were transfected into 293T cells with lipofectamin LTX transfection reagent. Twenty-four hours after transfection, the medium was changed, and then the medium was collected at 24-hour intervals. The collected medium containing lentivirus was centrifuged to eliminate cell debris, and filtered through 0.45-μm filters. Cells were seeded at 50% confluence 12 hours before infection, and the medium was replaced with medium containing lentivirus. After infection for 24 hours, the medium was replaced with fresh medium and the infected cells were selected with 1 μg/ml puromycin (InvivoGen).

Immunoblot analysis, immunocytochemistry and immunoprecipitation. Immunoblot analysis was performed as described previously (Lim et al., 2008, Gastroenterology, 135:2I 28-40; and Lee et al., 2007, Cell, 130:440-455). Image acquisition and quantification of band intensity were performed using Bio-Rad ChemiDoc imaging system (Bio-Rad, Hercules, Calif. USA). For immunocytochemistry, cells were fixed in 4% paraformaldehyde at room temperature for 15 minutes, permeabilized in 5% Triton X-100 for 5 minutes, and then were stained using primary antibodies. The secondary antibodies used were anti-mouse AlexaFluor 488 or 594 dye conjugate and/or anti-rabbit Alexa Fluor 488 or 594 dye conjugate (Life Technologies). Nuclei were stained with 4',6-diamidino-2-phenylindole (DAPI blue) (Life Technologies). After mounting, the cells were visualized using a multiphoton confocal laser-scanning microscope (Nikon A1+, Melville, N.Y., USA).

Flow Cytometry. Cells overexpressing PD-1 wild type and mutant proteins or control vector were isolated by trypsinization and collected in Cell Staining Buffer (CSB) (BioLegend, San Diego, Calif., US) at $2\times10^6$ cells/mL. 50 μL of cells were aliquoted to a 96 well round-bottom plate, to which 50 μL of 20 μg/mL primary antibody was added, followed by gentle mixing and 1 h incubation at 4° C. in the dark. Cells were washed with CSB, incubated with anti-mouse IgG-PE conjugate (10 μg/mL) with DAPI (1:100) 30 minutes 21° C. in the dark. Cells were washed and data acquired using Guava EasyCyte HT (Millipore Darmstadt, DE) or FACS Celesta (Becton Dickinson, Franklin Lakes, N.J., US) flow cytometer.

PD-L1 and PD-1 (PD-L1/PD-1) interaction assay. To measure the interaction of PD-1 protein and PD-L1 protein, PD-1 expressing cells were fixed in 4% paraformaldehyde at room temperature for 15 minutes and then were incubated with recombinant human PD-L1-Fc chimera protein (R&D Systems) for 1 hour. The secondary antibodies used were anti-human Alexa Fluor 488 dye conjugate (Life Technologies). The fluorescence intensity of Alexa Fluor 488 dye was then monitored using a real-time microscope IncuCyte (Essen BioScience, Ann Arbor, Mich., USA).

$K_D$ determination and binning by Octet. For high-throughput $K_D$ screening, antibody ligand was loaded to the sensor via 20 nM solution. Baseline was established in PBS containing 1 mg/ml bovine serum albumin (assay buffer), the association step was performed by submerging the sensors in a single concentration of analyte in assay buffer. Dissociation was performed and monitored in fresh assay buffer. All experiments were performed with sensor shaking at 1,000 rpm. ForteBio's data analysis software was used to fit the data to a 1:1 binding model to extract an association rate and dissociation rate. The $K_D$ was calculated using the ratio $k_d/k_a$. In a typical epitope binning assay, antigen PD-1-His (10 nM) was preincubated with the second antibody (10 nM) for 1 h at room temperature. Control antibody (20 nM) was loaded onto AMC sensors (ForteBio) and remaining Fc-binding sites on the sensor were blocked with a whole mouse IgG antibody (Jackson ImmunoResearch). The sensors were exposed to preinculated antigen-second antibody mixture. Raw data was processed using ForteBio's Data Analysis Software 7.0 and the antibody pairs were assessed for competitive binding. Additional binding by the second antibody indicates an unoccupied epitope (non-competitor), while no binding indicates epitope blocking (competitor).

Glycosylation analysis of PD-1. To confirm glycosylation of PD-1 protein, cell lysates were treated with the enzymes PNGase F, Endo H, 0-glycosidase (New England BioLabs, Ipswich, Mass., USA) as described by the manufacturer.

Statistical analysis. Data in bar graphs represents mean fold change relative to untreated or control groups with standard deviation of three independent experiments. Statistical analyses were performed using SPSS (Ver. 20, SPSS, Chicago, Ill.). The correlation between protein expression and BLBC subset was analyzed using Spearman's correlation and Mann-Whitney test. Student's t test was performed for experimental data. AP value<0.05 was considered statistically significant.

Example 1: Glycosylated PD-1 Binds to PD-L1

The role of glycosylation of PD-1 in binding to PD-L1 was tested with a PD-1/PD-L1 binding assay with 293T cells expressing wild type PD-1, having glycosylation at N49, N58, N79 and N116 and with 293T cells expressing mutant PD-1 in which the asparagine is substituted with a glutamine at all of these positions to block glycosylation. Thus, the mutant 4NQ is N49Q/N58Q/N79Q/N116Q. The cells were incubated with fluorescent-labeled PD-L1-Fc fusion proteins. Ligand and receptor binding was quantified by IncuCyte™ Zoom every hour, according to the manufacturer's instructions. FIG. 1A shows that cells expressing the wild type, i.e., glycosylated, PD-1 are stained green by the PD-L1-Fc fusion protein. FIG. 1B on the other hand shows that labeled PD-L1-Fc fusion does not bind to cells expressing the 4NQ mutant PD-1, which is not glycosylated. FIG. 1C graphs the level of green staining on the wild type, glycosylated PD-1-expressing cells and 4NQ mutant, unglycosylated PD-1-expressing cells over 24 hours. The binding of the PD-L1-Fc to the wild type, glycosylated PD-1-expressing cells increases over the 24 hours, while there is negligible PD-L1-Fc binding to the 4NQ, unglycosylated mutant PD-1-expressing cells. The experiment demonstrates that PD-L1 binds with far greater affinity to glycosylated PD-1 than to unglycosylated PD-1.

To determine whether glycosylation is required for PD-1-PD-L1 engagement, co-immunoprecipitation and Western blot analysis were performed to assess the interaction of PD-1 and PD-L1 in PD-1 WT or 4NQ expressing 293T cells. The lysates of PD-1 WT and 4NQ expressing 293T cells were incubated with or without PD-L1/Fc fusion proteins and then PD-1 proteins were immunoprecipitated with anti-Flag resins and analyzed by Western blot with anti-human IgG-HRP to detect the PD-L1/Fc and anti-Flag antibody to detect the PD-1 protein. As shown in FIG. 1D, PD-L1 binding to PD-1 (as detected by the anti-hIgG-HRP antibody on the top row) is observed when PD-L1/Fc is incubated with the wild type, glycosylated PD-1 but not when the PD-L1/Fc is incubated with the unglycosylated 4NQ PD-1 mutant. Anti-FLAG antibodies detected both wild type and 4NQ PD-1 proteins and the PD-L1/Fc as controls. The results support that glycosylation is required for PD-L1 and PD-1 association.

Example 2: Production of Anti-PD-1 Antibodies

Hybridomas producing monoclonal antibodies generated against glycosylated human PD-1 were obtained by the fusion of SP2/0 murine myeloma cells with spleen cells isolated from human PD-1-immunized BALB/c mice (n=6) (Antibody Solutions, Inc., Sunnyvale, Calif., USA) according to standardized protocol. Before fusion, sera from the immunized mice were validated for binding to the PD-1 immunogen using FACS analysis. Monoclonal antibody (MAb)-producing hybridomas were generated. The hybridomas that produced antibodies were again tested for specificity.

To this end, over 100 candidate MAb-producing hybridomas were selected, grown in ADCF medium, and their monoclonal antibody-containing supernatant was concentrated and purified. The candidate monoclonal antibodies were screened for preferential binding to glycosylated PD-1 as compared to unglycosylated PD-1. T293 cells overexpressing PD-1 WT (fully glycosylated) were tagged with biotin and then mixed with T293 cells overexpressing fully unglycosylated PD-1. Mixed cells were incubated with primary antibodies against PD-1 and were further washed with secondary antibodies conjugated with FITC. After washing, fluorescence intensity (MFI) was measured to assess relative binding of antibodies to membrane bound glycosylated or unglycosylated PD-1. Antibodies that exhibited significantly higher MFI on glycosylated PD-1 over unglycosylated PD-1 were identified as anti-glycPD-1 antibodies.

The purified MAbs were tested for their ability to neutralize or inhibit the interaction between PD-L1 and PD-1 (PD-L1/PD-1 binding interaction) using a live-cell imaging assay, Incucyte™, (Essen Bioscience). For this assay, 293T cells expressing PD-1 were incubated with anti-human PD-1 antibody and with fluorescent-labeled PD-L1-Fc fusion proteins. Ligand and receptor binding was quantified by Incycyte™ Zoom every hour, according to the manufacturer's instructions.

Two anti-glycPD-1 antibodies were identified that preferentially bind to glycosylated PD-1 as compared to unglycosylated PD-1, STM413 and STM432. The sequences of the heavy and light chain variable domains of the monoclonal antibodies are provided in Table 3. The antibodies were characterized for binding kinetics to glycosylated PD-1 using a BIACORE® assay. Results are provided in Table 6 below.

TABLE 6

BIACORE assay of anti-glyc-PD-1 antibody binding to PD-1.

| Antibody | Antigen | $k_a$ (1/Ms) | $k_d$ (1/s) | $K_D$ (M) |
|---|---|---|---|---|
| STM418 | PD-1-His | $8.44 \times 10^4$ | $7.78 \times 10^{-6}$ | $9.22 \times 10^{-11}$ |
| STM432 | PD-1-His | $1.79 \times 10^4$ | $5.30 \times 10^{-3}$ | $2.96 \times 10^{-7}$ |

The STM418 epitope on glycosylated PD-1 was determined using high-mass MALDI analysis on glycosylated PD-1 peptide fragments with antibody-antigen cross linking. The epitope of the antibody was determined to encompass the regions of glycosylated PD-1 from amino acids 34 to 44, 49 to 59 and 104 to 124 of SEQ ID NO: 1:

$^{34}$PP<u>T</u>F<u>S</u>PALLVV$^{44}$...$^{49}$NA<u>T</u>F<u>TC</u>SFSNT$^{59}$...
$^{104}$RDFHM<u>S</u>VVRAR<u>RN</u>D<u>S</u>GT<u>YL</u>CG$^{124}$ (amino acids 34 to 44, 49 to 59 and 104 to 124 of SEQ ID NO:1) where the binding contacts, as identified by antibody-antigen cross-linking experiments are underlined at positions 36, 38, 51, 53, 55, 109, 115, 118 and 121 of SEQ ID NO: 1.

The STM432 epitope on glycosylated PD-1 was determined using high-mass MALDI analysis with antibody-antigen cross-linking. The epitope was identified as follows in the human PD-1 sequence.

$^{91}$DCRE<u>R</u>VTQLPNGRDFHM$^{107}$ - - - $^{123}$CGAI<u>S</u>LAP<u>K</u>AQI$^{134}$ (amino acids 91 to 107 and 123 to 134 of SEQ ID NO:1). The epitope stretches from position D91 to position M107 and then position C123 to position I134 of the amino acid sequence of PD-1 in SEQ ID NO:1. The underlined positions, R95, R103, S127 and K131 are the positions that showed cross-linking to PD-1 antigen.

The monoclonal antibodies STM418 and STM432 were tested by western immunoblot analysis for binding to glycosylated wild type and mutant PD-1-Fc, where the mutant PD-1 proteins had one or more glycosylation sites removed by the mutation of an asparagine (N) to a glutamine (Q), and wild type PD-1 treated with PNGase F to remove glycosylation enzymatically. 0.5 µg each of PD-1-Fc proteins (wild type and mutants N49Q, N58Q, and N74Q) and PNGase F treated wild type PD-1 were analyzed by Western blot analysis and probed with STM418 and STM432, as detected with goat-Anti-mouse secondary antibody. FIG. 2 shows that STM418 binds to glycosylated wild type PD-1 and PD-1 that is mutant for the glycosylation sites at positions 49 and 58 (i.e. is glycosylated at positions 74 and 116), but does not bind to PD-1 with a mutant glycosylation site at position 74 or wild type PD-1 that has been deglycosylated by treatment with PNGase F. STM432 binds to wild type glycosylated PD-1 and PD-1 with a mutant glycosylation site at position 58, but does not bind to PD-1 with mutant glycosylation sites at either position 49 or 74 or wild type PD-1 that has been deglycosylated by treatment with PNGase F.

Binding of the anti-glycPD-1 antibodies to 293T cells expressing wild type PD-1, mutant PD-1 proteins or control 293T cells was assayed using the flow cytometry. Binding of STM418 and STM432 to 293T cells expressing wild type PD-1, N49Q PD-1, N58Q PD-1, N74Q PD-1, N116Q PD-1, and 4NQ PD-1 (mutations N to Q substitutions at positions 49, 58, 74, and 116), and control 293T cells that do not express PD-1 was assayed. FIGS. 3A and 3B present the results of flow cytometry of the cells after incubation with anti-glycPD-1 antibodies or controls and fluorescently labeled secondary antibody, and measured as MFI or measured fluorescent intensity. FIG. 3C shows the results from incubation of control mouse IgG. The MFI for binding of the anti-glycPD-1 antibodies and control antibodies to the cells expressing wild type and mutant PD-1 proteins and control cells are presented below in Table 7. The data show that STM418 binds to wild type, glycosylated PD-1 with an MFI that is about 128 times greater than the MFI for binding to the unglycosylated 4NQ mutant PD-1 and that STM432 binds to wild type, glycosylated PD-1 with an MFI that is about 43 times greater than the MFI for binding to the unglycosylated 4NQ mutant PD-1.

TABLE 7

MFI Values for Anti-GlycPD-1 Antibody binding to PD-1 expressing cells.

| MAb | 293T WTPD-1 MFI | 293T N49PD-1 MFI | 293T N58PD-1 MFI | 293T N74PD-1 MFI | 293T N116PD-1 MFI | 293T 4NQPD-1 MFI | 293T Blank MFI |
|---|---|---|---|---|---|---|---|
| STM418 | 3610 | 607 | 880 | 971 | 108 | 28 | 27 |
| STM432 | 1136 | 32 | 413 | 29 | 31 | 26 | 29 |
| Mouse IgG | 52 | 31 | 106 | 26 | 28 | 26 | 27 |

Example 3. Anti-GlycPD-1 Antibody Neutralizing Activity

To measure inhibition of PD-1 and PD-L1 protein interaction by antibodies, 293T cells overexpressing PD-1 were seeded into 96-well plates and incubated with the STM418 or STM432 antibodies, recombinant human PD-L1-Fc protein and anti-human-Fc Alexa Fluor 488 dye conjugate (Life Technologies, Carlsbad, Calif., US). Green fluorescence was measured every 2 hours by IncuCyte™ Zoom device and quantitated by IncuCyte™ Zoom Software (Essen BioScience, Ann Arbor, Mich., USA). FIG. 4A shows the binding of PD-L1-Fc to PD-1-expressing cells in the presence of concentrations of the anti-glycPD-1 antibody STM418 from 0.03 μg/ml to 4.0 μg/ml over 18 hours. STM418 inhibits PD-L1-Fc binding to PD-1 expressing cells in a concentration dependent matter. FIG. 4B plots the concentration of STM418 versus the percent activity of PD-1-PD-L1 binding to calculate the $EC_{50}$ of 0.132 μg/ml. FIG. 5A shows the binding of PD-L1-Fc to PD-1-expressing cells in the presence of concentrations of the anti-glycPD-1 antibody STM432 from 0.03 μg/ml to 4.0 μg/ml over 18 hours. STM432 inhibits PD-L1-Fc binding to PD-1 expressing cells in a concentration dependent matter. FIG. 5B plots the concentration of STM432 versus the percent activity of PD-1-PD-L1 binding to calculate the $EC_{50}$ of 0.110 μg/ml.

Example 4. Effect of Anti-GlycPD-1 Antibodies on T Cell Killing

To assay for the effect of the anti-glycPD-1 antibodies on cancer cells in the presence of T cells, T cells were isolated from human PBMC by magnetic αCD3-isolating antibody kit then activated by incubation with αCD3 antibody 100 ng/mL and IL-2 10 ng/mL for 72 hours. The activated T cells were added to pre-seeded BT549 cancer cells labeled with NucLight Red Lentivirus reagent (Essen BioScience, Ann Arbor, Mich., USA) in a 96-well plate with RPMI 1640 together with 10 μg/mL STM418, STM432 antibodies or mIgG1 isotype as a control. T cell killing of cancer cells was detected over time using an Incucyte Zoom (Essen Biosciences) by red nuclear image count (proliferation) calculated by Incucyte Zoom 2016 software. FIG. 6 shows the reduction in the proliferation of cancer cells in the presence of activated T cells and either STM418 or STM432 antibodies over 90 hours as compared cancer cells in the presence of activated T cells incubated with control murine IgG isotype.

Example 5: Antibody Humanization

As indicated above, for certain purposes, including for example, use in the in vivo treatment of human disease, it is preferred to employ a humanized derivative of the mouse monoclonal antibody. To form such humanized antibodies, the framework sequences of the mouse monoclonal antibodies (the "Parental" sequences) are first aligned with framework sequences of a set of "Acceptor" human antibodies in order to identify differences in the framework sequences. Humanization are accomplished by substituting non-matching framework residues between the Parental and the Acceptor. Substitutions at potentially important positions such as those in the Vernier zone, the VH/VL inter-chain interface or CDR canonical class determining positions were analyzed for prospective back mutations (see, Foote, J. et al., *J. Molec. Biol.* 224:487-499 (1992)).

The Conserved Domain Database (COD) (Marchler-Bauer, et al. (2011) *Nucleic Acids Res.* 39:D225-D229) can be used to determine the domain content of each amino-acid chain and the approximate boundaries of each domain. Variable domain boundaries can be exactly determined along with the boundaries of the CDRs according to several commonly used definitions (Kabat, E. A. et al. (1991) "*Sequences of Proteins of Immunological Interest*," Fifth Edition. NIH Publication No. 91-3242; Chothia, C. et al., *J. Mol. Biol.* 196:901-917 (1987); Honegger, A. et al., *J. Molec. Biol.* 309(3):657-670 (2001))

Multiple alignments of the Parental sequence to the mouse and human germline sequences are generated using MAFFT (Katoh, K. et al., *Nucleic Acids Res.* 30: 3059-3066 (2002)) and entries in each alignment are ordered according to the sequence identity to the Parental sequence. Reference sets are reduced to a unique set of sequences by clustering at 100% sequence identity and excluding redundant entries.

The optimal Acceptor framework selection is based on the overall Parental antibodies sequence identity to the Acceptor across the framework of both chains; however the positions that compose the VH/VL inter-chain interface are of particular interest. Additionally, the CDR-loops lengths and CDR positions responsible for the discrete set of canonical structures that has been defined for 5 of the CDRs (Chothia, C. et al., *J. Mol. Biol.* 196:901-917 (1987); Martin, A. C. et al., *J. Molec. Biol* 263:800-815 (1996); Al-Laziniki, B. et al., *J. Molec. Biol.* 273:927-948(1997)) are compared to the germlines, in order to determine which germline frameworks have both the same interface residues and are known to support similar CDR-loop conformations.

Based on the parent antibody's sequence alignment to the human germlines the closest matching entries are identified. The choice of the preferred human germline is based on the ordered criteria: (1) Sequence identity across the framework; (2) Identical or compatible inter-chain interface residues; (3) Support loops with the Parental CDRs canonical conformations; (4) The combination of heavy and light germlines are found in expressed antibodies; and (5) Presence of N-glycosylation sites that have to be removed.

A structural model of Fv-region of the humanized antibody is generated. Candidate structural template fragments for the FR and CDRs as well as the full Fv are scored, ranked and selected from an antibody database based on their sequence identity to the target, as well as qualitative crystallographic measures of the template structure such as the resolution, in Angstroms (Å).

In order to structurally align the CDRs to the FR templates, 5 residues on either side of the CDR are included in the CDR template. An alignment of the fragments is generated based on overlapping segments and a structural sequence alignment generated. The template fragments along with the alignment were processed by MODELLER (SalI, A. et al.; *J. Molec. Biol.* 234:779-815(1993)). This protocol creates conformational restraints derived from the set of aligned structural templates. An ensemble of structures which satisfied the constraints are created by conjugate gradient and simulated annealing optimization procedures. Model structures are selected from this ensemble on the basis of an energy score, derived from the score of the proteins structure and the satisfaction of the conformational constraints. The models are inspected and the side chains of the positions which differed between the target and template are optimized using a side chain optimization algorithm and energy minimized. A suite of visualization and computational tools are used to assess the CDRs conformational variability, local packing and surface analysis to select one or more preferred models.

A structural model of the Parental antibody is constructed and inspected for imperfections such as poor atomic packing, strain in bond lengths, bond angles or dihedral angles. These imperfections may indicate potential issues with the structural stability of the antibody. The modeling protocol seeks to minimize such imperfections. The initial structural model of the Humanized Fv contains all safe substitutions (i.e., substitutions that should not affect binding affinity or stability) and cautious substitutions (i.e., the position substitution is made but the position may be important for binding affinity). Substitutions at positions that are considered to be associated with a risk a decreased binding affinity or reduced stability are not altered. The template search and selection is performed separately to the Parental template search in order to create a good stand-alone model rather than a closely matching variant model of the Parental. As the assessment of potential substitutions is performed the model is updated to reflect the preferred substitutions and the effect of back mutations.

Throughout this application various publications have been referenced. The disclosures of these publications in their entireties are hereby incorporated by reference in this application in order to more fully describe the state of the art to which this disclosure pertains. While examples of certain particular embodiments are provided herein, it will be apparent to those skilled in the art that various changes and modifications may be made. Such modifications are also intended to fall within the scope of the appended claims.

What is claimed is:

1. An isolated antibody which binds to glycosylated PD-1, wherein said antibody has a VH domain comprising CDRs H1, H2, and H3 having the amino acid sequences of SEQ ID NO: 6, SEQ ID NO: 7, and SEQ ID NO: 8, respectively, or having the amino acid sequences of SEQ ID NO: 9, SEQ ID NO: 10, and SEQ ID NO: 8, respectively, or having the amino acid sequences of SEQ ID NO: 11, SEQ ID NO: 12, and SEQ ID NO: 8, respectively, or having the amino acid sequences of SEQ ID NO: 13, SEQ ID NO: 14, and SEQ ID NO: 15, respectively; and wherein said antibody has a VL domain comprising CDRs L1, L2 and L3 with amino acid sequences of SEQ ID NO: 16, SEQ ID NO: 17, and SEQ ID NO: 18, respectively, or having the amino acid sequences of SEQ ID NO: 19, SEQ ID NO: 20, and SEQ ID NO: 21, respectively.

2. An isolated antibody which binds to glycosylated PD-1, wherein the VH domain of said antibody has an amino acid sequence of SEQ ID NO: 3 and the VL of said antibody has an amino acid sequence of SEQ ID NO: 5.

3. An isolated antibody which binds to glycosylated PD-1, wherein said antibody has a VH domain comprising CDRs H1, H2 and H3 having the amino acid sequences of SEQ ID NO: 26, SEQ ID NO: 27, and SEQ ID NO: 28, respectively, or having the amino acid sequences of SEQ ID NO: 29, SEQ ID NO: 30, and SEQ ID NO: 28, respectively, or having the amino acid sequences of SEQ ID NO: 31, SEQ ID NO: 32, and SEQ ID NO: 28, respectively, or having the amino acid sequences of SEQ ID NO: 33, SEQ ID NO: 34, and SEQ ID NO: 35, respectively; and wherein said antibody has a VL domain comprising CDRs L1, L2 and L3 having the amino acid sequences of SEQ ID NO: 36, SEQ ID NO: 37, and SEQ ID NO: 38, respectively, or having the amino acid sequences of SEQ ID NO: 39, SEQ ID NO: 40, and SEQ ID NO: 41, respectively.

4. The isolated antibody of claim 1, wherein said antibody comprises one or more human framework regions.

5. The isolated antibody claim 4, wherein said antibody comprises a human constant domain.

6. The isolated antibody of claim 1, wherein the antibody is one selected from the group consisting of a Fab', a F(ab')2, a F(ab')3, a monovalent scFv, a bivalent scFv, an IgG antibody, an IgM antibody, an IgA antibody, and an antigen binding fragment of an IgG, IgM, or IgA antibody.

7. A composition comprising the isolated antibody of claim 1 and a pharmaceutically acceptable carrier.

8. The isolated antibody according to claim 3, wherein the antibody is one selected from the group consisting of a Fab', a F(ab')2, a F(ab')3, a monovalent scFv, a bivalent scFv, an IgG antibody, an IgM antibody, an IgA antibody, and an antigen binding fragment of an IgG, IgM, or IgA antibody.

9. An isolated antibody which binds to glycosylated PD-1 having a VH domain comprising SEQ ID NO: 23 and VL domain comprising SEQ ID NO: 25.

10. A composition comprising the antibody of claim 3 and a pharmaceutically acceptable carrier, diluent, excipient, or vehicle.

11. The isolated antibody of claim 3, wherein the antibody comprises human framework regions.

12. The isolated antibody of claim 11, wherein the antibody comprises human constant domains.

13. The isolated antibody of claim 12, wherein the antibody is an IgG antibody, an IgM antibody, or an IgA antibody.

14. The isolated antibody of claim 5, wherein the antibody is an IgG antibody, an IgM antibody, or an IgA antibody.

15. A method for treating a subject having a PD-L1 positive cancer comprising administering an effective amount of the composition of claim 7 to the subject.

16. The method of claim 15, wherein the cancer is at least one cancer selected from the group consisting of a breast cancer, a lung cancer, a head & neck cancer, a prostate cancer, an esophageal cancer, a tracheal cancer, a skin cancer, a brain cancer, a liver cancer, a bladder cancer, a stomach cancer, a pancreatic cancer, an ovarian cancer, a uterine cancer, a cervical cancer, a testicular cancer, a colon cancer, a rectal cancer, and a skin cancer.

17. The method of claim 15, further comprising administering at least a second anti-cancer therapy to the subject.

18. A method for assessing PD-1 glycosylation comprising contacting a biological sample with the antibody according to claim 1, wherein detection of binding of said antibody indicates that the sample comprises glycosylated PD-1.

19. The method of claim 18, wherein the sample is cell sample from a cancer or tumor of a subject.

20. A method for treating a PD-L1 positive cancer in a subject in need of said treatment, said method comprising administering to the subject an effective amount of the antibody according to claim 3.

21. The method of claim 20, wherein the cancer is at least one cancer selected from the group consisting of a hematological cancer, a breast cancer, a lung cancer, a head & neck cancer, a prostate cancer, an esophageal cancer, a tracheal cancer, a skin cancer, a brain cancer, a liver cancer, a bladder cancer, a stomach cancer, a pancreatic cancer, an ovarian cancer, a uterine cancer, a cervical cancer, a testicular cancer, a colon cancer, a rectal cancer, and a skin cancer.

22. A method of assessing PD-1 glycosylation in a biological sample, said method comprising contacting a biological sample with an antibody according to claim 3, wherein detection of binding of said antibody indicates that the sample comprises glycosylated PD-1.

23. The method of claim 22, wherein the sample is a cell sample from a cancer or tumor of a subject.

* * * * *

SEQUENCE LISTING

```
<160> NUMBER OF SEQ ID NOS: 42

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190
```

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaagtgatgc tggtggagtc tgggggaggc ttagtgaagc ctggagggtc cctgaaactc     60
tcctgtgcag cctctggatt cactttcagt agctatggca tgtcttgggt tcgtcagact    120
ccggagaaga ggctggagtg ggtcgcaacc attagtggtg gtggtggtaa cacctactat    180
ccagacactg tgaagggccg attcaccatc tccagagaca atgccaagaa caccctgtac    240
ctgcaaatga gcagtctgag gtctgaggac acggccttgt attattgtac aagctattac    300
tacgggattg actactgggg ccaaggcacc actctcacag tctcctca                 348

<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Gly Asn Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Thr Ser Tyr Tyr Tyr Gly Ile Asp Tyr Trp Gly Gln Gly Thr Thr Leu
            100                 105                 110

Thr Val Ser Ser
        115

<210> SEQ ID NO 4
<211> LENGTH: 324

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gacattgtga tgacccagtc tcacaaattc atgtccacat cagtaggaga cagggtcagc      60
atcacctgca aggccagtca ggatgtgagt actgctgtag cctggtatca acaaaaacca     120
gggcaatctc ctaaattact gatttactgg gcatccaccc ggcaaactgg agtccctgat     180
cgcttcacag gcagtggatc tgggacagag tatactctca ccatcagcag tgtgcaggct     240
gaagacctgg cactttatta ctgtcagcaa cattatagca ttccgtggac gttcggtgga     300
ggcaccaagc tggaaatcaa acgg                                            324
```

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Gln Thr Gly Val Pro Asp Arg Phe Thr Gly
    50                  55                  60

Ser Gly Ser Gly Thr Glu Tyr Thr Leu Thr Ile Ser Ser Val Gln Ala
65                  70                  75                  80

Glu Asp Leu Ala Leu Tyr Tyr Cys Gln Gln His Tyr Ser Ile Pro Trp
                85                  90                  95

Thr Phe Gly Gly Gly Thr Lys Leu Glu Ile Lys Arg
            100                 105
```

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Gly Phe Thr Phe Ser Ser Tyr
1               5
```

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Ser Gly Gly Gly Gly Asn
1               5
```

```
<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Tyr Tyr Gly Ile Asp Tyr
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Phe Thr Phe Ser Ser Tyr Gly Met Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ile Ser Gly Gly Gly Gly Asn Thr Tyr
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Tyr Gly Met Ser
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Ile Ser Gly Gly Gly Gly Asn Thr Tyr Tyr Pro Asp Thr Val Lys
1               5                   10                  15

Gly

<210> SEQ ID NO 13
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 13

Ser Ser Tyr Gly Met Ser
1               5

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Val Ala Thr Ile Ser Gly Gly Gly Gly Asn Thr Tyr
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser Tyr Tyr Tyr Gly Ile Asp
1               5

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ala Ser Gln Asp Tyr Ser Thr Ala Val Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Ala Ser Thr Arg Gln Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln His Tyr Ser Ile Pro Trp Thr
1               5
```

```
<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Thr Ala Val Ala Trp Tyr
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Leu Ile Tyr Trp Ala Ser Thr Arg Gln
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln His Tyr Ser Ile Pro Trp
1               5

<210> SEQ ID NO 22
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gaagtgatgc tggtggagcc tgggggaggc ttagtgaagc ctggagggtc cctgaaactc      60
tcctgtgcag cctctggatt cactttcagt agctatggca tgtcttgggt tcgccagact     120
ccggagaaga ggctggagtg ggtcgcaacc attagtggtg gtggtgctaa cacctactat     180
ccagacactg tgaagggccg attcaccatc tccagagaca atgccaagaa caccctgtac     240
ctgcaaatga acagtctgag gtctgaggac acggccttgt attactgtgc aagatatggt     300
tacgacacgg tctttgctta ctggggccaa gggactctgg tcactgtctc tgca           354

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Met Leu Val Glu Pro Gly Gly Gly Leu Val Lys Pro Gly Gly
1               5                   10                  15

Ser Leu Lys Leu Ser Cys Ala Ala Ser Gly Phe Thr Phe Ser Ser Tyr
```

```
                    20                  25                  30
Gly Met Ser Trp Val Arg Gln Thr Pro Glu Lys Arg Leu Glu Trp Val
            35                  40                  45

Ala Thr Ile Ser Gly Gly Ala Asn Thr Tyr Tyr Pro Asp Thr Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ser Glu Asp Thr Ala Leu Tyr Tyr Cys
                85                  90                  95

Ala Arg Tyr Gly Tyr Asp Thr Val Phe Ala Tyr Trp Gly Gln Gly Thr
            100                 105                 110

Leu Val Thr Val Ser Ala
        115

<210> SEQ ID NO 24
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gacattgtgc tgacccaatc tccagcttct ttggctgtgt ctctagggca gaaggccacc      60
atctcctgca gagccagcga aagtgttgat gattatggca ttggttttat gaactggttc     120
caacagaaac caggtcagcc acccaaactc ctcatctata ctacatccaa ccaaggatcc     180
ggggtccctg ccaggtttag tggcagtggg tctgggacag acttcagcct caacatccat     240
cctatggtgg aggatgatac tgcaatgtat ttctgtcagc aaagtaagga ggttccgtgg     300
acgttcggtg gcggcaccaa gctggaaatc aaa                                  333

<210> SEQ ID NO 25
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Val Leu Thr Gln Ser Pro Ala Ser Leu Ala Val Ser Leu Gly
 1               5                  10                  15

Gln Lys Ala Thr Ile Ser Cys Arg Ala Ser Glu Ser Val Asp Asp Tyr
            20                  25                  30

Gly Ile Gly Phe Met Asn Trp Phe Gln Gln Lys Pro Gly Gln Pro Pro
        35                  40                  45

Lys Leu Leu Ile Tyr Thr Thr Ser Asn Gln Gly Ser Gly Val Pro Ala
    50                  55                  60

Arg Phe Ser Gly Ser Gly Ser Gly Thr Asp Phe Ser Leu Asn Ile His
 65                  70                  75                  80

Pro Met Val Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 26
<211> LENGTH: 8
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 26

Gly Phe Thr Phe Ser Ser Ala Tyr
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Ser Gly Gly Gly Ala Asn
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Tyr Gly Tyr Asp Thr Val Phe Ala Tyr
1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Gly Phe Thr Phe Ser Ser Ala Tyr Gly Met Ser
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Thr Ile Ser Gly Gly Gly Ala Asn Thr Tyr
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Ser Tyr Gly Met Ser
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Ile Ser Gly Gly Gly Ala Asn Thr Tyr Tyr Pro Asp Thr Val Lys
1               5                   10                  15
Gly

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Ser Tyr Gly Met Ser
1               5

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Val Ala Thr Ile Ser Gly Gly Gly Ala Asn Thr Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Tyr Gly Tyr Asp Thr Val Phe Ala
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Ser Glu Ser Val Asp Asp Tyr Gly Ile Gly Phe Met Asn
1               5                   10                  15

<210> SEQ ID NO 37
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 37

Thr Thr Ser Asn Gln Gly Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Gln Ser Lys Glu Val Pro Trp Thr
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Asp Tyr Gly Ile Gly Phe Met Asn Trp Phe
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Leu Ile Tyr Thr Thr Ser Asn Gln Gly
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Gln Ser Lys Glu Val Pro Trp
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 42

His His His His His His
1               5